US011833199B2

(12) United States Patent
    Khurana

(10) Patent No.: US 11,833,199 B2
(45) Date of Patent: Dec. 5, 2023

(54) PEPTIDE FRAGMENTS FROM FILOVIRUSES AND THEIR USES

(71) Applicant: The United States of America, as represented by the Secretary, Department of Health and Human Services, Silver Spring, MD (US)

(72) Inventor: Surender Khurana, Clarksburg, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 86 days.

(21) Appl. No.: 17/527,968

(22) Filed: Nov. 16, 2021

(65) Prior Publication Data

US 2022/0072119 A1    Mar. 10, 2022

Related U.S. Application Data

(63) Continuation of application No. 16/346,009, filed as application No. PCT/US2017/059407 on Oct. 31, 2017, now Pat. No. 11,202,824.

(60) Provisional application No. 62/414,960, filed on Oct. 31, 2016.

(51) Int. Cl.
   *A61K 39/12*   (2006.01)
   *C07K 14/005*  (2006.01)
   *G01N 33/569*  (2006.01)
   *A61K 39/00*   (2006.01)

(52) U.S. Cl.
   CPC ............ *A61K 39/12* (2013.01); *C07K 14/005* (2013.01); *G01N 33/56983* (2013.01); *A61K 2039/6081* (2013.01); *C12N 2760/14122* (2013.01); *C12N 2760/14134* (2013.01); *G01N 2469/20* (2013.01); *G01N 2800/26* (2013.01)

(58) Field of Classification Search
   None
   See application file for complete search history.

(56) References Cited

U.S. PATENT DOCUMENTS

2003/0186874 A1   10/2003   Barney et al.
2007/0082011 A1    4/2007   Lehrer et al.

FOREIGN PATENT DOCUMENTS

| CN | 103864904 B | 1/2016 |
| WO | WO 2001/003723 A1 | 1/2001 |
| WO | WO 2016/101075 A1 | 6/2016 |

OTHER PUBLICATIONS

Davidson et al. "Mechanism of Binding to Ebola Virus Glycoprotein by the ZMapp, ZMAb, and MB-003 Cocktail Antibodies." *J. Virol.* 89 No. 21 (2015): 10982-10992 (11 pages).
Flyak et al. "Cross-Reactive and Potent Neutralizing Antibody Responses in Human Survivors of Natural Ebolavirus Infection." *Cell* 164 No. 3 (2016): 392-405 (28 pages).
Geisbert et al., "Single-injection vaccine protects nonhuman promates against ingection with Marberg virus ant three species of Ebola virus." *J. Virol.* 83, No. 14 (2009): 7296-7304 (9 pages).
Khurana, et al. "Human antibody repertoire after VSV-Ebola vaccination identifies novel targets and virus-neutralizing IgM antibodies." *Nature Medicine* 22, No. 12 (2016): 1439-1447, plus supplemental material (24 pages).
Kiraly et al., Evaluation of anti-influenza efficiency of polyclonal IgG antibodies specific to the ectodomain of M2 protein of influenza A virus by passive immunization of mice, 2011, Acta Virologica, vol. 55, pp. 261-265.
Lee et al. "Structure of the Ebola virus glycoprotein bound to an antibody from a human survivor." *Nature* 454 No. 7201 (2008): 177-182, 2008 (17 pages).
Murin et al. "Structures of protective antibodies reveal sites of vulnerability on Ebola virus." *Proc. Nat'l. Acad. Sci. U.S.A.* 111, No. 48 (2014): 17182-17187, including supplemental materials (12 pages).

*Primary Examiner* — Benjamin P Blumel
(74) *Attorney, Agent, or Firm* — Klarquist Sparkman, LLP

(57) ABSTRACT

Isolated peptides comprising one or more antigenic sites of filovirus glycoprotein and methods of their use and production are disclosed. Nucleic acid molecules encoding the peptides are also provided. In several embodiments, the peptides can be used to induce an immune response to filovirus glycoprotein, such as Zaire ebolavirus glycoprotein, in a subject, for example, to treat or prevent infection of the subject with the virus.

12 Claims, 35 Drawing Sheets

Specification includes a Sequence Listing.

FIG. 1A
FIG. 1B
FIG. 1C
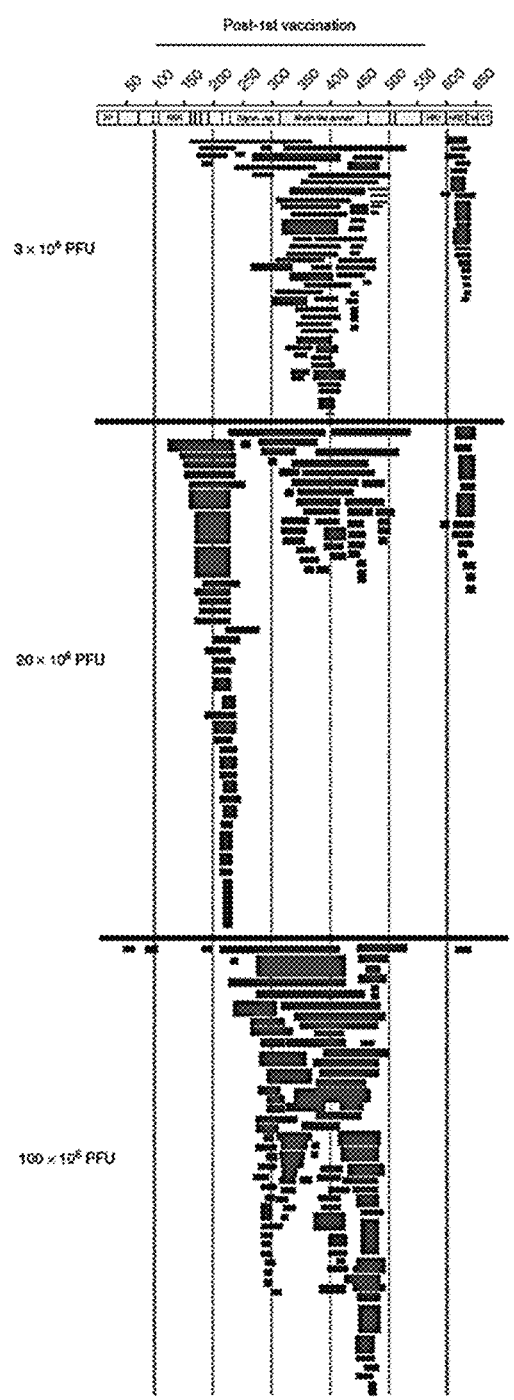
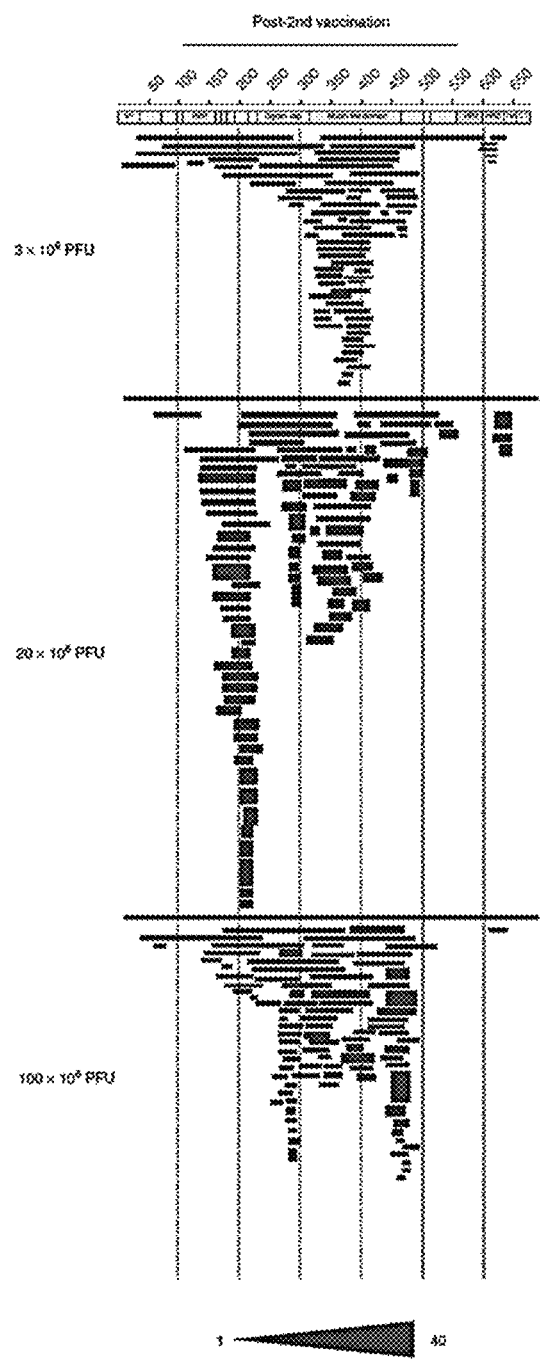

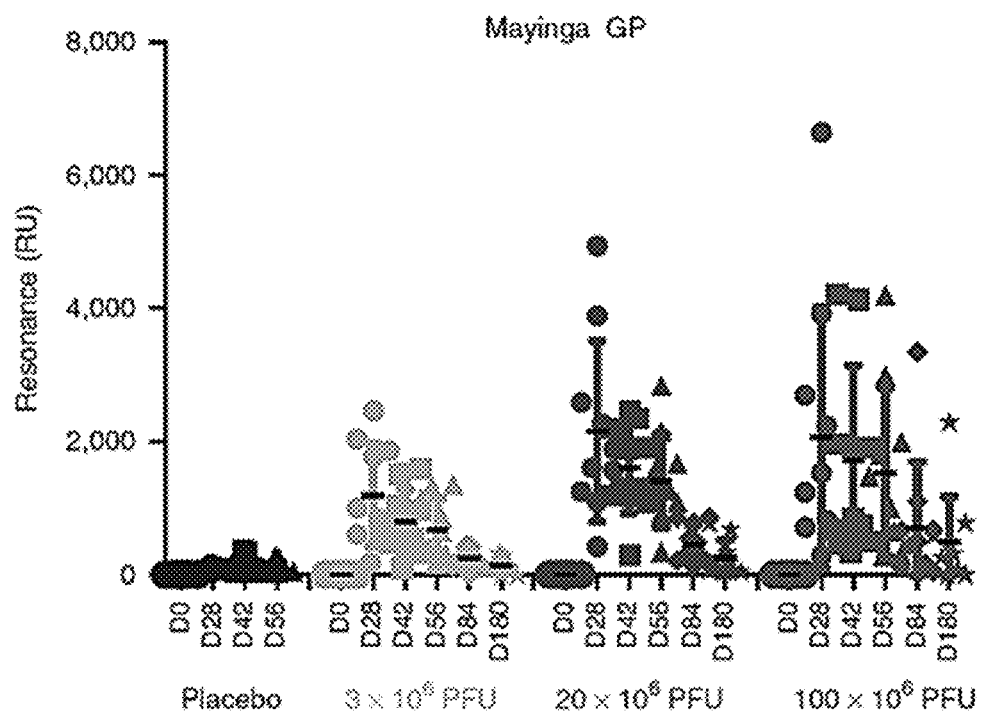
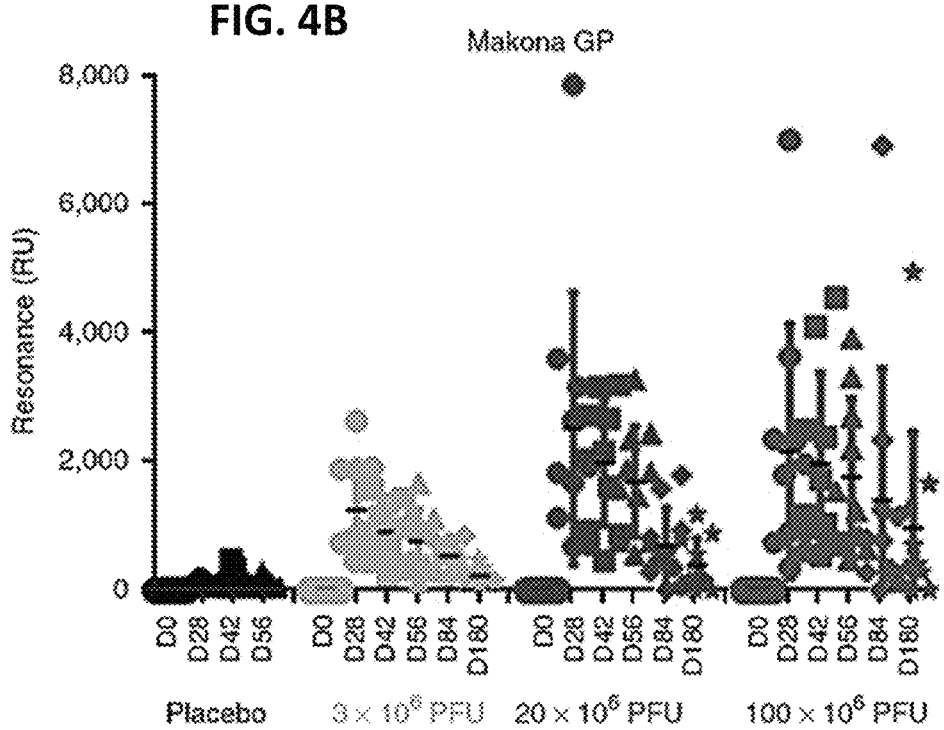

FIG. 5A Isotype of GP-binding antibodies

FIG. 5B GP binding

FIG. 5C IgM isotyping

| Site | SEQ ID NO: 35 AA | SEQ ID NO: 35 Sequence | 3x10⁶ Post-1st | 3x10⁶ Post-2nd | 20x10⁶ Post-1st | 20x10⁶ Post-2nd | 100x10⁶ Post-1st | 100x10⁶ Post-2nd |
|---|---|---|---|---|---|---|---|---|
| I | 1-36 | MGVTGILQLPRDRFKTSFFLWVIILFQRTFSIPLG | 0% | 1% | 1% | 0% | 0% | 0% |
| II | 32-273 | SIPLGVIHNSTLQVSDVDKLVCRDKLSSTNQLRSVGLNLEGNGVATDV PSATKRWGFFRSGVPPKVVNYEAGEWAENCYNLEIKKPDGSECLPAAP DGRGFPRCRYVHKVSGTGPCAGDFAFHKEGAFFLYDRLASTVIYRGT TFAEGVVAFLILPQAKKDFFSSHPLREPVNATEDPSSGYYSTIRYQAT GFGTNETEYLFEVDNLTYVQLESRFTPQFLQLNETIYTSGKRSNITG KL | 0% | 2% | 0% | 0% | 0% | 1% |
| II.1 | 152-220 | AFHKEGAFFLYDRLASTVIYRGTFAEGVVAFLILPQAKKDFFSSHPLR EPVNATEDPSSGYYSTIRY | 0% | 2% | 18% | 15% | 0% | 2% |
| II.2 | 195-226 | SSHPLREPVNATEDPSSGYYSTIRYQATGFG | 2% | 0% | 11% | 15% | 0% | 1% |
| III | 205-355 | ATEDPSSGYYSTIRYQATGFGTNETEYLFEVDNLTYVQLESRFTPQF LQLNETIYTSGKRSNTTGKLIWKVNPEIDTTIGEWAFWETKKNLTRKI RSEELSFTVVSNGAKNISGQSPARTSSDPGTNTTTEDHKIMASENSSA MVQVHS | 1% | 2% | 1% | 3% | 2% | 4% |
| III.1 | 210-220 | SSGYYSTIRY | 0% | 0% | 13% | 10% | 0% | 1% |
| IV | 267-419 | SNTTGKLIWKVNPEIDTTIGEWAFWETKKNLTRKIRSEELSFTVVSNGA KNISGQSPARTSSDPGTNTTTEDHKIMASENSSAMVQVHSQGREAAV SHLITLATISTSPQSLTTKPGPDNSTHNTPVYKLDISEATQVEQHHRRT DNDSTASD | 2% | 1% | 1% | 1% | 7% | 0% |
| IV.1 | 282-305 | DTTIGEWAFWETKKNLTRKIRSEE | 2% | 1% | 1% | 6% | 8% | 9% |
| IV.2 | 286-296 | GEWAFWETKKN | 1% | 5% | 1% | 7% | 10% | 12% |
| IV.3 | 286-364 | GEWAFWETKKNLTRKIRSEELSFTVVSNGAKNISGQSPARTSSDPGT NTTTEDHKIMASENSSAMVQVHSQGREAAVSH | 2% | 2% | 1% | 6% | 3% | 5% |

FIG. 6B

| Site | SEQ ID NO:35 AA | SEQ ID NO:35 Sequence | 3x10⁶ Post-1ˢᵗ | 3x10⁶ Post-2ⁿᵈ | 20x10⁶ Post-1ˢᵗ | 20x10⁶ Post-2ⁿᵈ | 100x10⁶ Post-1ˢᵗ | 100x10⁶ Post-2ⁿᵈ |
|---|---|---|---|---|---|---|---|---|
| V | 336-582 | TEDHKIMASENSSAMVQVHSQGREAAVSHLTTLATISTSPQSLTTKPG PDNSTHNTPVYKLDISEATQVEQHHRRTDNDSTASDTPSATTAAGPP KAENTNTSKSTDFLDPATTTSPQNHSETAGNNNTHHQDTGEESASSG KLGLITNTIAGVAGLITGGRRTRREAIVNAQPKCNPNLHYWTTQDEGA AIGLAWIPYFGPAAEGIYIEGLMHNQDGLICGLRQLANETTQALQLFLR ATTELRTF | 0% | 1% | 0% | 0% | 1% | 3% |
| V.1 | 343-368 | ASENSSAMVQVHSQGREAAVSHLTTL | 3% | 5% | 4% | 8% | 4% | 7% |
| V.2 | 372-420 | STSPQSLTTKPGPDNSTHNTPVYKLDISEATQVEQHHRRTDNDSTAS DT | 22% | 23% | 6% | 9% | 10% | 8% |
| V.3 | 380-491 | TKPGPDNSTHNTPVYKLDISEATQVEQHHRRTDNDSTASDTPSATTAA GPPKAENTNTSKSTDFLDPATTTSPQNHSETAGNNNTHHQDTGEESA SSGKLGLITNTIAGVAG | 3% | 5% | 4% | 1% | 7% | 2% |
| V.4 | 424-447 | TTAAGPPKAENTNTSKSTDFLDPA | 5% | 1% | 5% | 1% | 1% | 0% |
| V.5 | 436-491 | NTSKSTDFLDPATTTSPQNHSETAGNNNTHHQDTGEESASSGKLGLIT NTIAGVAG | 8% | 5% | 1% | 2% | 18% | 11% |
| V.6 | 456-484 | SETAGNNNTHHQDTGEESASSGKLGLITN | 1% | 2% | 1% | 0% | 8% | 17% |
| V.7 | 469-498 | TGEESASSGKLGLITNTIAGVAGLITGGRR | 3% | 6% | 3% | 4% | 2% | 3% |
| VI | 617-645 | KNITDKIDQIIHDFVDKTLPDQGDNDNWW | 22% | 9% | 13% | 4% | 1% | 1% |

FIG. 7

| Site | AA | Mayinga(%) | Sudan(%) | Bundibugyo(%) | Kikwit(%) | Makona(%) |
|---|---|---|---|---|---|---|
| I | 1-36 | 100 | 88.89 | 88.89 | 100 | 100 |
| II | 32-273 | 100 | 79 | 87.2 | 100 | 99.6 |
| II.1 | 152-220 | 100 | 74 | 82.61 | 100 | 100 |
| II.2 | 195-226 | 100 | 62.5 | 65.62 | 100 | 100 |
| III | 205-355 | 100 | 54.3 | 65.57 | 98.68 | 97.35 |
| III.1 | 210-220 | 100 | 63.64 | 63.64 | 100 | 100 |
| IV | 267-419 | 100 | 28.11 | 49.02 | 96.73 | 95.42 |
| IV.1 | 282-305 | 100 | 70.83 | 79.17 | 100 | 100 |
| IV.2 | 286-298 | 100 | 90.91 | 90.91 | 100 | 100 |
| IV.3 | 286-364 | 100 | 48.1 | 50.63 | 97.47 | 94.94 |
| V | 338-582 | 100 | 51.42 | 54.43 | 96.76 | 95.95 |
| V.1 | 343-368 | 100 | 42.3 | 38.46 | 100 | 96.15 |
| V.2 | 372-420 | 100 | 28.57 | 28.57 | 93.88 | 93.88 |
| V.3 | 380-491 | 100 | 33.93 | 26.79 | 95.54 | 93.75 |
| V.4 | 424-447 | 100 | 20.84 | 25 | 87.5 | 79.17 |
| V.5 | 436-491 | 100 | 37.5 | 33.93 | 94.64 | 91.07 |
| V.6 | 456-484 | 100 | 31.03 | 27.59 | 100 | 100 |
| V.7 | 469-498 | 100 | 56.67 | 60 | 100 | 100 |
| VI | 617-645 | 100 | 75.86 | 93.1 | 100 | 100 |

FIG. 8

| | 3 x 10⁶ rVSV-Ebola pfu | | | 20 x 10⁶ rVSV-Ebola pfu | | | 100 x 10⁶ rVSV-Ebola pfu | | |
|---|---|---|---|---|---|---|---|---|---|
| | A/G | IgM | IgA | A/G | IgM | IgA | A/G | IgM | IgA |
| Phage Titer | 7x10⁵ | 8.8x10⁵ | 7.7x10⁴ | 1.13x10⁶ | 2.56x10⁶ | 1.08x10⁵ | 8.4x10⁵ | 2x10⁶ | 8.8x10⁴ |

FIG. 9

```
                                                            GP1
          10        20        30        40        50        60        70        80
MGVTGILQLPRDRFKRTSFFLWVIILFQRTFSIPLGVIHNSTLQVSDVDKLVCRDKLSSTNQLRSVGLNLEGNGVATDVP
           SP

GP1
          90       100       110       120       130       140       150       160
SATKRWGFRSGVPPKVVNYEAGEWAENCYNLEIKKPDGSECLPAAPDGIRGFPRCRYVHKVSGTGPCAGDFAFHKEGAFF

GP1
         170       180       190       200       210       220       230       240
LYDRLASTVIYRGTTFAEGVVAFLILPQAKKDFFSSHPLREPVNATEDPSSGYYSTTIRYQATGFGTNETEYLFEVDNLT

GP1
         250       260       270       280       290       300       310       320
YVQLESRFTPQFLLQLNETIYTSGKRSNTTGKLIWKVNPEIDTTIGEWAFWETKKNLTRKIRSEELSFTVVSNGAKNISG

GP1
         330       340       350       360       370       380       390       400
QSPARTSSDPGTNTTTEDHKIMASENSSAMVQVHSQGREAAVSHLTTLATISTSPQSLTTKPGPDNSTHNTPVYKLDISE

GP1
         410       420       430       440       450       460       470       480
ATQVEQHHRRTDNDSTASDTPSATTAAGPPKAENTNTSKSTDFLDPATTTSPQNHSETAGNNNTHHQDTGEESASSGKLG

GP1
         490       500       510       520       530       540       550       560
LITNTIAGVAGLITGGRRTRREAIVNAQPKCNPNLHYWTTQDEGAAIGLAWIPYFGPAAEGIYIEGLMHNQDGLICGLRQ
                                                   SP 570       580       590       600       610       620       630       640
LANETTQALQLFLRATTELRTFSILNRKAIDFLLQRWGGTCHILGPDCCIEPHDWTKNITDKIDQIIHDFVDKTLPDQGD
                                                   SP 650       660       670
NDNWWTGWRQWIPAGIGVTGVILAVIALFCICKFVF
                    SP
```

FIG. 10B

```
                        410        420        430        440        450        460        470        480
                ....|....| ....|....| ....|....| ....|....| ....|....| ....|....| ....|....| ....|....|
Mayinga_Strain  ATQVEQHHRR TDNDSTASDT PSATTAAGPP KAENTNTSKS TDFLDPATTT SPQNHSETAG NNNTHHQDTG EESASSGKLG
Kikwit_Strain   .......... .......... .P.......L .........G ..L....... .......... .......... ..........
Makona_Strain   ....G..... A......... .P.......L .......... A.S..L.... ....Y..... .......... ..........

490        500        510        520        530        540        550        560
                ....|....| ....|....| ....|....| ....|....| ....|....| ....|....| ....|....| ....|....|
Mayinga_Strain  LITNTIAGVA GLITGGRRTR REAIVNAQPK CNPNLHYWTT QDEGAAIGLA WIPYFGPAAE GIYIEGLMHN QDGLICGLRQ
Kikwit_Strain   .......... .........A .......... .......... .......... .......... ...T...... ..........
Makona_Strain   .......... .......... ..V....... .......... .......... .......... ...T...... ..........

570        580        590        600        610        620        630        640
                ....|....| ....|....| ....|....| ....|....| ....|....| ....|....| ....|....| ....|....|
Mayinga_Strain  LANETTQALQ LFLRATTELR TFSILNRKAI DFLLQRWGGT CHILGPDCCI EPHDWTKNIT DKIDQIIHDF VDKTLPDQGD
Kikwit_Strain   .......... .......... .......... .......... .......... .......... .......... ..........
Makona_Strain   .......... .......... .......... .......... .......... .......... .......... ..........

650        660        670
                ....|....| ....|....| ....|....| ....|.
Mayinga_Strain  NDNWWTGWRQ WIPAGIGVTG VIIAVIALFC ICKFVF
Kikwit_Strain   .......... .......... .......... ......
Makona_Strain   .......... .......... .......... ......
```

FIG. 11

| | | AA Sequence |
|---|---|---|
| 6D8 | Known site<br>GFPDL | 390-NTPVYKLDISEATQVEQ-406<br>380-TKPGPDNSTHNTPVYKLDISEATQVEQH-407 |
| 13F6 | Known site<br>GFPDL | 402-TQVEQHHRRTDNDSTAS-418<br>402-TQVEQHHRRTDND-414 |

MAb 289

MAb 324

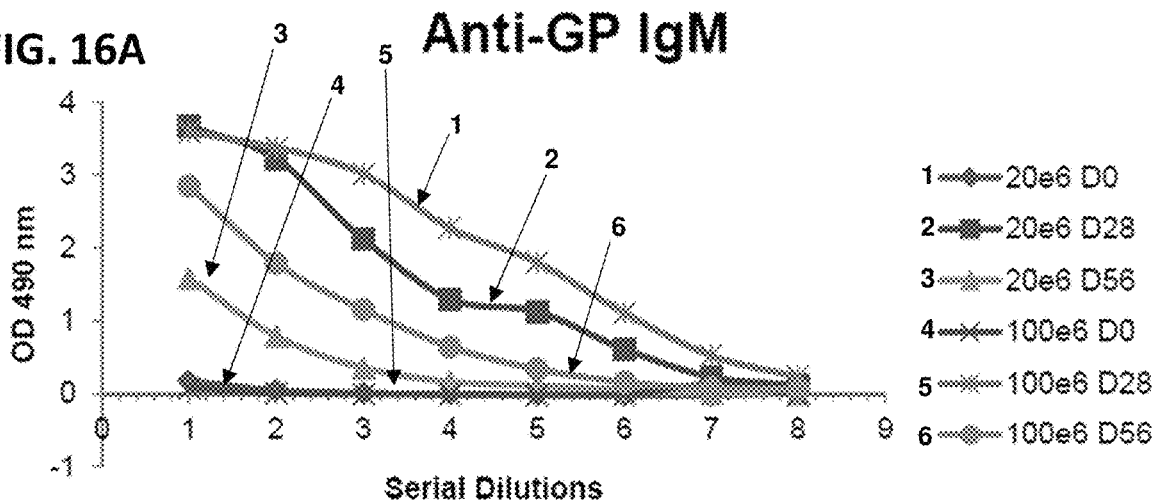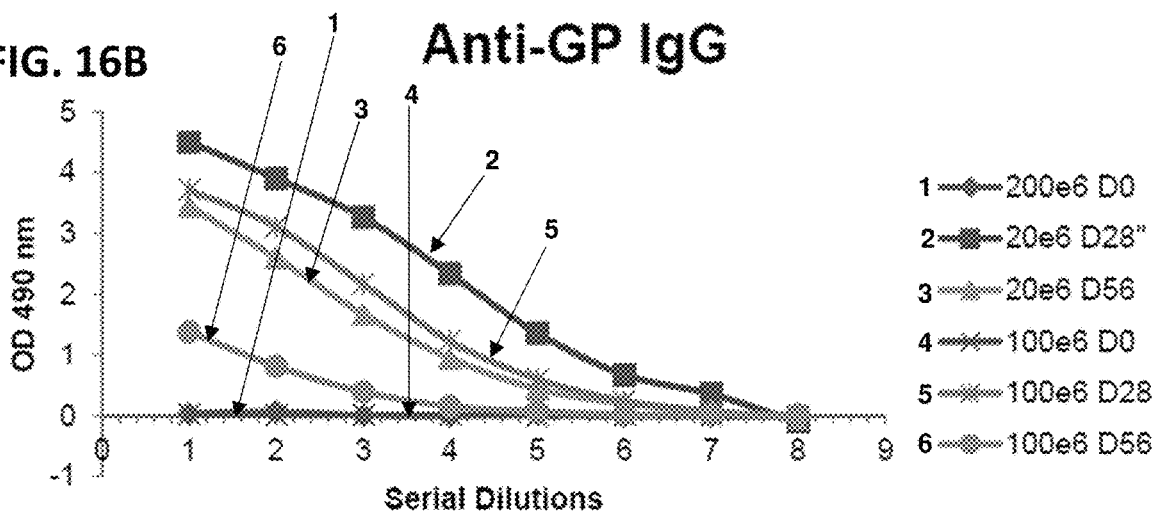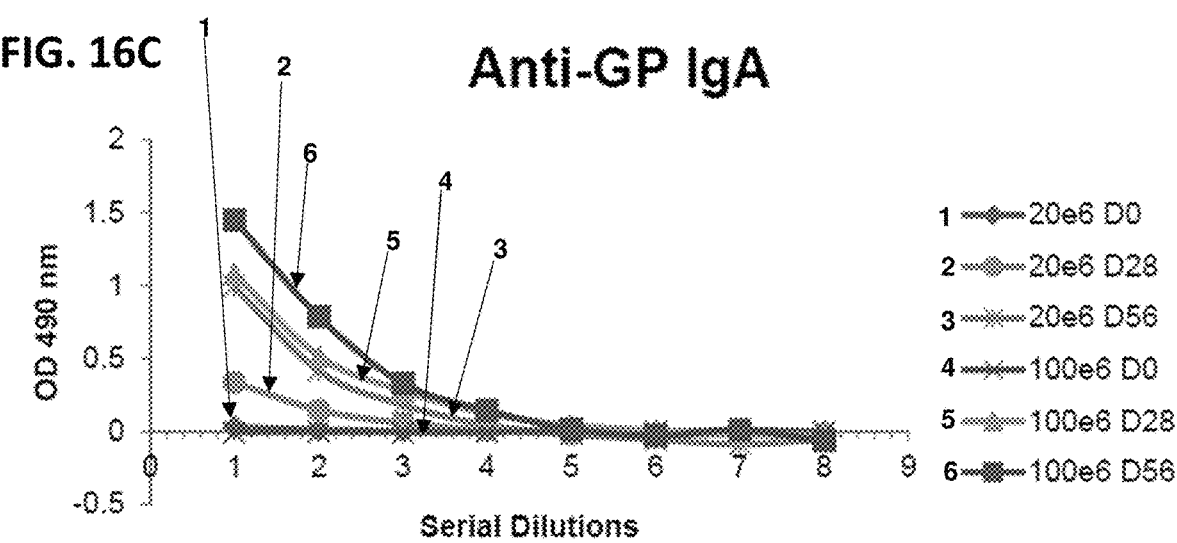

FIG. 18A

|  | 20 x 10⁶ rVSV-Ebola pfu | | | 100 x 10⁶ rVSV-Ebola pfu | | |
|---|---|---|---|---|---|---|
|  | A/G | IgM | IgA | A/G | IgM | IgA |
| Phage Titer | 1x10⁶ | 2.37x10⁶ | 7.6x10⁴ | 8.6x10⁵ | 2.05x10⁷ | 2.7x10⁴ |

FIG. 18B
20 x 10⁶ DOSE

FIG. 18C
100 x 10⁶ DOSE

FIG. 19A

```
                            10         20         30         40         50         60         70         80
                            |          |          |          |          |          |          |          |
Mayinga ebolavirus G    MGVTGILQLP RDRFKRTSFF LWVIILFQRT FSIPLGVIHN STLQVSDVDK LVCRDKLSST NQLRSVGLNL EGNGVATDVP
Kikwit ebolavirus GP    .......... .......... .......... .......... .......... .......... .......... ..........
Makona ebolavirus GP    .......... .......... .......... .......... .......... .......... .......... ..........
Bundibugyo ebolavirus   .VTS...... .E..RK.... V........ .HKV.P.... N.....I... S..K...... .......... ..........
Sudan ebolavirus GP     ..GLSL.... ..K.RKS... V........ .KA..M..VT ....E.TEI.Q ..K.H.A... D..K...... ..S..S..I.
Tai Forest ebolaviru    ..AS...... .E..RK.... V........ .HKV...... ....V..... N.......... ....I..F... S..K...... ..........
Marburg ebolavirus G    ---------- ----MK.TC. .......... .ISL.I.G. .KNL.ILE.AS N--NQPQNVD S..SGT.QK. EDVHLM.FT. S.QK. DSPL 90        100        110        120        130        140        150        160
                            |          |          |          |          |          |          |          |
Mayinga ebolavirus G    SATKRWGFRS GVPPKVVNYE AGEWAENCYN LEIKKPDGSE CLPAAPDGIR GFPRCRYVHK VSGTGPCAGD FAFHKEGAFF
Kikwit ebolavirus GP    .......... .......... .......... .......... .......... .......... .......... ..........
Makona ebolavirus GP    ..V....... .......... .......... .......... .......... .......... .......... ..........
Bundibugyo ebolavirus   T......... ..A....... .......... .......... D..A...... .E..E.V... .......... ..........
Sudan ebolavirus GP     .......... .......S.. .......... .......... ...PP..V.. .......... .......PEG ..........
Tai Forest ebolaviru    T......... ..A....... .......... .......... ....A..V.. ..E..EV... .D..H..... ..Q...P..Y ...D......
Marburg ebolavirus G    E.S...A..T ...NE.T.E. .E.KT..... ISVTD.S.KS L.LDP.TN.. DY.K.KTI.H IQ.QN.H.QG I.L.LW....

170        180        190        200        210        220        230        240
                            |          |          |          |          |          |          |          |
Mayinga ebolavirus G    LYDRLASTVI YRGTTFAEGV VAFLILPQAK KDFFSSHPLR EPVNATEDPS SGYYSTTIRY QATGFGTNET EYLFEVDNLT
Kikwit ebolavirus GP    .......I.. ..S..S.... .......... ....RT.... ...Q.P..H ..A.M.T... Y.HTV.LN.. V.DN....M. NF..Q..H.
Makona ebolavirus GP    .......... ...VM..... ....I..... .AKP.ET.LQ.P.I. .A..Y..NT. Y.ATSYLE.. EIEN..AQHS TT..KI..M.
Bundibugyo ebolavirus   .......I.. .......... .......... ....K.R... ...Q.P..H ..A.M.T... Y.HT...N.. VVDN....T. .F..Q..H.
Sudan ebolavirus GP     ...I...TM .KV.T..N I.AM.VNKTV HRMIF.RQGQ GYRHMMLTST NK.WTSSNGT .TN--D.GCF GA.Q.YNSTK
Tai Forest ebolaviru
Marburg ebolavirus G
```

```
                        490        500        510        520        530        540        550        560
                        |....|....|....|....|....|....|....|....|....|....|....|....|....|....|....|....|
Mayinga ebolavirus G    LGLITNTIAG VAGLITGGRR TRREAIVNA- ---------- ---------Q PKCNPNLHYW TTQDEGAAIG LAWIPYFGPA
Kikwit ebolavirus GP    .......... .......... ....A..... ---------- ---------- .......... .......... ..........
Makona ebolavirus GP    .......... .......... .......V.. ---------- ---------- .......... .......... ..........
Bundibugyo ebolavirus GP P..L......R ....N.L..S ....ITLRT- ---------- ---------- ........A. .......... ..........
Sudan ebolavirus GP     -....S.VT. IL.SLGLRK. S..QTNTK.- ---------- ---------- -------T.G .A.EQHM.A. I........G
Tai Forest ebolavirus   P.FL.....R .TN.L..S.. K..DVTP.T- ---------- ---------- .......... ...AL..... ..........
Marburg ebolavirus G    PVPN.K..FD ESSSSGASAE EDQH.SP.IS LTLSYEPNIN ENTAYSSENE ND.DAE.RI. SV.EDDL.A. .S...F...G 570        580        590        600        610        620        630        640
                        |....|....|....|....|....|....|....|....|....|....|....|....|....|....|....|....|
Mayinga ebolavirus G    AEGIYIEGLM HRQDGLICGL RQLANETTQA LQLFLRATTE LRTFSILNRK AIDFLLQRWG GTCHILGPDC CIEPHDWTKN
Kikwit ebolavirus GP    .T........ .......... .......... .......... .......... .......... .......... ..........
Makona ebolavirus GP    .T........ .......... .......... .......... .......... .......... .......... ..........
Bundibugyo ebolavirus GP .T.I...... ....N..... .......... .......V.. .......... .......... .......... ..........
Sudan ebolavirus GP     .T........ ...NA.V... .......... .......... .....YT... .......R.. .......... ........Q.
Tai Forest ebolavirus   .T.I...... ....E..N.. .......... .......I.. .......... .......... .......... ..........
Marburg ebolavirus G    I..L.TAV.I K..NN.V.R. .......R.. .Q.AKS..E. .L.V...LI. H........T .......KV. .GIE.LS...

650        660        670        680        690        700
                        |....|....|....|....|....|....|....|....|....|....|....|....|
Mayinga ebolavirus G    ITDKIDQIIH DFVDKTLPDQ GDMDNWWTGW RQWIPAGIGV TGVIAVIAL FCICKFVF---  ---
Kikwit ebolavirus GP    .......... .......... .......... .......... ...V...... ..........   ---
Makona ebolavirus GP    .......... ....I.P... T......... .......... .....I.... .....L..LL--  ---
Bundibugyo ebolavirus GP .......... ....I.NP.N .DND...... .......... .......I.. .....L.V.LLC--  ---
Sudan ebolavirus GP     .......N.. .......... .......... .......... .I......I. ........I.   ---
Tai Forest ebolavirus   .......... ....NN..N. N.GS...... K..V...... .I........ ....ML---    ---
Marburg ebolavirus G    ..KK .EQKEGTGWG LGGKW.TSD. GVLTML..LL LLS.AVL... .S..RIFTKY IG
                        .SEQ
```

FIG. 20

| Site | SEQ ID NO: 35 AA | Sequence |
|---|---|---|
| I | 1-36 | MGYTGILQLPRDRFKRTSFFLWVIILFQRTFSIPLG |
| II | 32-273 | SIPLGVIHNSTLQVSDVDKLVCRDKLSSTNQLRSVGLNLEGNGVATDVPSATKRWGFRSGVPPKVVNYEAGEWAENCYNLEIKKPDGSECLPAAPDGIRGFPRCRYVHKVSGTGPCAGDFAFHKEGAFFLYDRLASTVIYRGTTFAEGVVAFLILPQAKKDFFSSHPLREPVNATEDPSSGYYSTTIRYQATGFGTNETEYLFEVDNLTYVQLESRFTPQFLLQLNETIYTSGKRSNTTGKL |
| II.1 | 152-220 | AFHKEGAFFLYDRLASTVIYRGTTFAEGVVAFLILPQAKKDFFSSHPLREPVNATEDPSSGYYSTTIRY |
| II.2 | 195-226 | SSHPLREPVNATEDPSSGYYSTTIRYQATGFG |
| II.3 | 134-141 | RCRYVHKV |
| III | 205-366 | ATEDPSSGYYSTTIRYQATGFGTNETEYLFEVDNLTYVQLESRFTPQFLLQLNETIYTSGKRSNTTGKLIWKVNPEIDTTIGEWAFWETKKNLTRKIRSEELSFTVVSNGAKNISGQSPARTSSDPGTNTTTEDHKIMASENSSAMVQVHS |
| III.1 | 210-220 | SSGYYSTTIRY |
| III.2 | 226-253 | GTNETEYLFEVDNLTYVQLESRFTPQFL |
| IV | 267-419 | SNTTGKLIWKVNPEIDTTIGEWAFWETKKNLTRKIRSEELSFTVVSNGAKNISGQSPARTSSDPGTNTTTEDHKIMASENSSAMVQVHSQGREAAVSHLTTLATISTSPQSLTTKPGPDNSTHNTPVYKLDISEATQVEQHHRRTDNDSTASD |
| IV.1 | 282-305 | DTTIGEWAFWETKKNLTRKIRSEE |
| IV.2 | 286-296 | GEWAFWETKKN |
| IV.3 | 286-364 | GEWAFWETKKNLTRKIRSEELSFTVVSNGAKNISGQSPARTSSDPGTNTTTEDHKIMASENSSAMVQVHSQGREAAVSH |
| IV.4 | 319-334 | SGQSPARTSSDPGTNT |
| IV.5 | 336-414 | TSSDPGTNTTTEDHKIMASENSSAMVQVHSQGREAAVSHLTTLATISTSPQSLTTKPGPDNSTHNTPVYKLDISEATQVEQHHRRTDND |
| V | 335-582 | TEDHKIMASENSSAMVQVHSQGREAAVSHLTTLATISTSPQSLTTKPGPDNSTHNTPVYKLDISEATQVEQHHRRTDNDSTASDTPSATTAAGPPKAENTNTSKSTDFLDPATTTSPQNHSETAGNNNTHHQDTGEESASSGKLGLITNTIAGVAGLITGGRRTRREAIVNAQPKCNPNLHYWTTQDEGAAIGLAWIPYFGPAAEGIYIEGLMHNQDGLICGLRQLANETTQALQLFLRATTELRTF |
| V.1 | 343-368 | ASENSSAMVQVHSQGREAAVSHLTTL |
| V.2 | 372-420 | STSPQSLTTKPGPDNSTHNTPVYKLDISEATQVEQHHRRTDNDSTASDT |
| V.3 | 380-491 | TKPGPDNSTHNTPVYKLDISEATQVEQHHRRTDNDSTASDTPSATTAAGPPKAENTNTSKSTDFLDPATTTSPQNHSETAGNNNTHHQDTGEESASSGKLGLITNTIAGVAG |
| V.4 | 424-447 | TTAAGPPKAENTNTSKSTDFLDPA |
| V.5 | 436-491 | NTSKSTDFLDPATTTSPQNHSETAGNNNTHHQDTGEESASSGKLGLITNTIAGVAG |
| V.6 | 456-484 | SETAGNNNTHHQDTGEESASSGKLGLITN |
| V.7 | 469-498 | TGEESASSGKLGLITNTIAGVAGLITGGRR |
| V.8 | 367-378 | TLATISTSPQSL |
| V.9 | 394-406 | YKLDISEATQVEQ |
| V.10 | 520-547 | TQDEGAAIGLAWIPYFGPAAEGIYIEGL |
| V.11 | 585-599 | LNRKAIDFLLQRWGG |
| VI | 617-645 | KNITDKIDQIIHDFVDKTLPDQGDNDNWW |

FIG. 21

Rabbit immunization of GP antigenic site peptides induces high antibody binding to homologous and heterologous native GP

FIG. 22

Conserved antigenic sites in GP1 induce neutralizing antibodies

Rabbit sera Neut titers
PsVN - Mayinga

| GP 282-305 | GP 343-368 | GP 520-547 |
|---|---|---|
| ~60 | ~80 | ~90 |

(IC50 titers)

FIG. 23

Zaire ebolavirus challenge study in mice

| | Group | Dose | Emulsigen (1:1) | N |
|---|---|---|---|---|
| SEQ ID NO: 17 | IV.1 (GP 282-305) | 20 ug | + | 10 |
| SEQ ID NO: 21 | V.1 (GP 343-368) | 20 ug | + | 10 |
| SEQ ID NO: 3 | V.7 (GP 469-498) | 20 ug | + | 10 |
| SEQ ID NO: 29 | V.10 (GP 520-547) | 20 ug | + | 10 |
| SEQ ID NO: 10 | VI (GP 617-645) | 20 ug | + | 10 |
| 17, 21, 3, 29, 10 | Mix peptide | 20 ug | + | 10 |
| | KLH | 20 ug | + | 10 |
| | EBOV GP - VEEV replicon particle (VRP) | | - | 10 |
| | Naive | | - | 10 |

Immunization with peptides from Antigenic sites V.7 in GP1 and VI in GP2 induces sterilizing immunity

- IV.1 (GP 282-305)
- V.1 (GP 343-368)
- V.7 (GP 469-498)
- V.10 (GP 520-547)
- VI (GP 617-645)
- Mix (Peptides)
- KLH
- EBOV GP VRP
- Naive

FIG. 24

Conserved antigenic sites in V.7 in GP1 and VI.1 in GP2 provide significant protection from weight loss following Zaire ebolavirus challenge 1. IV.1 (GP 282-305)
2. V.1 (GP 343-368)
3. V.7 (GP 469-498)
4. V.10 (GP 520-647)
5. VI (GP 617-645)
6. Mix (Peptides)
7. KLH
8. EBOV GP VRP
9. Naive

FIG. 25

Conserved antigenic sites in C-ter of GP1 and GP2
generate strong binding antibodies
to both Mayinga and Makona GP in SPR

FIG. 26

Convalescent Sera shows higher antibody binding to diverse antigenic sites in GP than post-vaccination sera

FIG. 27

Identification of GP antigenic sites that
strongly correlate with Ebola neutralization titers (PsVN)

GP 457-484, $R^2 = 0.9836$ (Max RU vs PsVN 50 titers)

GP 469-498, $R^2 = 0.935$

GP 520-547, $R^2 = 0.713$

GP 617-645, $R^2 = 0.6347$

PsVN 50 titers

FIG. 28

Spatial structure of linear neutralizing
and protective antigenic sites in GP

SEQUENCE LISTING

```
<160> NUMBER OF SEQ ID NOS: 62

<210> SEQ ID NO 1
<211> LENGTH: 30
<212> TYPE: PRT
<213> ORGANISM: Ebola virus

<400> SEQUENCE: 1

Thr Thr Glu Asp His Lys Ile Met Ala Ser Glu Asn Ser Ser Ala Met
1               5                   10                  15

Val Gln Val His Ser Gln Gly Arg Glu Ala Ala Val Ser His
            20                  25                  30

<210> SEQ ID NO 2
<211> LENGTH: 28
<212> TYPE: PRT
<213> ORGANISM: Ebola virus

<400> SEQUENCE: 2

Glu Thr Ala Gly Asn Asn Asn Thr His His Gln Asp Thr Gly Glu Glu
1               5                   10                  15

Ser Ala Ser Ser Gly Lys Leu Gly Leu Ile Thr Asn
            20                  25

<210> SEQ ID NO 3
<211> LENGTH: 30
<212> TYPE: PRT
<213> ORGANISM: Ebola virus

<400> SEQUENCE: 3

Thr Gly Glu Glu Ser Ala Ser Ser Gly Lys Leu Gly Leu Ile Thr Asn
1               5                   10                  15

Thr Ile Ala Gly Val Ala Gly Leu Ile Thr Gly Gly Arg Arg
            20                  25                  30

<210> SEQ ID NO 4
<211> LENGTH: 30
```

```
<212> TYPE: PRT
<213> ORGANISM: Ebola virus

<400> SEQUENCE: 4

Lys Asn Ile Thr Asp Lys Ile Asp Gln Ile Ile His Asp Phe Val Asp
1               5                   10                  15

Lys Thr Leu Pro Asp Gln Gly Asp Asn Asp Asn Trp Trp Thr
            20                  25                  30

<210> SEQ ID NO 5
<211> LENGTH: 17
<212> TYPE: PRT
<213> ORGANISM: Ebola virus

<400> SEQUENCE: 5

Phe Val Asp Lys Thr Leu Pro Asp Gln Gly Asp Asn Asp Asn Trp Trp
1               5                   10                  15

Thr

<210> SEQ ID NO 6
<211> LENGTH: 18
<212> TYPE: PRT
<213> ORGANISM: Ebola virus
<220> FEATURE:
<221> NAME/KEY: misc_feature
<222> LOCATION: (2)..(2)
<223> OTHER INFORMATION: Xaa is V or I
<220> FEATURE:
<221> NAME/KEY: misc_feature
<222> LOCATION: (4)..(4)
<223> OTHER INFORMATION: Xaa is K or N
<220> FEATURE:
<221> NAME/KEY: misc_feature
<222> LOCATION: (5)..(5)
<223> OTHER INFORMATION: Xaa is T, P, or N
<220> FEATURE:
<221> NAME/KEY: misc_feature
<222> LOCATION: (9)..(9)
<223> OTHER INFORMATION: Xaa is D or N
<220> FEATURE:
<221> NAME/KEY: misc_feature
<222> LOCATION: (11)..(11)
<223> OTHER INFORMATION: Xaa is G, T, D, or N
<220> FEATURE:
<221> NAME/KEY: misc_feature
<222> LOCATION: (12)..(12)
<223> OTHER INFORMATION: Xaa  is D or N
<220> FEATURE:
<221> NAME/KEY: misc_feature
<222> LOCATION: (13)..(13)
<223> OTHER INFORMATION: Xaa is N, D, or G
<220> FEATURE:
<221> NAME/KEY: misc_feature
<222> LOCATION: (14)..(14)
<223> OTHER INFORMATION: Xaa is D or S

<400> SEQUENCE: 6

Phe Xaa Asp Xaa Xaa Thr Leu Pro Xaa Gln Xaa Xaa Xaa Xaa Asn Trp
1               5                   10                  15

Trp Thr

<210> SEQ ID NO 7
<211> LENGTH: 31
<212> TYPE: PRT
<213> ORGANISM: Ebola virus
<220> FEATURE:
<221> NAME/KEY: misc_feature
<222> LOCATION: (8)..(8)
<223> OTHER INFORMATION: Xaa  is D or N
<220> FEATURE:
```

```
<221> NAME/KEY: misc_feature
<222> LOCATION: (15)..(15)
<223> OTHER INFORMATION: Xaa is V or I
<220> FEATURE:
<221> NAME/KEY: misc_feature
<222> LOCATION: (17)..(17)
<223> OTHER INFORMATION: Xaa is K or N
<220> FEATURE:
<221> NAME/KEY: misc_feature
<222> LOCATION: (18)..(18)
<223> OTHER INFORMATION: Xaa is T, P, or N
<220> FEATURE:
<221> NAME/KEY: misc_feature
<222> LOCATION: (22)..(22)
<223> OTHER INFORMATION: Xaa is D or N
<220> FEATURE:
<221> NAME/KEY: misc_feature
<222> LOCATION: (24)..(24)
<223> OTHER INFORMATION: Xaa is G, T, D, or N
<220> FEATURE:
<221> NAME/KEY: misc_feature
<222> LOCATION: (25)..(25)
<223> OTHER INFORMATION: Xaa is D or N
<220> FEATURE:
<221> NAME/KEY: misc_feature
<222> LOCATION: (26)..(26)
<223> OTHER INFORMATION: Xaa is N, D, or G
<220> FEATURE:
<221> NAME/KEY: misc_feature
<222> LOCATION: (27)..(27)
<223> OTHER INFORMATION: Xaa is D or S

<400> SEQUENCE: 7

Lys Asn Ile Thr Asp Lys Ile Xaa Gln Ile Ile His Asp Phe Xaa Asp
1               5                   10                  15

Xaa Xaa Thr Leu Pro Xaa Gln Xaa Xaa Xaa Xaa Asn Trp Trp Thr
            20                  25                  30

<210> SEQ ID NO 8
<211> LENGTH: 30
<212> TYPE: PRT
<213> ORGANISM: Ebola virus
<220> FEATURE:
<221> NAME/KEY: misc_feature
<222> LOCATION: (2)..(2)
<223> OTHER INFORMATION: Xaa is T or N
<220> FEATURE:
<221> NAME/KEY: misc_feature
<222> LOCATION: (25)..(25)
<223> OTHER INFORMATION: Xaa is E or K

<400> SEQUENCE: 8

Thr Xaa Glu Asp His Lys Ile Met Ala Ser Glu Asn Ser Ser Ala Met
1               5                   10                  15

Val Gln Val His Ser Gln Gly Arg Xaa Ala Ala Val Ser His
            20                  25                  30

<210> SEQ ID NO 9
<211> LENGTH: 30
<212> TYPE: PRT
<213> ORGANISM: Ebola virus
<220> FEATURE:
<221> NAME/KEY: misc_feature
<222> LOCATION: (8)..(8)
<223> OTHER INFORMATION: Xaa is D or N
<220> FEATURE:
<221> NAME/KEY: misc_feature
<222> LOCATION: (15)..(15)
<223> OTHER INFORMATION: Xaa is V or I
<220> FEATURE:
<221> NAME/KEY: misc_feature
<222> LOCATION: (17)..(17)
<223> OTHER INFORMATION: Xaa is K or N
```

```
<220> FEATURE:
<221> NAME/KEY: misc_feature
<222> LOCATION: (18)..(18)
<223> OTHER INFORMATION: Xaa is T, P, or N
<220> FEATURE:
<221> NAME/KEY: misc_feature
<222> LOCATION: (22)..(22)
<223> OTHER INFORMATION: Xaa is D or N
<220> FEATURE:
<221> NAME/KEY: misc_feature
<222> LOCATION: (24)..(24)
<223> OTHER INFORMATION: Xaa is G, T, D, or N
<220> FEATURE:
<221> NAME/KEY: misc_feature
<222> LOCATION: (25)..(25)
<223> OTHER INFORMATION: Xaa is D or N
<220> FEATURE:
<221> NAME/KEY: misc_feature
<222> LOCATION: (26)..(26)
<223> OTHER INFORMATION: Xaa is N, D, or G
<220> FEATURE:
<221> NAME/KEY: misc_feature
<222> LOCATION: (27)..(27)
<223> OTHER INFORMATION: Xaa is D or S

<400> SEQUENCE: 9

Lys Asn Ile Thr Asp Lys Ile Xaa Gln Ile Ile His Asp Phe Xaa Asp
1               5                   10                  15

Xaa Xaa Thr Leu Pro Xaa Gln Xaa Xaa Xaa Xaa Asn Trp Trp
            20                  25                  30

<210> SEQ ID NO 10
<211> LENGTH: 29
<212> TYPE: PRT
<213> ORGANISM: Ebola virus

<400> SEQUENCE: 10

Lys Asn Ile Thr Asp Lys Ile Asp Gln Ile Ile His Asp Phe Val Asp
1               5                   10                  15

Lys Thr Leu Pro Asp Gln Gly Asp Asn Asp Asn Trp Trp
            20                  25

<210> SEQ ID NO 11
<211> LENGTH: 29
<212> TYPE: PRT
<213> ORGANISM: Ebola virus

<400> SEQUENCE: 11

Lys Asn Ile Thr Asp Lys Ile Asn Gln Ile Ile His Asp Phe Ile Asp
1               5                   10                  15

Lys Pro Leu Pro Asp Gln Thr Asp Asn Asp Asn Trp Trp
            20                  25

<210> SEQ ID NO 12
<211> LENGTH: 29
<212> TYPE: PRT
<213> ORGANISM: Ebola virus

<400> SEQUENCE: 12

Lys Asn Ile Thr Asp Lys Ile Asp Gln Ile Ile His Asp Phe Ile Asp
1               5                   10                  15

Asn Pro Leu Pro Asn Gln Asp Asn Asp Asp Asn Trp Trp
            20                  25

<210> SEQ ID NO 13
<211> LENGTH: 29
<212> TYPE: PRT
```

```
<213> ORGANISM: Ebola virus

<400> SEQUENCE: 13

Lys Asn Ile Thr Asp Lys Ile Asn Gln Ile Ile His Asp Phe Val Asp
1               5                   10                  15

Asn Asn Leu Pro Asn Gln Asn Asp Gly Ser Asn Trp Trp
            20                  25

<210> SEQ ID NO 14
<211> LENGTH: 30
<212> TYPE: PRT
<213> ORGANISM: Ebola virus

<400> SEQUENCE: 14

Lys Asn Ile Thr Asp Lys Ile Asn Gln Ile Ile His Asp Phe Ile Asp
1               5                   10                  15

Lys Pro Leu Pro Asp Gln Thr Asp Asn Asp Asn Trp Trp Thr
            20                  25                  30

<210> SEQ ID NO 15
<211> LENGTH: 30
<212> TYPE: PRT
<213> ORGANISM: Ebola virus

<400> SEQUENCE: 15

Lys Asn Ile Thr Asp Lys Ile Asp Gln Ile Ile His Asp Phe Ile Asp
1               5                   10                  15

Asn Pro Leu Pro Asn Gln Asp Asn Asp Asp Asn Trp Trp Thr
            20                  25                  30

<210> SEQ ID NO 16
<211> LENGTH: 30
<212> TYPE: PRT
<213> ORGANISM: Ebola virus

<400> SEQUENCE: 16

Lys Asn Ile Thr Asp Lys Ile Asn Gln Ile Ile His Asp Phe Val Asp
1               5                   10                  15

Asn Asn Leu Pro Asn Gln Asn Asp Gly Ser Asn Trp Trp Thr
            20                  25                  30

<210> SEQ ID NO 17
<211> LENGTH: 24
<212> TYPE: PRT
<213> ORGANISM: Ebola virus

<400> SEQUENCE: 17

Asp Thr Thr Ile Gly Glu Trp Ala Phe Trp Glu Thr Lys Lys Asn Leu
1               5                   10                  15

Thr Arg Lys Ile Arg Ser Glu Glu
            20

<210> SEQ ID NO 18
<211> LENGTH: 24
<212> TYPE: PRT
<213> ORGANISM: Ebola virus

<400> SEQUENCE: 18

Asp Thr Gly Val Gly Glu Trp Ala Phe Trp Glu Asn Lys Lys Asn Phe
1               5                   10                  15

Thr Lys Thr Leu Ser Ser Glu Glu
            20
```

```
<210> SEQ ID NO 19
<211> LENGTH: 24
<212> TYPE: PRT
<213> ORGANISM: Ebola virus

<400> SEQUENCE: 19

Asn Ala Asp Ile Gly Glu Trp Ala Phe Trp Glu Asn Lys Lys Asn Leu
1               5                   10                  15

Ser Glu Gln Leu Arg Gly Glu Glu
            20

<210> SEQ ID NO 20
<211> LENGTH: 24
<212> TYPE: PRT
<213> ORGANISM: Ebola virus

<400> SEQUENCE: 20

Asp Thr Ser Met Gly Glu Trp Ala Phe Trp Glu Asn Lys Lys Asn Phe
1               5                   10                  15

Lys Lys Thr Leu Ser Ser Glu Glu
            20

<210> SEQ ID NO 21
<211> LENGTH: 26
<212> TYPE: PRT
<213> ORGANISM: Ebola virus

<400> SEQUENCE: 21

Ala Ser Glu Asn Ser Ser Ala Met Val Gln Val His Ser Gln Gly Arg
1               5                   10                  15

Glu Ala Ala Val Ser His Leu Thr Thr Leu
            20                  25

<210> SEQ ID NO 22
<211> LENGTH: 26
<212> TYPE: PRT
<213> ORGANISM: Ebola virus

<400> SEQUENCE: 22

Ala Ser Glu Asn Ser Ser Ala Met Val Gln Val His Ser Gln Gly Arg
1               5                   10                  15

Lys Ala Ala Val Ser His Leu Thr Thr Leu
            20                  25

<210> SEQ ID NO 23
<211> LENGTH: 24
<212> TYPE: PRT
<213> ORGANISM: Ebola virus

<400> SEQUENCE: 23

Val Pro Lys Asp Pro Ala Ser Val Val Gln Val Arg Asp Leu Gln Arg
1               5                   10                  15

Glu Asn Thr Val Pro Thr Ser Pro
            20

<210> SEQ ID NO 24
<211> LENGTH: 26
<212> TYPE: PRT
<213> ORGANISM: Ebola virus

<400> SEQUENCE: 24
```

```
Val Pro Lys Asn Ser Pro Gly Val Val Pro Leu His Ile Pro Glu Gly
1               5                   10                  15

Glu Thr Thr Leu Pro Ser Gln Asn Ser Thr
            20                  25
```

<210> SEQ ID NO 25
<211> LENGTH: 24
<212> TYPE: PRT
<213> ORGANISM: Ebola virus

<400> SEQUENCE: 25

```
Val Ser Glu Asp Ser Thr Pro Val Val Gln Met Gln Asn Ile Lys Gly
1               5                   10                  15

Lys Asp Thr Met Pro Thr Thr Val
            20
```

<210> SEQ ID NO 26
<211> LENGTH: 28
<212> TYPE: PRT
<213> ORGANISM: Ebola virus

<400> SEQUENCE: 26

```
Met Ile Thr Ser His Asp Thr Asp Ser Asn Arg Pro Asn Pro Ile Asp
1               5                   10                  15

Ile Ser Glu Ser Thr Glu Pro Gly Leu Leu Thr Asn
            20                  25
```

<210> SEQ ID NO 27
<211> LENGTH: 27
<212> TYPE: PRT
<213> ORGANISM: Ebola virus

<400> SEQUENCE: 27

```
Leu Thr Thr Pro Glu Asn Ile Thr Thr Ala Val Lys Thr Val Leu Pro
1               5                   10                  15

Gln Glu Ser Thr Ser Asn Gly Leu Ile Thr Ser
            20                  25
```

<210> SEQ ID NO 28
<211> LENGTH: 28
<212> TYPE: PRT
<213> ORGANISM: Ebola virus

<400> SEQUENCE: 28

```
Leu Pro Glu Gln His Thr Ala Ala Ser Ala Ile Pro Arg Ala Val His
1               5                   10                  15

Pro Asp Glu Leu Ser Gly Pro Gly Phe Leu Thr Asn
            20                  25
```

<210> SEQ ID NO 29
<211> LENGTH: 28
<212> TYPE: PRT
<213> ORGANISM: Ebola virus

<400> SEQUENCE: 29

```
Thr Gln Asp Glu Gly Ala Ala Ile Gly Leu Ala Trp Ile Pro Tyr Phe
1               5                   10                  15

Gly Pro Ala Ala Glu Gly Ile Tyr Ile Glu Gly Leu
            20                  25
```

<210> SEQ ID NO 30
<211> LENGTH: 28

```
<212> TYPE: PRT
<213> ORGANISM: Ebola virus

<400> SEQUENCE: 30

Thr Gln Asp Glu Gly Ala Ala Ile Gly Leu Ala Trp Ile Pro Tyr Phe
1               5                   10                  15

Gly Pro Ala Ala Glu Gly Ile Tyr Thr Glu Gly Leu
            20                  25

<210> SEQ ID NO 31
<211> LENGTH: 28
<212> TYPE: PRT
<213> ORGANISM: Ebola virus

<400> SEQUENCE: 31

Thr Gln Asp Glu Gly Ala Ala Ile Gly Leu Ala Trp Ile Pro Tyr Phe
1               5                   10                  15

Gly Pro Ala Ala Glu Gly Ile Tyr Thr Glu Gly Ile
            20                  25

<210> SEQ ID NO 32
<211> LENGTH: 30
<212> TYPE: PRT
<213> ORGANISM: Ebola virus

<400> SEQUENCE: 32

Asn Pro Ile Asp Ile Ser Glu Ser Thr Glu Pro Gly Leu Leu Thr Asn
1               5                   10                  15

Thr Ile Arg Gly Val Ala Asn Leu Leu Thr Gly Ser Arg Arg
            20                  25                  30

<210> SEQ ID NO 33
<211> LENGTH: 29
<212> TYPE: PRT
<213> ORGANISM: Ebola virus

<400> SEQUENCE: 33

Thr Val Leu Pro Gln Glu Ser Thr Ser Asn Gly Leu Ile Thr Ser Thr
1               5                   10                  15

Val Thr Gly Ile Leu Gly Ser Leu Gly Leu Arg Lys Arg
            20                  25

<210> SEQ ID NO 34
<211> LENGTH: 30
<212> TYPE: PRT
<213> ORGANISM: Ebola virus

<400> SEQUENCE: 34

Arg Ala Val His Pro Asp Glu Leu Ser Gly Pro Gly Phe Leu Thr Asn
1               5                   10                  15

Thr Ile Arg Gly Val Thr Asn Leu Leu Thr Gly Ser Arg Arg
            20                  25                  30

<210> SEQ ID NO 35
<211> LENGTH: 676
<212> TYPE: PRT
<213> ORGANISM: Ebola virus

<400> SEQUENCE: 35

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
```

-continued

```
                     20                  25                  30
Ile Pro Leu Gly Val Ile His Asn Ser Thr Leu Gln Val Ser Asp Val
            35                  40                  45
Asp Lys Leu Val Cys Arg Asp Lys Leu Ser Ser Thr Asn Gln Leu Arg
    50                  55                  60
Ser Val Gly Leu Asn Leu Glu Gly Asn Gly Val Ala Thr Asp Val Pro
65                  70                  75                  80
Ser Ala Thr Lys Arg Trp Gly Phe Arg Ser Gly Val Pro Pro Lys Val
                85                  90                  95
Val Asn Tyr Glu Ala Gly Glu Trp Ala Glu Asn Cys Tyr Asn Leu Glu
            100                 105                 110
Ile Lys Lys Pro Asp Gly Ser Glu Cys Leu Pro Ala Ala Pro Asp Gly
        115                 120                 125
Ile Arg Gly Phe Pro Arg Cys Arg Tyr Val His Lys Val Ser Gly Thr
    130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
            180                 185                 190
Phe Phe Ser Ser His Pro Leu Arg Glu Pro Val Asn Ala Thr Glu Asp
        195                 200                 205
Pro Ser Ser Gly Tyr Tyr Ser Thr Thr Ile Arg Tyr Gln Ala Thr Gly
    210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
            260                 265                 270
Leu Ile Trp Lys Val Asn Pro Glu Ile Asp Thr Thr Ile Gly Glu Trp
        275                 280                 285
Ala Phe Trp Glu Thr Lys Lys Asn Leu Thr Arg Lys Ile Arg Ser Glu
    290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
            340                 345                 350
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
    370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Ser Ala Thr Thr Ala Ala Gly Pro Pro Lys Ala
            420                 425                 430
Glu Asn Thr Asn Thr Ser Lys Ser Thr Asp Phe Leu Asp Pro Ala Thr
        435                 440                 445
```

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Ala Ile Val Asn Ala Gln Pro Lys Cys Asn
        500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
        580                 585                 590

Leu Leu Gln Arg Trp Gly Gly Thr Cys His Ile Leu Gly Pro Asp Cys
    595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
        660                 665                 670

Lys Phe Val Phe
    675

<210> SEQ ID NO 36
<211> LENGTH: 676
<212> TYPE: PRT
<213> ORGANISM: Ebola virus

<400> SEQUENCE: 36

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
            85                  90                  95

Val Asn Tyr Glu Ala Gly Glu Trp Ala Glu Asn Cys Tyr Asn Leu Glu
        100                 105                 110

Ile Lys Lys Pro Asp Gly Ser Glu Cys Leu Pro Ala Ala Pro Asp Gly
    115                 120                 125

Ile Arg Gly Phe Pro Arg Cys Arg Tyr Val His Lys Val Ser Gly Thr

-continued

```
            130                 135                 140
Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190

Phe Phe Ser Ser His Pro Leu Arg Glu Pro Val Asn Ala Thr Glu Asp
                195                 200                 205

Pro Ser Ser Gly Tyr Tyr Ser Thr Thr Ile Arg Tyr Gln Ala Thr Gly
                210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
                275                 280                 285

Ala Phe Trp Glu Thr Lys Lys Asn Leu Thr Arg Lys Ile Arg Ser Glu
290                 295                 300

Glu Leu Ser Phe Thr Ala Val Ser Asn Arg Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
                355                 360                 365

Ala Thr Ile Ser Thr Ser Pro Gln Pro Pro Thr Thr Lys Pro Gly Pro
                370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Pro Ala Thr Thr Ala Ala Gly Pro Leu Lys Ala
                420                 425                 430

Glu Asn Thr Asn Thr Ser Lys Gly Thr Asp Leu Leu Asp Pro Ala Thr
                435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Ala Arg Arg Glu Ala Ile Val Asn Ala Gln Pro Lys Cys Asn
                500                 505                 510

Pro Asn Leu His Tyr Trp Thr Thr Gln Asp Glu Gly Ala Ala Ile Gly
                515                 520                 525

Leu Ala Trp Ile Pro Tyr Phe Gly Pro Ala Ala Glu Gly Ile Tyr Thr
                530                 535                 540

Glu Gly Leu Met His Asn Gln Asp Gly Leu Ile Cys Gly Leu Arg Gln
545                 550                 555                 560
```

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
        610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
        675

<210> SEQ ID NO 37
<211> LENGTH: 676
<212> TYPE: PRT
<213> ORGANISM: Ebola virus

<400> SEQUENCE: 37

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
                35                  40                  45

Asp Lys Leu Val Cys Arg Asp Lys Leu Ser Ser Thr Asn Gln Leu Arg
            50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
                100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
            210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu

```
                    245                 250                 255
Asn Glu Thr Ile Tyr Ala Ser Gly Lys Arg Ser Asn Thr Thr Gly Lys
                260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
        290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
                340                 345                 350

Val His Ser Gln Gly Arg Lys Ala Ala Val Ser His Leu Thr Thr Leu
            355                 360                 365

Ala Thr Ile Ser Thr Ser Pro Gln Pro Pro Thr Thr Lys Thr Gly Pro
        370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
        530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670
```

Lys Phe Val Phe
         675

<210> SEQ ID NO 38
<211> LENGTH: 676
<212> TYPE: PRT
<213> ORGANISM: Ebola virus

<400> SEQUENCE: 38

Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
            20                  25                  30

Ile Pro Leu Gly Val Val His Asn Asn Thr Leu Gln Val Ser Asp Ile
        35                  40                  45

Asp Lys Leu Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
        115                 120                 125

Val Arg Gly Phe Pro Arg Cys Arg Tyr Val His Lys Val Ser Gly Thr
    130                 135                 140

Gly Pro Cys Pro Glu Gly Phe Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Lys Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
    210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
            260                 265                 270

Leu Ile Trp Lys Val Asn Pro Thr Val Asp Thr Gly Val Gly Glu Trp
        275                 280                 285

Ala Phe Trp Glu Asn Lys Lys Asn Phe Thr Lys Thr Leu Ser Ser Glu
    290                 295                 300

Glu Leu Ser Val Ile Leu Val Pro Arg Ala Gln Asp Pro Gly Ser Asn
305                 310                 315                 320

Gln Lys Thr Lys Val Thr Pro Thr Ser Phe Ala Asn Asn Gln Thr Ser
                325                 330                 335

Lys Asn His Glu Asp Leu Val Pro Lys Asp Pro Ala Ser Val Val Gln
            340                 345                 350

Val Arg Asp Leu Gln Arg Glu Asn Thr Val Pro Thr Ser Pro Leu Asn

```
                355                 360                 365
Thr Val Pro Thr Thr Leu Ile Pro Asp Thr Met Glu Glu Gln Thr Thr
370                 375                 380

Ser His Tyr Glu Leu Pro Asn Ile Ser Gly Asn His Gln Glu Arg Asn
385                 390                 395                 400

Asn Thr Ala His Pro Glu Thr Leu Ala Asn Asn Pro Pro Asp Asn Thr
                405                 410                 415

Thr Pro Ser Thr Pro Pro Gln Asp Gly Glu Arg Thr Ser Ser His Thr
            420                 425                 430

Thr Pro Ser Pro Arg Pro Val Pro Thr Ser Thr Ile His Pro Thr Thr
        435                 440                 445

Arg Glu Thr Gln Ile Pro Thr Thr Met Ile Thr Ser His Asp Thr Asp
    450                 455                 460

Ser Asn Arg Pro Asn Pro Ile Asp Ile Ser Glu Ser Thr Glu Pro Gly
465                 470                 475                 480

Leu Leu Thr Asn Thr Ile Arg Gly Val Ala Asn Leu Leu Thr Gly Ser
                485                 490                 495

Arg Arg Thr Arg Arg Glu Ile Thr Leu Arg Thr Gln Ala Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
        675

<210> SEQ ID NO 39
<211> LENGTH: 676
<212> TYPE: PRT
<213> ORGANISM: Ebola virus

<400> SEQUENCE: 39

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
                20                  25                  30

Met Pro Leu Gly Val Val Thr Asn Ser Thr Leu Glu Val Thr Glu Ile
            35                  40                  45
```

-continued

```
Asp Gln Leu Val Cys Lys Asp His Leu Ala Ser Thr Asp Gln Leu Lys
 50                  55                  60

Ser Val Gly Leu Asn Leu Glu Gly Ser Gly Val Ser Thr Asp Ile Pro
 65                  70                  75                  80

Ser Ala Thr Lys Arg Trp Gly Phe Arg Ser Gly Val Pro Pro Lys Val
                 85                  90                  95

Phe Ser Tyr Glu Ala Gly Glu Trp Ala Glu Asn Cys Tyr Asn Leu Glu
             100                 105                 110

Ile Lys Lys Pro Asp Gly Ser Glu Cys Leu Pro Pro Pro Asp Gly
             115                 120                 125

Val Arg Gly Phe Pro Arg Cys Arg Tyr Val His Lys Ala Gln Gly Thr
 130                 135                 140

Gly Pro Cys Pro Gly Asp Tyr Ala Phe His Lys Asp Gly Ala Phe Phe
 145                 150                 155                 160

Leu Tyr Asp Arg Leu Ala Ser Thr Val Ile Tyr Arg Gly Val Asn Phe
                 165                 170                 175

Ala Glu Gly Val Ile Ala Phe Leu Ile Leu Ala Lys Pro Lys Glu Thr
             180                 185                 190

Phe Leu Gln Ser Pro Pro Ile Arg Glu Ala Val Asn Tyr Thr Glu Asn
             195                 200                 205

Thr Ser Ser Tyr Tyr Ala Thr Ser Tyr Leu Glu Tyr Glu Ile Glu Asn
 210                 215                 220

Phe Gly Ala Gln His Ser Thr Thr Leu Phe Lys Ile Asn Asn Asn Thr
 225                 230                 235                 240

Phe Val Leu Leu Asp Arg Pro His Thr Pro Gln Phe Leu Phe Gln Leu
                 245                 250                 255

Asn Asp Thr Ile His Leu His Gln Gln Leu Ser Asn Thr Thr Gly Lys
             260                 265                 270

Leu Ile Trp Thr Leu Asp Ala Asn Ile Asn Ala Asp Ile Gly Glu Trp
             275                 280                 285

Ala Phe Trp Glu Asn Lys Lys Asn Leu Ser Glu Gln Leu Arg Gly Glu
 290                 295                 300

Glu Leu Ser Phe Glu Thr Leu Ser Leu Asn Glu Thr Glu Asp Asp Asp
 305                 310                 315                 320

Ala Thr Ser Ser Arg Thr Thr Lys Gly Arg Ile Ser Asp Arg Ala Thr
                 325                 330                 335

Arg Lys Tyr Ser Asp Leu Val Pro Lys Asp Ser Pro Gly Met Val Ser
             340                 345                 350

Leu His Val Pro Glu Gly Glu Thr Thr Leu Pro Ser Gln Asn Ser Thr
             355                 360                 365

Glu Gly Arg Arg Val Asp Val Asn Thr Gln Glu Thr Ile Thr Glu Thr
 370                 375                 380

Thr Ala Thr Ile Ile Gly Thr Asn Gly Asn Asn Met Gln Ile Ser Thr
 385                 390                 395                 400

Ile Gly Thr Gly Leu Ser Ser Ser Gln Ile Leu Ser Ser Ser Pro Thr
                 405                 410                 415

Met Ala Pro Ser Pro Glu Thr Gln Thr Ser Thr Thr Tyr Thr Pro Lys
             420                 425                 430

Leu Pro Val Met Thr Thr Glu Ser Thr Thr Pro Pro Arg Asn Ser
             435                 440                 445

Pro Gly Ser Thr Thr Glu Ala Pro Thr Leu Thr Thr Pro Glu Asn Ile
 450                 455                 460

Thr Thr Ala Val Lys Thr Val Leu Pro Gln Glu Ser Thr Ser Asn Gly
```

```
            465                 470                 475                 480
Leu Ile Thr Ser Thr Val Thr Gly Ile Leu Gly Ser Leu Gly Leu Arg
                    485                 490                 495

Lys Arg Ser Arg Arg Gln Val Asn Thr Arg Ala Thr Gly Lys Cys Asn
                500                 505                 510

Pro Asn Leu His Tyr Trp Thr Ala Gln Glu Gln His Asn Ala Ala Gly
            515                 520                 525

Ile Ala Trp Ile Pro Tyr Phe Gly Pro Gly Ala Glu Gly Ile Tyr Thr
        530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
                580                 585                 590

Leu Leu Arg Arg Trp Gly Gly Thr Cys Arg Ile Leu Gly Pro Asp Cys
            595                 600                 605

Cys Ile Glu Pro His Asp Trp Thr Lys Asn Ile Thr Asp Lys Ile Asn
        610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
                660                 665                 670

Lys Leu Leu Cys
        675

<210> SEQ ID NO 40
<211> LENGTH: 677
<212> TYPE: PRT
<213> ORGANISM: Ebola virus

<400> SEQUENCE: 40

Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
                20                  25                  30

Ser Met Pro Leu Gly Ile Val Thr Asn Ser Thr Leu Lys Ala Thr Glu
            35                  40                  45

Ile Asp Gln Leu Val Cys Arg Asp Lys Leu Ser Ser Thr Ser Gln Leu
        50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Leu Pro Pro Asp
        115                 120                 125

Gly Val Arg Gly Phe Pro Arg Cys Arg Tyr Val His Lys Val Gln Gly
    130                 135                 140

Thr Gly Pro Cys Pro Gly Asp Leu Ala Phe His Lys Asn Gly Ala Phe
145                 150                 155                 160
```

```
Phe Leu Tyr Asp Arg Leu Ala Ser Thr Val Ile Tyr Arg Gly Thr Thr
                165                 170                 175
Phe Thr Glu Gly Val Val Ala Phe Leu Ile Leu Ser Glu Pro Lys Lys
            180                 185                 190
His Phe Trp Lys Ala Thr Pro Ala His Glu Pro Val Asn Thr Thr Asp
        195                 200                 205
Asp Ser Thr Ser Tyr Tyr Met Thr Leu Thr Leu Ser Tyr Glu Met Ser
    210                 215                 220
Asn Phe Gly Gly Lys Glu Ser Asn Thr Leu Phe Lys Val Asp Asn His
225                 230                 235                 240
Thr Tyr Val Gln Leu Asp Arg Pro His Thr Pro Gln Phe Leu Val Gln
                245                 250                 255
Leu Asn Glu Thr Leu Arg Arg Asn Asn Arg Leu Ser Asn Ser Thr Gly
            260                 265                 270
Arg Leu Thr Trp Thr Leu Asp Pro Lys Ile Glu Pro Asp Val Gly Glu
        275                 280                 285
Trp Ala Phe Trp Glu Thr Lys Lys Asn Phe Ser Gln Gln Leu His Gly
    290                 295                 300
Glu Asn Leu His Phe Gln Ile Leu Ser Thr His Thr Asn Asn Ser Ser
305                 310                 315                 320
Asp Gln Ser Pro Ala Gly Thr Val Gln Gly Lys Ile Ser Tyr His Pro
                325                 330                 335
Pro Thr Asn Asn Ser Glu Leu Val Pro Thr Asp Ser Pro Pro Val Val
            340                 345                 350
Ser Val Leu Thr Ala Gly Arg Thr Glu Glu Met Ser Thr Gln Gly Leu
        355                 360                 365
Thr Asn Gly Glu Thr Ile Thr Gly Phe Thr Ala Asn Pro Met Thr Thr
    370                 375                 380
Thr Ile Ala Pro Ser Pro Thr Met Thr Ser Glu Val Asp Asn Asn Val
385                 390                 395                 400
Pro Ser Glu Gln Pro Asn Asn Thr Ala Ser Ile Glu Asp Ser Pro Pro
                405                 410                 415
Ser Ala Ser Asn Glu Thr Ile Asp His Ser Glu Met Asn Pro Ile Gln
            420                 425                 430
Gly Ser Asn Asn Ser Ala Gln Ser Pro Gln Thr Lys Thr Thr Pro Ala
        435                 440                 445
Pro Thr Ala Ser Pro Met Thr Gln Asp Pro Gln Glu Thr Ala Asn Ser
    450                 455                 460
Ser Lys Leu Gly Thr Ser Pro Gly Ser Ala Ala Glu Pro Ser Gln Pro
465                 470                 475                 480
Gly Phe Thr Ile Asn Thr Val Ser Lys Val Ala Asp Ser Leu Ser Pro
                485                 490                 495
Thr Arg Lys Gln Lys Arg Ser Val Arg Gln Asn Thr Ala Asn Lys Cys
            500                 505                 510
Asn Pro Asp Leu His Tyr Trp Thr Ala Val Asp Glu Gly Ala Ala Val
        515                 520                 525
Gly Leu Ala Trp Ile Pro Tyr Phe Gly Pro Ala Ala Glu Gly Ile Tyr
    530                 535                 540
Ile Glu Gly Val Met His Asn Gln Asn Gly Leu Ile Cys Gly Leu Arg
545                 550                 555                 560
Gln Leu Ala Asn Glu Thr Thr Gln Ala Leu Gln Leu Phe Leu Arg Ala
                565                 570                 575
Thr Thr Glu Leu Arg Thr Tyr Ser Leu Leu Asn Arg Lys Ala Ile Asp
```

-continued

```
                580             585             590
    Phe Leu Leu Gln Arg Trp Gly Gly Thr Cys Arg Ile Leu Gly Pro Ser
                    595             600             605

Cys Cys Ile Glu Pro His Asp Trp Thr Lys Asn Ile Thr Asp Glu Ile
        610             615             620

Asn Gln Ile Lys His Asp Phe Ile Asp Asn Pro Leu Pro Asp His Gly
    625             630             635             640

Asp Asp Leu Asn Leu Trp Thr Gly Trp Arg Gln Trp Ile Pro Ala Gly
                    645             650             655

Ile Gly Ile Ile Gly Val Ile Ile Ala Ile Ile Ala Leu Leu Cys Ile
                660             665             670

Cys Lys Ile Leu Cys
                675

<210> SEQ ID NO 41
<211> LENGTH: 676
<212> TYPE: PRT
<213> ORGANISM: Ebola virus

<400> SEQUENCE: 41

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
                20                  25                  30

Ile Pro Leu Gly Val Val His Asn Asn Thr Leu Gln Val Ser Asp Ile
            35                  40                  45

Asp Lys Phe Val Cys Arg Asp Lys Leu Ser Ser Thr Ser Gln Leu Lys
        50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
                100                 105                 110

Ile Lys Lys Val Asp Gly Ser Glu Cys Leu Pro Glu Ala Pro Glu Gly
            115                 120                 125

Val Arg Asp Phe Pro Arg Cys Arg Tyr Val His Lys Val Ser Gly Thr
        130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
                180                 185                 190

Phe Phe Gln Ser Pro Pro Leu His Glu Pro Ala Asn Met Thr Thr Asp
            195                 200                 205

Pro Ser Ser Tyr Tyr His Thr Thr Ile Asn Tyr Val Val Asp Asn
        210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
                260                 265                 270
```

```
Leu Ile Trp Lys Ile Asn Pro Thr Val Asp Thr Ser Met Gly Glu Trp
            275                 280                 285

Ala Phe Trp Glu Asn Lys Lys Asn Phe Thr Lys Thr Leu Ser Ser Glu
290                 295                 300

Glu Leu Ser Phe Val Pro Val Pro Glu Thr Gln Asn Gln Val Leu Asp
305                 310                 315                 320

Thr Thr Ala Thr Val Ser Pro Pro Ile Ser Ala His Asn His Ala Ala
                325                 330                 335

Glu Asp His Lys Glu Leu Val Ser Glu Asp Ser Thr Pro Val Val Gln
            340                 345                 350

Met Gln Asn Ile Lys Gly Lys Asp Thr Met Pro Thr Thr Val Thr Gly
        355                 360                 365

Val Pro Thr Thr Thr Pro Ser Pro Phe Pro Ile Asn Ala Arg Asn Thr
370                 375                 380

Asp His Thr Lys Ser Phe Ile Gly Leu Glu Gly Pro Gln Glu Asp His
385                 390                 395                 400

Ser Thr Thr Gln Pro Ala Lys Thr Ser Gln Pro Thr Asn Ser Thr
                405                 410                 415

Glu Ser Thr Thr Leu Asn Pro Thr Ser Glu Pro Ser Ser Arg Gly Thr
                420                 425                 430

Gly Pro Ser Ser Pro Thr Val Pro Asn Thr Thr Glu Ser His Ala Glu
            435                 440                 445

Leu Gly Lys Thr Thr Pro Thr Thr Leu Pro Glu Gln His Thr Ala Ala
            450                 455                 460

Ser Ala Ile Pro Arg Ala Val His Pro Asp Glu Leu Ser Gly Pro Gly
465                 470                 475                 480

Phe Leu Thr Asn Thr Ile Arg Gly Val Thr Asn Leu Thr Gly Ser
                485                 490                 495

Arg Arg Lys Arg Arg Asp Val Thr Pro Asn Thr Gln Pro Lys Cys Asn
                500                 505                 510

Pro Asn Leu His Tyr Trp Thr Ala Leu Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Ile Met Glu Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro Gln Asp Trp Thr Lys Asn Ile Thr Asp Lys Ile Asp
610                 615                 620

Gln Ile Ile His Asp Phe Val Asp Asn Leu Pro Asn Gln Asn Asp
625                 630                 635                 640

Gly Ser Asn Trp Trp Thr Gly Trp Lys Gln Trp Val Pro Ala Gly Ile
                645                 650                 655

Gly Ile Thr Gly Val Ile Ile Ala Ile Ile Ala Leu Leu Cys Ile Cys
            660                 665                 670

Lys Phe Met Leu
        675
```

<210> SEQ ID NO 42
<211> LENGTH: 681
<212> TYPE: PRT
<213> ORGANISM: Ebola virus

<400> SEQUENCE: 42

Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
                85                  90                  95

Val Thr Asp Pro Ser Gly Lys Ser Leu Leu Asp Pro Pro Thr Asn
                100                 105                 110

Ile Arg Asp Tyr Pro Lys Cys Lys Thr Ile His His Ile Gln Gly Gln
                115                 120                 125

Asn Pro His Ala Gln Gly Ile Ala Leu His Leu Trp Gly Ala Phe Phe
130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
                180                 185                 190

Ser Thr Asn Lys Tyr Trp Thr Ser Ser Asn Gly Thr Gln Thr Asn Asp
            195                 200                 205

Thr Gly Cys Phe Gly Ala Leu Gln Glu Tyr Asn Ser Thr Lys Asn Gln
210                 215                 220

Thr Cys Ala Pro Ser Lys Ile Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270

Ser Gly Glu Arg Glu Pro His Thr Thr Ser Asp Ala Val Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
                340                 345                 350

Thr Leu Ser Ala Pro Leu Gln Asn Thr Thr Asn Asp Asn Thr Gln Ser
            355                 360                 365

Thr Ile Thr Glu Asn Glu Gln Thr Ser Ala Pro Ser Ile Thr Thr Leu
        370                 375                 380

```
Pro Pro Thr Gly Asn Pro Thr Thr Ala Lys Ser Thr Ser Ser Lys Lys
385                 390                 395                 400

Gly Pro Ala Thr Thr Ala Pro Asn Thr Thr Asn Glu His Phe Thr Ser
            405                 410                 415

Pro Pro Pro Thr Pro Ser Ser Thr Ala Gln His Leu Val Tyr Phe Arg
            420                 425                 430

Arg Lys Arg Ser Ile Leu Trp Arg Glu Gly Asp Met Phe Pro Phe Leu
            435                 440                 445

Asp Gly Leu Ile Asn Ala Pro Ile Asp Phe Asp Pro Val Pro Asn Thr
            450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
            485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
            515                 520                 525

Gly Leu Ser Trp Ile Pro Phe Phe Gly Pro Gly Ile Glu Gly Leu Tyr
            530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
            565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
            595                 600                 605

Cys Cys Ile Gly Ile Glu Asp Leu Ser Lys Asn Ile Ser Glu Gln Ile
            610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
            645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
            675                 680

<210> SEQ ID NO 43
<211> LENGTH: 29
<212> TYPE: PRT
<213> ORGANISM: Ebola virus

<400> SEQUENCE: 43

Ser Glu Thr Ala Gly Asn Asn Asn Thr His His Gln Asp Thr Gly Glu
1               5                   10                  15

Glu Ser Ala Ser Ser Gly Lys Leu Gly Leu Ile Thr Asn
            20                  25

<210> SEQ ID NO 44
<211> LENGTH: 29
<212> TYPE: PRT
<213> ORGANISM: Ebola virus

<400> SEQUENCE: 44
```

```
Thr Met Ile Thr Ser His Asp Thr Asp Ser Asn Arg Pro Asn Pro Ile
1               5                   10                  15

Asp Ile Ser Glu Ser Thr Glu Pro Gly Leu Leu Thr Asn
            20                  25
```

<210> SEQ ID NO 45
<211> LENGTH: 28
<212> TYPE: PRT
<213> ORGANISM: Ebola virus

<400> SEQUENCE: 45

```
Thr Leu Thr Thr Pro Glu Asn Ile Thr Thr Ala Val Lys Thr Val Leu
1               5                   10                  15

Pro Gln Glu Ser Thr Ser Asn Gly Leu Ile Thr Ser
            20                  25
```

<210> SEQ ID NO 46
<211> LENGTH: 29
<212> TYPE: PRT
<213> ORGANISM: Ebola virus

<400> SEQUENCE: 46

```
Thr Leu Pro Glu Gln His Thr Ala Ala Ser Ala Ile Pro Arg Ala Val
1               5                   10                  15

His Pro Asp Glu Leu Ser Gly Pro Gly Phe Leu Thr Asn
            20                  25
```

<210> SEQ ID NO 47
<211> LENGTH: 69
<212> TYPE: PRT
<213> ORGANISM: Ebola virus

<400> SEQUENCE: 47

```
Ala Phe His Lys Glu Gly Ala Phe Phe Leu Tyr Asp Arg Leu Ala Ser
1               5                   10                  15

Thr Val Ile Tyr Arg Gly Thr Thr Phe Ala Glu Gly Val Val Ala Phe
            20                  25                  30

Leu Ile Leu Pro Gln Ala Lys Lys Asp Phe Phe Ser Ser His Pro Leu
        35                  40                  45

Arg Glu Pro Val Asn Ala Thr Glu Asp Pro Ser Ser Gly Tyr Tyr Ser
    50                  55                  60

Thr Thr Ile Arg Tyr
65
```

<210> SEQ ID NO 48
<211> LENGTH: 69
<212> TYPE: PRT
<213> ORGANISM: Ebola virus

<400> SEQUENCE: 48

```
Ala Phe His Lys Glu Gly Ala Phe Phe Leu Tyr Asp Arg Leu Ala Ser
1               5                   10                  15

Thr Ile Ile Tyr Arg Ser Thr Thr Phe Ser Glu Gly Val Val Ala Phe
            20                  25                  30

Leu Ile Leu Pro Lys Thr Lys Lys Asp Phe Phe Gln Ser Pro Pro Leu
        35                  40                  45

His Glu Pro Ala Asn Met Thr Thr Asp Pro Ser Ser Tyr Tyr His Thr
    50                  55                  60

Val Thr Leu Asn Tyr
65
```

<210> SEQ ID NO 49
<211> LENGTH: 69
<212> TYPE: PRT
<213> ORGANISM: Ebola virus

<400> SEQUENCE: 49

Ala Phe His Lys Asp Gly Ala Phe Phe Leu Tyr Asp Arg Leu Ala Ser
1               5                   10                  15

Thr Val Ile Tyr Arg Gly Val Asn Phe Ala Glu Gly Val Ile Ala Phe
            20                  25                  30

Leu Ile Leu Ala Lys Pro Lys Glu Thr Phe Leu Gln Ser Pro Pro Ile
        35                  40                  45

Arg Glu Ala Val Asn Tyr Thr Glu Asn Thr Ser Ser Tyr Tyr Ala Thr
    50                  55                  60

Ser Tyr Leu Glu Tyr
65

<210> SEQ ID NO 50
<211> LENGTH: 69
<212> TYPE: PRT
<213> ORGANISM: Ebola virus

<400> SEQUENCE: 50

Ala Phe His Lys Glu Gly Ala Phe Phe Leu Tyr Asp Arg Leu Ala Ser
1               5                   10                  15

Thr Ile Ile Tyr Arg Gly Thr Thr Phe Ala Glu Gly Val Ile Ala Phe
            20                  25                  30

Leu Ile Leu Pro Lys Ala Arg Lys Asp Phe Phe Gln Ser Pro Pro Leu
        35                  40                  45

His Glu Pro Ala Asn Met Thr Thr Asp Pro Ser Ser Tyr Tyr His Thr
    50                  55                  60

Thr Thr Ile Asn Tyr
65

<210> SEQ ID NO 51
<211> LENGTH: 11
<212> TYPE: PRT
<213> ORGANISM: Ebola virus

<400> SEQUENCE: 51

Gly Glu Trp Ala Phe Trp Glu Thr Lys Lys Asn
1               5                   10

<210> SEQ ID NO 52
<211> LENGTH: 11
<212> TYPE: PRT
<213> ORGANISM: Ebola virus

<400> SEQUENCE: 52

Gly Glu Trp Ala Phe Trp Glu Asn Lys Lys Asn
1               5                   10

<210> SEQ ID NO 53
<211> LENGTH: 28
<212> TYPE: PRT
<213> ORGANISM: Ebola virus

<400> SEQUENCE: 53

Lys Asn Ile Ser Glu Gln Ile Asp Gln Ile Lys Lys Asp Glu Gln Lys
1               5                   10                  15

Glu Gly Thr Gly Trp Gly Leu Gly Gly Lys Trp Trp
            20                  25

<210> SEQ ID NO 54
<211> LENGTH: 29
<212> TYPE: PRT
<213> ORGANISM: Ebola virus

<400> SEQUENCE: 54

Lys Asn Ile Ser Glu Gln Ile Asp Gln Ile Lys Lys Asp Glu Gln Lys
1               5                   10                  15

Glu Gly Thr Gly Trp Gly Leu Gly Gly Lys Trp Trp Thr
            20                  25

<210> SEQ ID NO 55
<211> LENGTH: 30
<212> TYPE: PRT
<213> ORGANISM: Ebola virus

<400> SEQUENCE: 55

Gly Leu Ile Asn Ala Pro Ile Asp Phe Asp Pro Val Pro Asn Thr Lys
1               5                   10                  15

Thr Ile Phe Asp Glu Ser Ser Ser Gly Ala Ser Ala Glu
            20                  25                  30

<210> SEQ ID NO 56
<211> LENGTH: 27
<212> TYPE: PRT
<213> ORGANISM: Ebola virus

<400> SEQUENCE: 56

Leu Trp Arg Glu Gly Asp Met Phe Pro Phe Leu Asp Gly Leu Ile Asn
1               5                   10                  15

Ala Pro Ile Asp Phe Asp Pro Val Pro Thr Lys
            20                  25

<210> SEQ ID NO 57
<211> LENGTH: 28
<212> TYPE: PRT
<213> ORGANISM: Ebola virus

<400> SEQUENCE: 57

Ile Leu Trp Arg Glu Gly Asp Met Phe Pro Phe Leu Asp Gly Leu Ile
1               5                   10                  15

Asn Ala Pro Ile Asp Phe Asp Pro Val Pro Thr Lys
            20                  25

<210> SEQ ID NO 58
<211> LENGTH: 21
<212> TYPE: PRT
<213> ORGANISM: Ebola virus

<400> SEQUENCE: 58

Asp Glu Asp Leu Ala Thr Ser Gly Ser Gly Ser Gly Glu Arg Glu Pro
1               5                   10                  15

His Thr Thr Ser Asp
            20

<210> SEQ ID NO 59
<211> LENGTH: 26
<212> TYPE: PRT
<213> ORGANISM: Ebola virus

```
<400> SEQUENCE: 59

Leu Asp Lys Asn Asn Thr Thr Ala Gln Pro Ser Met Pro Pro His Asn
1               5                   10                  15

Thr Thr Thr Ile Ser Thr Asn Asn Thr Ser
            20                  25

<210> SEQ ID NO 60
<211> LENGTH: 28
<212> TYPE: PRT
<213> ORGANISM: Ebola virus

<400> SEQUENCE: 60

Val Gln Glu Asp Asp Leu Ala Ala Gly Leu Ser Trp Ile Pro Phe Phe
1               5                   10                  15

Gly Pro Gly Ile Glu Gly Leu Tyr Thr Ala Gly Leu
            20                  25

<210> SEQ ID NO 61
<211> LENGTH: 69
<212> TYPE: PRT
<213> ORGANISM: Ebola virus

<400> SEQUENCE: 61

Ala Leu His Leu Trp Gly Ala Phe Phe Leu Tyr Asp Arg Ile Ala Ser
1               5                   10                  15

Thr Thr Met Tyr Arg Gly Lys Val Phe Thr Glu Gly Asn Ile Ala Ala
            20                  25                  30

Met Ile Val Asn Lys Thr Val His Lys Met Ile Phe Ser Arg Gln Gly
        35                  40                  45

Gln Gly Tyr Arg His Met Asn Leu Thr Ser Thr Asn Lys Tyr Trp Thr
    50                  55                  60

Ser Ser Asn Gly Thr
65

<210> SEQ ID NO 62
<211> LENGTH: 10
<212> TYPE: PRT
<213> ORGANISM: Ebola virus

<400> SEQUENCE: 62

Ala Thr Ser Gly Ser Gly Ser Gly Glu Arg
1               5                   10
```

PEPTIDE FRAGMENTS FROM FILOVIRUSES AND THEIR USES

CROSS REFERENCE TO RELATED APPLICATION

This is a continuation of U.S. patent application Ser. No. 16/346,009, filed Apr. 29, 2019, which is the U.S. National Stage of International Application No. PCT/US2017/059407, filed Oct. 31, 2017, which was published in English under PCT Article 21(2), which in turn claims the benefit of U.S. Provisional Application No. 62/414,960, filed Oct. 31, 2016. The provisional application is incorporated herein by reference in its entirety.

FIELD

The present disclosure relates to immunogenic compositions comprising one or more peptide fragments from filoviruses that can induce an immune response in a mammal.

BACKGROUND

The 2014 epidemic of highly pathogenic ebolavirus in Western Africa resulted in tens of thousands of infections and deaths. With occasional small outbreaks of new cases in West Africa and the possibility of long-term persistence of virus in some survivors, it is feared that future outbreaks can occur, resulting in severe epidemics. Development of an effective vaccine against ebolavirus is a high priority, both for pre-epidemic preparedness and for rapid vaccination to control future outbreaks.

Protection against Ebola Virus Disease is, at least, partially attributed to the humoral immune response, since passive transfer of antibodies to naïve non-human primates can protect the recipients against lethal ebolavirus challenge. However, no single assay has been found to be predictive of protection while the correlation of antibody titers measured by various assays has not been clearly demonstrated. Further, the difficulty of conducting adequate randomized controlled trials to demonstrate vaccine effectiveness impedes vaccine development.

SUMMARY

Disclosed herein are isolated peptide fragments of filovirus glycoprotein (GP) that induce an immune response to the GP that neutralizes infection by the virus. The peptide fragments include an identified antigenic site of the filovirus GP that is capable of inducing a neutralizing immune response in a subject. Accordingly, isolated peptides are provided that contain a disclosed filovirus GP antigenic site. In some embodiments, the isolated peptide is from an ebolavirus GP and induces an immune response to ebolavirus GP that neutralizes subsequent infection with the ebolavirus. The peptide can be further conjugated to a carrier to facilitate presentation to the immune system.

In some embodiments, an isolated peptide is provided, wherein the peptide comprises, consists essentially of, or consists of the amino acid sequence set forth as the antigenic site VI of a filovirus GP, such as SEQ ID NO: 9: KNITDKIX$_1$QIIHDFX$_2$DX$_3$X$_4$TLPX$_5$QX$_6$X$_7$X$_8$X$_9$NWW, wherein X$_1$ is D or N, X$_2$ is V or I, X$_3$ is K or N, X$_4$ is T, P, or N, X$_5$ is D or N, X$_6$ is G, T, D, or N, X$_7$ is D or N, X$_8$ is N, D, or G, and X$_9$ is D or S, wherein the peptide is no more than 100 (such as no more than 75 or no more than 50) amino acids in length and induces a neutralizing immune response to filovirus (such as ebolavirus) in a subject. For example, an isolated peptide comprising, consisting essentially of, or consisting of the amino acid sequence set forth any one of SEQ ID NOs: 10-13 or 53 or 4, 14-16, or 54.

In some embodiments, an isolated peptide is provided, wherein the peptide comprises, consists essentially of, or consists of the amino acid sequence set forth as the antigenic site VIA of a filovirus GP, such as SEQ ID NO: 6: FX$_2$DX$_3$X$_4$TLPX$_5$QX$_6$X$_7$X$_8$X$_9$NWWT, wherein X$_2$ is V or I, X$_3$ is K or N, X$_4$ is T, P, or N, X$_5$ is D or N; X$_6$ is G, T, D, or N; X$_7$ is D or N, X$_8$ is N, D, or G; and X$_9$ is D or S, wherein the peptide is no more than 100 (such as no more than 75 or no more than 50) amino acids in length and induces a neutralizing immune response to filovirus (such as ebolavirus) in a subject. For example, an isolated peptide comprising, consisting essentially of, or consisting of the amino acid sequence set forth as any one of SEQ ID NO: 5 or residues 14-30 of any one of SEQ ID NOs: 14-16 or 54.

In some embodiments, an isolated peptide is provided, wherein the peptide comprises, consists essentially of, or consists of the amino acid sequence set forth as the antigenic site V.7 of a filovirus GP, such as any one of SEQ ID NOs: 3, 32-34, or 55, wherein the peptide is no more than 100 (such as no more than 75 or no more than 50) amino acids in length and induces a neutralizing immune response to filovirus (such as ebolavirus) in a subject.

In some embodiments, an isolated peptide is provided, wherein the peptide comprises, consists essentially of, or consists of the amino acid sequence set forth as the antigenic site V.6 of a filovirus GP, such as any one of SEQ ID NOs: 2, 26-28, or 56, or 43-46 or 57, wherein the peptide is no more than 100 (such as no more than 75 or no more than 50) amino acids in length and induces a neutralizing immune response to filovirus (such as ebolavirus) in a subject.

In some embodiments, an isolated peptide is provided, wherein the peptide comprises, consists essentially of, or consists of the amino acid sequence set forth as the antigenic site IV.1 of a filovirus GP, such as any one of SEQ ID NOs: 17-20 or 58, wherein the peptide is no more than 100 (such as no more than 75 or no more than 50) amino acids in length and induces a neutralizing immune response to filovirus (such as ebolavirus) in a subject.

In some embodiments, an isolated peptide is provided, wherein the peptide comprises, consists essentially of, or consists of the amino acid sequence set forth as the antigenic site V.1 of a filovirus GP, such as any one of SEQ ID NOs: 21-25 or 59, wherein the peptide is no more than 100 (such as no more than 75 or no more than 50) amino acids in length and induces a neutralizing immune response to filovirus (such as ebolavirus) in a subject.

In some embodiments, an isolated peptide is provided, wherein the peptide comprises, consists essentially of, or consists of the amino acid sequence set forth as the antigenic site V.10 of a filovirus GP, such as any one of SEQ ID NOs: 29-31 or 60, wherein the peptide is no more than 100 (such as no more than 75 or no more than 50) amino acids in length and induces a neutralizing immune response to filovirus (such as ebolavirus) in a subject.

In some embodiments, an isolated peptide is provided, wherein the peptide comprises, consists essentially of, or consists of the amino acid sequence set forth as the antigenic site IL 1 of a filovirus GP, such as any one of SEQ ID NOs: 47-50 or 61, wherein the peptide is no more than 100 (such as no more than 75 or no more than 50) amino acids in length and induces a neutralizing immune response to filovirus (such as ebolavirus) in a subject.

In some embodiments, an isolated peptide is provided, wherein the peptide comprises, consists essentially of, or consists of the amino acid sequence set forth as the antigenic site IV.2 of a filovirus GP, such as any one of SEQ ID NOs: 51-52 or 62, wherein the peptide is no more than 100 (such as no more than 75 or no more than 50) amino acids in length and induces a neutralizing immune response to filovirus (such as ebolavirus) in a subject.

Nucleic acid molecules encoding the disclosed immunogens and expression vectors (such as an inactivated or attenuated viral vector) including the nucleic acid molecules are also provided.

Immunogenic compositions including the disclosed peptide (for example, linked to a carrier) or a nucleic acid molecule or vector encoding the peptide are also provided. The immunogenic composition is suitable for administration to a subject, and may also be contained in a unit dosage form. The immunogenic compositions can further include an adjuvant.

Methods of inducing an immune response to filovirus GP in a subject are disclosed. In such methods a subject, such as a human subject, is administered an effective amount of a disclosed immunogenic composition to elicit the immune response. The subject can be, for example, a human subject at risk of or having an ebolavirus infection.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1C. Analysis of antibody repertoires elicited in adults after first and second vaccinations with different doses of rVSVΔG-ZEBOV-GP. (FIG. 1A) Number of captured phage clones isolated using EBOV GFPDL affinity selection with sera from adults after the first and second vaccinations with 3 million, 20 million or 100 million PFU rVSVΔG-ZEBOV-GP vaccine (n=10 per group). (FIGS. 1B and 1C) Schematic alignments of the peptides recognized in sera after the first (FIG. 1B) and second (FIG. 1C) vaccinations, identified by panning with EBOV GFPDL Amino acid designations are based on the GP protein sequence encoded by the complete EBOV GP gene (FIG. 9). SP, signal peptide; HR1, heptad repeat 1; HR2, heptad repeat 2; TM, transmembrane domain; CT, cytoplasmic tail. Bars indicate identified inserts in GP sequence. Graphical distribution of representative clones with a frequency of ≥2 obtained after affinity selection are shown. The horizontal positions and the lengths of the bars indicate the peptide sequence displayed on the selected phage clone to its homologous sequence in the EBOV GP sequence on alignment. The thickness of each bar represents the frequency of repetitively isolated phage, with the scale shown below the alignment. The GFPDL affinity selection was performed in quadruplicate (two independent experiments by two different investigators, who were blinded to sample identity).

(FIG. 2A) Antigenic sites within the EBOV GP recognized by serum antibodies after vaccination (based on data presented in FIG. 1) Amino acid designations are based on the GP protein sequence encoded by the complete EBOV GP gene (FIG. 9). Epitopes previously described using MAbs are shown above the GP schematic. Critical residues for binding of MAbs in anti-EBOV cocktails ZMAb (1H3 (blue asterisks) and 2G4 and 4G7 (pink asterisks)), MB-003 (13C6 (red asterisks), 6D8 and 13F6) and MAb KZ52 (Davidson, E. et al. *J. Virol.* 89, 10982-10992, 2015) are shown. (FIGS. 2B and 2C) Distribution and frequency of phage clones expressing each of the key GP antigenic sites after first (FIG. 2B) or second (FIG. 2C) vaccination across dosage groups (3 million PFU, 20 million PFU and 100 million PFU). The number of clones encoding each antigenic site was divided by the total number of EBOV GFPDL-selected clones for pooled sera from each vaccine-dose group and represented as a percentage. Error bars represent s.e.m. of 4 independent experiments. The GFPDL affinity selection was performed in quadruplicate.

FIGS. 4A-4F. SPR-based analysis of sera from rVSVΔG-ZEBOV-GP-vaccinated individuals with EBOV GP purified protein. (FIGS. 4A and 4B) Total binding (RU) to purified mature GP from Mayinga (FIG. 4A) or Makona (FIG. 4B) EBOV strains in serum samples collected at different time points from adults receiving vaccine or placebo intramuscularly on day 0 (D0) and day 28 (D28). Maximum RU values for GP binding by serum antibodies obtained from all individuals are shown. Data are mean±s.d. No significant differences were found between groups (P≥0.05, multiple-comparison adjustment using Bonferroni method). (FIG. 4C) EBOV neutralization endpoint titers of serum antibodies in pseudovirus neutralization assay (PsVNA) used for EBOV GFPDL-based epitope mapping. PsVNA80 titer refers to the highest serum dilutions required to achieve 80% viral inhibition. (FIG. 4D) Correlation between maximum RU for post-vaccination sera against Makona GP and homologous virus neutralization titers (PsVNA80; Spearman r=0.7598, P<0.0001) after the first (day 28) and second (day 56) vaccinations. (FIG. 4E) Polyclonal antibody affinity to EBOV GP after rVSVΔG-ZEBOV-GP vaccination. SPR analysis of post-vaccination sera was performed with Makona GP to determine the Kd of polyclonal serum antibodies from all individuals at different post-vaccination time points. Horizontal bars indicate mean values. *P<0.05; P<0.01; *P<0.001. (FIG. 4F) Correlation of GP-binding affinity, as measured by Kd of post-vaccination human polyclonal antibodies against Makona GP, with the homologous virus neutralization titers (PsVNA80; Spearman r=0.876, P<0.0001) after the first (day 28) and second (day 56) vaccinations. All SPR experiments were performed twice.

FIGS. 5A-5F. Antibody isotypes in human serum binding to EBOV GP after vaccination and the role of IgM antibodies in virus neutralization. (FIG. 5A) Isotypes of serum antibodies bound to EBOV GP for samples collected from adults from each of the three vaccine-dose groups at different time points, as measured in SPR. RU values for each anti-GP antibody isotype were divided by the total combined RU value for all isotypes for individual serum samples and represented as a percentage. (FIG. 5B) GP binding of IgG and IgM fractions purified from day 28 (VSV-rGP-D28) sera of one of the three subjects with equivalent representations of IgG and IgM isotypes in the EBOV GP-bound antibodies. (FIGS. 5C and 5D) Confirmation of the purity of isotype binding to GP using antihuman IgG (FIG. 5C) and antihuman IgM (FIG. 5D) secondary antibodies. (FIGS. 5E and 5F) Pseudovirus neutralization assay to evaluate purified IgG and IgM antibodies for virus neutralization against Kikwit (FIG. 5E) and Makona (FIG. 5F) EBOV strains. The data are represented as the relative contributions of IgM and IgG antibodies to the total neutralization observed for each sample. Error bars represent mean±s.e.m. of 2 technical replicates. All SPR experiments were replicated twice.

FIGS. 6A and 6B. Antigenic regions/sites of Zaire ebolavirus GP set forth as SEQ ID NO: 35 identified using GFPDL. The residues of SEQ ID NO: 35 for each sequence are indicated in the table. Table showing frequency of antigenic sites for different vaccine dose groups after first and second rVSVΔG-ZEBOV-GP vaccination. The frequency of the clone per antigenic site is calculated by dividing the frequency of occurrence of a particular clone by the total number of phage clones for each vaccine dose.

FIG. 7. Sequence conservation of antigenic regions/sites among different strains and species of ebolavirus. The reference sequence used for determining sequence conservation was SEQ ID NO: 35, and the residue numbering shown in the figure corresponds to SEQ ID NO: 35. Antigenic sites in the GP that are >70% conserved in diverse EBOV strains are shown in bold.

FIG. 8. Phage Titers from affinity selection of pooled sera with different doses of rVSVΔG-ZEBOV-GP vaccine following first vaccination using Protein A/G, IgM and IgA matrices.

FIG. 9. Complete Zaire ebolavirus Mayinga (1976) GP gene translated sequence (SEQ ID NO: 35) used for construction of Zaire ebolavirus-GFPD library and depiction in FIGS. 1-3.

FIGS. 10A and 10B. Alignment of glycoprotein (GP) sequences from Zaire ebolavirus Mayinga (1976, SEQ ID NO: 35), Kikwit (1995, SEQ ID NO: 36) and Makona (2014, SEQ ID NO: 37) strains.

FIG. 11. Random distribution of size and sequence of the EBOV-GFPDL. Sequencing of GP fragments expressed by the phages of the EBOV GFPD libraries were aligned to the Zaire EBOV GP translated sequence (shown in FIG. 9).

FIGS. 16A-16C. Anti-GP reactivity of post-first and post-second vaccination sera for 20 million and 100 million pfu vaccine dose in ELISA. The isotype of two-fold serial dilution of serum antibodies (starting at 200-fold serum dilution) bound to EBOV-GP are shown for serum samples collected at different time points from adults vaccinated with 20 million and 100 million rVSVΔG-ZEBOV-GP vaccine dose administered groups as measured in ELISA using HRP conjugated anti-human IgM muchain specific antibody (FIG. 16A), HRP conjugated anti-human IgG Fc-chain specific antibody (FIG. 16B) and HRP conjugated anti-human IgA alpha-chain specific antibody (FIG. 16C).

FIGS. 18A-18C. Individual antibody repertoires elicited following first vaccination with rVSVΔG-ZEBOV-GP vaccine using IgA, IgG and IgM specific capture beads. (FIG. 18A) Number of captured phage clones isolated using EBOV-GFPDL affinity selection with sera obtained from individual vaccinee after first vaccination with 20 or 100 million pfu rVSVΔGZEBOV-GP vaccine dose group using IgA, IgG and IgM specific capture beads by EBOVKikwit GP GFPDL. (FIG. 18B, FIG. 18C) Schematic alignment of the peptides recognized by IgG, IgM and IgA antibodies following first vaccination with 20 million (FIG. 18B) and 100 million (FIG. 18C) rVSVΔGZEBOV-GP vaccine, identified by panning with GFPDL. The amino acid designation is based on the GP protein sequence encoded by the complete EBOV GP gene (FIGS. 10A and 10B). Bars indicate identified inserts in GP sequence. The GP receptor binding region (RBR) and the mucin like domain are indicated. Bars indicate identified inserts in GP sequence. Bar location indicates the homology of the displayed EBOV-GP protein sequence on the phage clones after affinity selection. Graphical distribution of representative clone with a frequency of >2, obtained after affinity selection, are shown. The thickness of each bar represents the frequency of repetitively isolated phage, with the scale shown below the alignment.

FIGS. 19A-19C. Sequence alignment of GP proteins from Zaire ebolavirus Mayinga (SEQ ID NO: 35), Zaire ebolavirus Kikwit (SEQ ID NO: 36), Zaire ebolavirus Makona (SEQ ID NO: 37), Bundibugyo ebolavirus (SEQ ID NO: 38), Sudan ebolavirus (SEQ ID NO: 39), Tai Forest ebolavirus (SEQ ID NO: 41), and Marburg marburgvirus (SEQ ID NO: 42)

FIG. 20. Sequence of identified antigenic sites of Zaire ebolavirus Mayinga GP (SEQ ID NO: 35).

FIG. 21. Rabbit immunization of GP antigenic site peptides induces high antibody binding to homologous and heterologous native GP.

FIG. 22. Conserved antigenic sites in GP1 induce neutralizing antibodies.

FIG. 23. Zaire ebolavirus challenge study in mice Immunization with peptides from Antigenic sites V.7 in GP1 and VI in GP2 induces sterilizing immunity, while other sites provide partial protection against Ebola virus.

FIG. 24. Conserved antigenic sites in V.7 in GP1 and VIA in GP2 provide significant protection from weight loss following Zaire ebolavirus challenge, while other sites provide partial protection against Ebola virus.

FIG. 25. Conserved antigenic sites in the C-terminal region of GP1 and GP2 generate strong binding antibodies to both Mayinga and Makona GP as measured by surface plasmon resonance.

FIG. 26. Sera from human Ebola virus survivors shows higher antibody binding to diverse antigenic sites in GP than post-vaccination sera.

FIG. 27. Identification of GP antigenic sites that strongly correlate with Ebola neutralization titers (PsVN).

FIG. 28. Spatial structure of linear neutralizing and protective antigenic sites in GP.

SEQUENCES

Figure 2A:
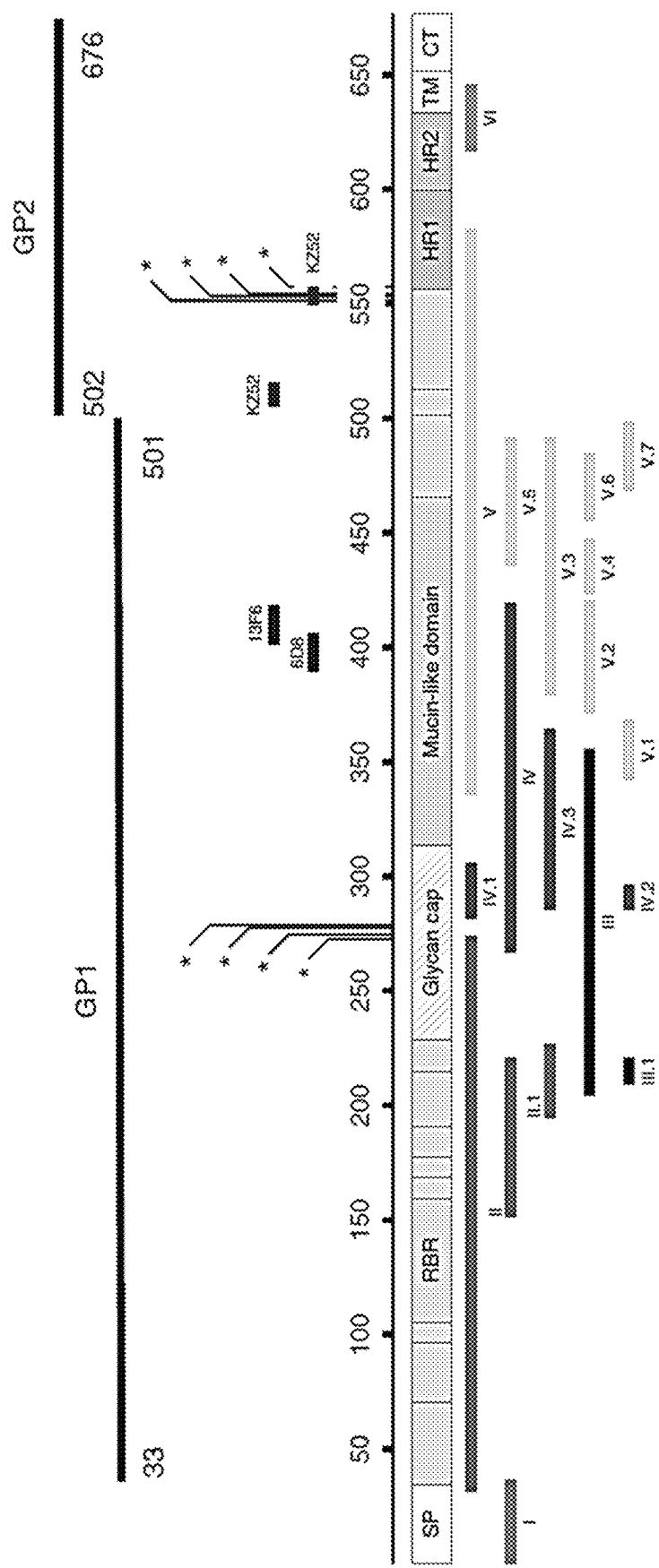
FIGS. 2A-2C. Elucidation of antibody epitope profile against Ebola GP after rVSVΔG-ZEBOV-GP vaccination in humans.

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence Listing.txt" (~28 kb), which was created on Oct. 14, 2021 which is incorporated by reference herein.

SEQ ID NOs: 1-34 and 43-61 are the amino acid sequences of immunogenic peptides, as follows:

SEQ ID NO: 1: TTEDHKIMASENSSAMVQVHSQGREAAVSH

SEQ ID NO: 8: TX$_{10}$EDHKIMASENSSAMVQVHSQGRX$_{11}$AAVSH wherein: X$_{10}$ is T or N; and X$_{11}$ is E or K.

Antigenic Site II.1 Peptides, Residues 152-220:
SEQ ID NO: 47: AFHKEGAFFLYDRLASTVIYRGTTFAEGVVAFLILPQAKKDFF SSHPLREPVNATEDPSSGYYSTTIRY (Zaire ebolavirus Mayinga, Kikwit, Makona)
SEQ ID NO: 48: AFHKEGAFFLYDRLASTIIYRSTTFSEGVVAFLILPKTKKDFFQS PPLHEPANMTTDPSSYYHTVTLNY (Bundibugyo ebolavirus)
SEQ ID NO: 49: AFHKDGAFFLYDRLASTVIYRGVNFAEGVIAFLILAKPKETFL QSPPIREAVNYTENTSSYYATSYLEY (Sudan ebolavirus)
SEQ ID NO: 50: AFHKEGAFFLYDRLASTIIYRGTTFAEGVIAFLILPKARKDFFQS PPLHEPANMTTDPSSYYHTTTINY (Tai Forest ebolavirus)
SEQ ID NO: 61: ALHLWGAFFLYDRIASTTMYRGKVFTEGNIAAMIVNKTVHKM IFSRQGQGYRHMNLTSTNKYWTSSNGT (Margburg margburgvirus)

Antigenic Site IV.1 Peptides, Residues 282-305:
SEQ ID NO: 17: DTTIGEWAFWETKKNLTRKIRSEE, Zaire ebolavirus Mayinga, Kikwit, Makona)
SEQ ID NO: 18: DTGVGEWAFWENKKNFTKTLSSEE (Bundibugyo ebolavirus)
SEQ ID NO: 19: NADIGEWAFWENKKNLSEQLRGEE (Sudan ebolavirus)
SEQ ID NO: 20: DTSMGEWAFWENKKNFKKTLSSEE (Tai Forest ebolavirus)
SEQ ID NO: 58: DEDLATSGSGSGEREPHTTSD (Margburg margburgvirus)

Antigenic Site IV.2 Peptides, Residues 286-296:
SEQ ID NO: 51: GEWAFWETKKN (Zaire ebolavirus Mayinga, Kikwit, Makona);
SEQ ID NO: 52: GEWAFWENKKN (Bundibugyo ebolavirus, Sudan ebolavirus, Tai Forest ebolavirus);
SEQ ID NO: 62: ATSGSGSGER (Margburg margburgvirus)

Antigenic Site V.1 Peptides, Residues 343-368:
SEQ ID NO: 21: ASENSSAMVQVHSQGREAAVSHLTTL (Zaire ebolavirus Mayinga, Kikwit)
SEQ ID NO: 22: ASENSSAMVQVHSQGRKAAVSHLTTL (Zaire ebolavirus Makona)
SEQ ID NO: 23: VPKDPASVVQVRDLQRENTVPTSP (Bundibugyo ebolavirus)
SEQ ID NO: 24: VPKNSPGVVPLHIPEGETTLPSQNST (Sudan ebolavirus)
SEQ ID NO: 25: VSEDSTPVVQMQNIKGKDTMPTTV (Tai Forest ebolavirus) SEQ ID NO: 59: LDKNNTTAQPSMPPHNTTTISTNNTS (Margburg margburgvirus)

Antigenic Site V.6 Peptides, Residues 457-484 and 546-484:
SEQ ID NO: 2: ETAGNNNTHHQDTGEESASSGKLGLITN (Zaire ebolavirus Mayinga, Kikwit, Makona)
SEQ ID NO: 26: MITSHDTDSNRPNPIDISESTEPGLLTN (Bundibugyo ebolavirus)
SEQ ID NO: 27: LTTPENITTAVKTVLPQESTSNGLITS (Sudan ebolavirus)
SEQ ID NO: 28: LPEQHTAASAIPRAVHPDELSGPGFLTN (Tai Forest ebolavirus)
SEQ ID NO: 56: LWREGDMFPFLDGLINAPIDFDPVPTK (Margburg margburgvirus)
SEQ ID NO: 43: SETAGNNNTHHQDTGEESASSGKLGLITN (Zaire ebolavirus Mayinga, Makona)
SEQ ID NO: 44: TMITSHDTDSNRPNPIDISESTEPGLLTN (Bundibugyo ebolavirus)
SEQ ID NO: 45: TLTTPENITTAVKTVLPQESTSNGLITS (Sudan ebolavirus)
SEQ ID NO: 46: TLPEQHTAASAIPRAVHPDELSGPGFLTN (Tai Forest ebolavirus)
SEQ ID NO: 57: ILWREGDMFPFLDGLINAPIDFDPVPTK (Margburg margburgvirus)

Antigenic Site V.7 Peptides, Residues 469-498:
SEQ ID NO: 3: TGEESASSGKLGLITNTIAGVAGLITGGRR (Zaire ebolavirus Mayinga, Kikwit, Makona)
SEQ ID NO: 32: NPIDISESTEPGLLTNTIRGVANLLTGSRR (Bundibugyo ebolavirus)
SEQ ID NO: 33: TVLPQESTSNGLITSTVTGILGSLGLRKR (Sudan ebolavirus)
SEQ ID NO: 34: RAVHPDELSGPGFLTNTIRGVTNLLTGSRR (Tai forest ebolavirus)
SEQ ID NO: 55: GLINAPIDFDPVPNTKTIFDESSSSGASAE (Margburg margburgvirus)

Antigenic Site V.10 Peptides, Residues 520-547:
  SEQ ID NO: 29: TQDEGAAIGLAWIPYFGPAAE-GIYIEGL (Zaire ebolavirus Mayinga)
  SEQ ID NO: 30: TQDEGAAIGLAWIPYFGPAAE-GIYTEGL (Zaire ebolavirus Kikwit, Makona, Sudan ebolavirus)
  SEQ ID NO: 31: TQDEGAAIGLAWIPYFGPAAE-GIYTEGI (Bundibugyo ebolavirus, Tai Forest ebolavirus)
  SEQ ID NO: 60: VQEDDLAAGLSWIPFFGPGIEG-LYTAGL (Margburg margburgvirus)
Antigenic Site VI Peptides, Residues 617-645 or 617-646:
  SEQ ID NO: 9 (KNITDKIX$_1$QIIHDFX$_2$DX$_3$X$_4$TLPX$_5$QX$_6$X$_7$X$_8$X$_9$NWW, wherein X$_1$ is D or N, X$_2$ is V or I, X$_3$ is K or N, X$_4$ is T, P, or N, X$_5$ is D or N, X$_6$ is G, T, D, or N, X$_7$ is D or N, X$_8$ is N, D, or G, and X$_9$ is D or S (Antigenic site VI consensus)
  SEQ ID NO: 10: KNITD-KIDQIIHDFVDKTLPDQGDNDNWW (Zaire ebolavirus Mayinga, Kikwit, Makona)
  SEQ ID NO: 11: KNITDKINQIIHD-FIDKPLPDQTDNDNWW (Bundibugyo ebolavirus)
  SEQ ID NO: 12: KNITDKIDQIIHDFIDN-PLPNQDNDDNWW (Sudan ebolavirus)
  SEQ ID NO: 13: KNITD-KINQIIHDFVDNNLPNQNDGSNWW (Tai Forest ebolavirus)
  SEQ ID NO: 53: KNISEQIDQIKKDEQKEG-TGWGLGGKWW (Margburg margburgvirus)
  SEQ ID NO: 7: KNITDKIX$_1$QIIHDFX$_2$DX$_3$X$_4$TLPX$_5$QX$_6$X$_7$X$_8$X$_9$NWWT wherein: X$_1$ is D or N, X$_2$ is V and I, X$_3$ is K or N, X$_4$ is T, P, or N, X$_5$ is D or N, X$_6$ is G, T, D, or N, X$_7$ is D or N, X$_8$ is N, D, or G; and X$_9$ is D or S
  SEQ ID NO: 4: KNITD-KIDQIIHDFVDKTLPDQGDNDNWWT (Zaire ebolavirus Mayinga, Kikwit, Makona)
  SEQ ID NO: 14: KNITDKINQIIHD-FIDKPLPDQTDNDNWWT (Bundibugyo ebolavirus)
  SEQ ID NO: 15: KNITDKIDQIIHDFIDN-PLPNQDNDDNWWT (Sudan ebolavirus)
  SEQ ID NO: 16: KNITD-KINQIIHDFVDNNLPNQNDGSNWWT (Tai Forest ebolavirus)
  SEQ ID NO: 54: KNISEQIDQIKKDEQKEG-TGWGLGGKWWT (Margburg margburgvirus)
Antigenic Site VI.1 Peptides, Residues 630-646:
  SEQ ID NO: 6 (FX$_2$DX$_3$X$_4$TLPX$_5$QX$_6$X$_7$X$_8$X$_9$NWWT, wherein: X$_2$ is selected from V and I; X$_3$ from K and N; X$_4$ from T, P, and N; X$_5$ and X$_7$ from D and N; X$_6$ from G, T, D, and N; X$_8$ from N, D, and G; and X$_9$ from D and S
  SEQ ID NO: 5: FVDKTLPDQGDNDNWWT (Zaire ebolavirus Mayinga, Kikwit, Makona)
  Residues 14-30 of SEQ ID NO: 14: KNITDKINQIIHD-FIDKPLPDQTDNDNWWT (Bundibugyo ebolavirus)
  Residues 14-30 of SEQ ID NO: 15: KNITDKIDQIIHD-FIDNPLPNQDNDDNWWT (Sudan ebolavirus)
  Residues 14-30 of SEQ ID NO: 16: KNITD-KINQIIHDFVDNNLPNQNDGSNWWT (Tai Forest ebolavirus)
  SEQ ID NO: 35 is an exemplary amino acid sequence of a precursor of the GP from the Mayinga Strain of Zaire ebolavirus (GENBANK Acc. No. AIO11753.1, which is incorporated by reference herein in its entirety).

```
MGVTGILQLPRDRFKRTSFFLWVIILFQRTFSIPLGVIHNSTLQVSDVDK
LVCRDKLSSTNQLRSVGLNLEGNGVATDVPSATKRWGFRSGVPPKVVNYE
AGEWAENCYNLEIKKPDGSECLPAAPDGIRGFPRCRYVHKVSGTGPCAGD
FAFHKEGAFFLYDRLASTVIYRGTTFAEGVVAFLILPQAKKDFFSSHPLR
EPVNATEDPSSGYYSTTIRYQATGFGTNETEYLFEVDNLTYVQLESRFTP
QFLLQLNETIYTSGKRSNTTGKLIWKVNPEIDTTIGEWAFWETKKNLTRK
IRSEELSFTVVSNGAKNISGQSPARTSSDPGTNTTTEDHKIMASENSSAM
VQVHSQGREAAVSHLTTLATISTSPQSLTTKPGPDNSTHNTPVYKLDISE
ATQVEQHHRRTDNDSTASDTPSATTAAGPPKAENTNTSKSTDFLDPATTT
SPQNHSETAGNNNTHHQDTGEESASSGKLGLITNTIAGVAGLITGGRRTR
REAIVNAQPKCNPNLHYWTTQDEGAAIGLAWIPYFGPAAEGIYIEGLMHN
QDGLICGLRQLANETTQALQLFLRATTELRTFSILNRKAIDFLLQRWGGT
CHILGPDCCIEPHDWTKNITDKIDQIIHDFVDKTLPDQGDNDNWWTGWRQ
WIPAGIGVTGVIIAVIALFCICKFVF
```

SEQ ID NO: 36 is an exemplary amino acid sequence of a precursor of the GP from the Kikwit Strain of Zaire ebolavirus (GENBANK Acc. No. AIO11753.1, which is incorporated by reference herein in its entirety).

```
MGVTGILQLPRDRFKRTFFLWVIILFQRTFSIPLGVIHNSTLQVSDVDKL
VCRDKLSSTNQLRSVGLNLEGNGVATDVPSATKRWGFRSGVPPKVVNYEA
GEWAENCYNLEIKKPDGSECLPAAPDGIRGFPRCRYVHKVSGTGPCAGDF
AFHKEGAFFLYDRLASTVIYRGTTFAEGVVAFLILPQAKKDFFSSHPLRE
PVNATEDPSSGYYSTTIRYQATGFGTNETEYLFEVDNLTYVQLESRFTPQ
FLLQLNETIYTSGKRSNTTGKLIWKVNPEIDTTIGEWAFWETKKNLTRKI
RSEELSFTAVSNRAKNISGQSPARTSSDPGTNTTTEDHKIMASENSSAMV
QVHSQGREAAVSHLTTLATISTSPQPPTTKPGPDNSTHNTPVYKLDISEA
TQVEQHHRRTDNDSTASDTPPATTAAGPLKAENTNTSKGTDLLDPATTTS
PQNHSETAGNNNTHHQDTGEESASSGKLGLITNTIAGVAGLITGGRRARR
EAIVNAQPKCNPNLHYWTTQDEGAAIGLAWIPYFGPAAEGIYTEGLMHNQ
DGLICGLRQLANETTQALQLFLRATTELRTFSILNRKAIDFLLQRWGGTC
HILGPDCCIEPHDWTKNITDKIDQIIHDFVDKTLPDQGDNDNWWTGWRQW
IPAGIGVTGVIIAVIALFCICKFVF
```

SEQ ID NO: 37 is an exemplary amino acid sequence of a precursor of the GP from the Makona Strain of Zaire ebolavirus (GENBANK Acc. No. AIO11753.1, which is incorporated by reference herein in its entirety).

```
MGVTGILQLPRDRFKRTSFFLWVIILFQRTFSIPLGVIHNSTLQVSDVDK
LVCRDKLSSTNQLRSVGLNLEGNGVATDVPSVTKRWGFRSGVPPKVVNYE
AGEWAENCYNLEIKKPDGSECLPAAPDGIRGFPRCRYVHKVSGTGPCAGD
FAFHKEGAFFLYDRLASTVIYRGTTFAEGVVAFLILPQAKKDFFSSHPLR
EPVNATEDPSSGYYSTTIRYQATGFGTNETEYLFEVDNLTYVQLESRFTP
QFLLQLNETIYASGKRSNTTGKLIWKVNPEIDTTIGEWAFWETKKNLTRK
```

-continued

IRSEELSFTAVSNGPKNISGQSPARTSSDPETNTTNEDHKIMASENSSAM

VQVHSQGRKAAVSHLTTLATISTSPQPPTTKTGPDNSTHNTPVYKLDISE

ATQVGQHHRRADNDSTASDTPPATTAAGPLKAENTNTSKSADSLDLATTT

SPQNYSETAGNNNTHHQDTGEESASSGKLGLITNTIAGVAGLITGGRRTR

REVIVNAQPKCNPNLHYWTTQDEGAAIGLAWIPYFGPAAEGIYTEGLMHN

QDGLICGLRQLANETTQALQLFLRATTELRTFSILNRKAIDFLLQRWGGT

CHILGPDCCIEPHDWTKNITDKIDQIIHDFVDKTLPDQGDNDNWWTGWRQ

WIPAGIGVTGVIIAVIALFCICKFVF

SEQ ID NO: 38 is an exemplary amino acid sequence of a precursor of the GP from Bundibugyo ebolavirus (GENBANK Acc. No. AGL73460.1, which is incorporated by reference herein in its entirety).

MVTSGILQLPRERFRKTSFFVWVIILFHKVFPIPLGVVHNNTLQVSDIDK

LVCRDKLSSTSQLKSVGLNLEGNGVATDVPTATKRWGFRAGVPPKVVNYE

AGEWAENCYNLDIKKADGSECLPEAPEGVRGFPRCRYVHKVSGTGPCPEG

FAFHKEGAFFLYDRLASTIIYRSTTFSEGVVAFLILPKTKKDFFQSPPLH

EPANMTTDPSSYYHTVTLNYVADNFGTNMTNFLFQVDHLTYVQLEPRFTP

QFLVQLNETIYTNGRRSNTTGTLIWKVNPTVDTGVGEWAFWENKKNFTKT

LSSEELSVILVPRAQDPGSNQKTKVTPTSFANNQTSKNHEDLVPKDPASV

VQVRDLQRENTVPTSPLNTVPTTLIPDTMEEQTTSHYELPNISGNHQERN

NTAHPETLANNPPDNTTPSTPPQDGERTSSHTTPSPRPVPTSTIHPTTRE

TQIPTTMITSHDTDSNRPNPIDISESTEPGLLTNTIRGVANLLTGSRRTR

REITLRTQAKCNPNLHYWTTQDEGAAIGLAWIPYFGPAAEGIYTEGIMHN

QNGLICGLRQLANETTQALQLFLRATTELRTFSILNRKAIDFLLQRWGGT

CHILGPDCCIEPHDWTKNITDKIDQIIHDFIDKPLPDQTDNDNWWTGWRQ

WVPAGIGITGVIIAVIALLCICKFLL

SEQ ID NO: 39 is an exemplary amino acid sequence of a precursor of the GP from Sudan ebolavirus (GENBANK Acc. No. ACR33190.1, which is incorporated by reference herein in its entirety).

MEGLSLLQLPRDKFRKSSFFVWVIILFQKAFSMPLGVVTNSTLEVTEIDQ

LVCKDHLASTDQLKSVGLNLEGSGVSTDIPSATKRWGFRSGVPPKVFSYE

AGEWAENCYNLEIKKPDGSECLPPPPDGVRGFPRCRYVHKAQGTGPCPGD

YAFHKDGAFFLYDRLASTVIYRGVNFAEGVIAFLILAKPKETFLQSPPIR

EAVNYTENTSSYYATSYLEYEIENFGAQHSTTLFKINNNTFVLLDRPHTP

QFLFQLNDTIHLHQQLSNTTGKLIWTLDANINADIGEWAFWENKKNLSEQ

LRGEELSFETLSLNETEDDDATSSRTTKGRISDRATRKYSDLVPKDSPGM

VSLHVPEGETTLPSQNSTEGRRVDVNTQETITETTATIIGINGNNMQIST

IGTGLSSSQILSSSPTMAPSPETQTSTTYTPKLPVMTTEESTTPPRNSPG

STTEAPTLTTPENITTAVKTVLPQESTSNGLITSTVTGILGSLGLRKRSR

RQVNTRATGKCNPNLHYWTAQEQHNAAGIAWIPYFGPGAEGIYTEGLMHN

QNALVCGLRQLANETTQALQLFLRATTELRTYTILNRKAIDFLLRRWGGT

CRILGPDCCIEPHDWTKNITDKINQIIHDFIDNPLPNQDNDDNWWTGWRQ

WIPAGIGITGIIIAIIALLCVCKLLC

SEQ ID NO: 40 is an exemplary amino acid sequence of a precursor of the GP from Reston ebolavirus (GENBANK Acc. No. AAC54891.1, which is incorporated by reference herein in its entirety).

MGSGYQLLQLPRERFRKTSFLVWVIILFQRAISMPLGIVTNSTLKATEID

QLVCRDKLSSTSQLKSVGLNLEGNGIATDVPSATKRWGFRSGVPPKVVSY

EAGEWAENCYNLEIKKSDGSECLPLPPDGVRGFPRCRYVHKVQGTGPCPG

DLAFHKNGAFFLYDRLASTVIYRGTTFTEGVVAFLILSEPKKHFWKATPA

HEPVNTTDDSTSYYMTLTLSYEMSNFGGKESNTLFKVDNHTYVQLDRPHT

PQFLVQLNETLRRNNRLSNSTGRLTWTLDPKIEPDVGEWAFWETKKNFSQ

QLHGENLHFQILSTHTNNSSDQSPAGTVQGKISYHPPTNNSELVPTDSPP

VVSVLTAGRTEEMSTQGLINGETITGFTANPMTTTIAPSPTMTSEVDNNV

PSEQPNNTASIEDSPPSASNETIDHSEMNPIQGSNNSAQSPQTKTTPAPT

ASPMTQDPQETANSSKLGTSPGSAAEPSQPGFTINTVSKVADSLSPTRKQ

KRSVRQNTANKCNPDLHYWTAVDEGAAVGLAWIPYFGPAAEGIYIEGVMH

NQNGLICGLRQLANETTQALQLFLRATTELRTYSLLNRKAIDFLLQRWGG

TCRILGPSCCIEPHDWTKNITDEINQIKHDFIDNPLPDHGDDLNLWTGWR

QWIPAGIGIIGVIIAIIALLCICKILC

SEQ ID NO: 41 is an exemplary amino acid sequence of a precursor of the GP from Taï Forest ebolavirus (GENBANK Acc. No. ACI28632.1, which is incorporated by reference herein in its entirety).

MGASGILQLPRERFRKTSFFVWVIILFHKVFSIPLGVVHNNTLQVSDIDK

FVCRDKLSSTSQLKSVGLNLEGNGVATDVPTATKRWGFRAGVPPKVVNCE

AGEWAENCYNLAIKKVDGSECLPEAPEGVRDFPRCRYVHKVSGTGPCPGG

LAFHKEGAFFLYDRLASTIIYRGTTFAEGVIAFLILPKARKDFFQSPPLH

EPANMTTDPSSYYHTTTINYVVDNFGTNTTEFLFQVDHLTYVQLEARFTP

QFLVLLNETIYSDNRRSNTTGKLIWKINPTVDTSMGEWAFWENKKNFTKT

LSSEELSFVPVPETQNQVLDTTATVSPPISAHNHAAEDHKELVSEDSTPV

VQMQNIKGKDTMPTTVTGVPTTTPSPFPINARNTDHTKSFIGLEGPQEDH

STTQPAKTTSQPTNSTESTTLNPTSEPSSRGTGPSSPTVPNTTESHAELG

KTTPTTLPEQHTAASAIPRAVHPDELSGPGFLINTIRGVTNLLTGSRRKR

RDVTPNTQPKCNPNLHYWTALDEGAAIGLAWIPYFGPAAEGIYTEGIMEN

QNGLICGLRQLANETTQALQLFLRATTELRTFSILNRKAIDFLLQRWGGT

CHILGPDCCIEPQDWTKNITDKIDQIIHDFVDNNLPNQNDGSNWWTGWKQ

WVPAGIGITGVIIAIIALLCICKFML

SEQ ID NO: 42 is an exemplary amino acid sequence of a precursor of the GP from Marburg margburgvirus (GENBANK Acc. No. AAR85456.1, which is incorporated by reference herein in its entirety).

```
MKTTCFLISLILIQGTKNLPILEIASNNQPQNVDSVCSGTLQKTEDVHLM

GFTLSGQKVADSPLEASKRWAFRTGVPPKNVEYTEGEEAKTCYNISVTDP

SGKSLLLDPPTNIRDYPKCKTIHHIQGQNPHAQGIALHLWTSDAVTKQGL

SSTMPPTPSPQPSTPQQGGNNTNHSQDAVTELDKNNTTAQPSMPPHNTTT

ISTNNTSKHNFSTLSAPLQNTTNDNTQSTITENEQTSAPSITTLPPTGNP

TTAKSTSSKKGPATTAPNTTNEHFTSPPPTPSSTAQHLVYFRRKRSILWR

EGDMFPFLDGLINAPIDFDPVPNTKTIFDESSSSGASAEEDQHASPNISL

TLSYFPNINENTAYSGENENDCDAELRIWSVQEDDLAAGLSWIPFFGPGI

EGLYTAGLIKNQNNLVCRLRRLANQTAKSLELLLRVTTEERTFSLINRHA

IDFLLTRWGGTCKVLGPDCCIGIEDLSKNISEQIDQIKKDEQKEGTGWGL

GGKWWTSDWGVLTNLGILLLLSIAVLIALSCICRIFTKYIG
```

DETAILED DESCRIPTION

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, AS like adjuvants including ASO1, MF59, ALFQ or other oil in water or water in oil adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. Additional description of adjuvants can be found, for example, in Singh (ed.) Vaccine Adjuvants and Delivery Systems. Wiley-Interscience, 2007). Adjuvants can be used in combination with the disclosed immunogens.

Administration: The introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody: An immunoglobulin, antigen-binding fragment, or derivative thereof, that specifically binds and recognizes an analyte (antigen), such as a peptide from ebolavirus GP. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen.

Carrier: An immunogenic molecule to which a peptide can be linked to enhance an immune response to the peptide. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Conjugate: A complex of at least two heterologous molecules linked together. In a non-limiting example, an ebolavirus peptide as disclosed herein is conjugated to a protein carrier by a linker.

Consists essentially of and Consists Of: A polypeptide comprising an amino acid sequence that consists essentially of a specified amino acid sequence does not include any additional amino acid residues. However, the residues in the polypeptide can be modified to include non-peptide components, such as labels (for example, fluorescent, radioactive, or solid particle labels), sugars or lipids, and the N- or C-terminus of the polypeptide can be joined (for example, by peptide bond) to heterologous amino acids, such as a cysteine (or other) residue in the context of a linker for conjugation chemistry. A polypeptide that consists of a specified amino acid sequence does not include any additional amino acid residues, nor does it include additional biological components, such as nucleic acids lipids, sugars, nor does it include labels. However, the N- or C-terminus of the polypeptide can be joined (for example, by peptide bond) to heterologous amino acids, such as a peptide tag, or a cysteine (or other) residue in the context of a linker for conjugation chemistry.

A polypeptide that consists or consists essentially of a specified amino acid sequence can be glycosylated or have an amide modification. A polypeptide that consists of or consists essentially of a particular amino acid sequence can be linked via its N- or C-terminus to a heterologous polypeptide, such as in the case of a fusion protein containing a first polypeptide consisting or a first sequence that is linked (via peptide bond) to a heterologous polypeptide consisting of a second sequence. In another example, the N- or C-terminus of a polypeptide that consists of or consists essentially of a particular amino acid sequence can be linked to a peptide linker (via peptide bond) that is further linked to one or more additional heterologous polypeptides. In a further example, the N- or C-terminus of a polypeptide that consists of or consists essentially of a particular amino acid sequence can be linked to one or more amino acid residues that facilitate further modification or manipulation of the polypeptide.

Control: A reference standard. In some embodiments, the control is a negative control, such as sample obtained from a healthy patient not infected with EBOV. In other embodiments, the control is a positive control, such as a tissue sample obtained from a patient diagnosed with EBOV infection. In still other embodiments, the control is a historical control or standard reference value or range of values (such as a previously tested control sample, such as a group of EBOV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Ebolavirus: A genus of enveloped, non-segmented, negative-sense, single-stranded RNA viruses that cause ebolavirus disease (EVD), formerly known as Ebola hemorrhagic fever (EHF), in humans. Ebolaviruses spread through human-to-human transmission, with infection resulting from direct contact with blood, secretions, organs or other bodily fluids of infected people, and indirect contact with environments contaminated by such fluids. These may include other Filoviruses.

The symptoms of ebolavirus infection and EVD are well-known. Briefly, in humans, ebolavirus has an initial incubation period of 2 to 21 days (7 days on average, depending on the species) followed by a rapid onset of non-specific symptoms such as fever, extreme fatigue, gastrointestinal complaints, abdominal pain, anorexia, headache, myalgias and/or arthralgias. These initial symptoms last for about 2 to 7 days after which more severe symptoms related to hemorrhagic fever occur, including hemorrhagic rash, epistaxis, mucosal bleeding, hematuria, hemoptysis, hematemesis, melena, conjunctival hemorrhage, tachypnea, confusion, somnolence, and hearing loss. In general, the symptoms last for about 7 to 14 days after which recovery may occur. Death can occur 6 to 16 days after the onset of symptoms. People are infectious as long as their blood and secretions contain the virus, which in some instances can be more than 60 days.

Immunoglobulin M (IgM) antibodies to the virus appear 2 to 9 days after infection whereas immunoglobulin G (IgG) antibodies appear approximately 17 to 25 days after infection, which coincides with the recovery phase. In survivors of EVD, both humoral and cellular immunity are detected, however, their relative contribution to protection is unknown.

Five distinct species of Ebolavirus are known, including Bundibugyo ebolavirus, Reston ebolavirus, Sudan ebolavirus, Taï Forest ebolavirus, and Zaire ebolavirus. Bundibugyo ebolavirus, Sudan ebolavirus, and Zaire ebolavirus have been associated with large outbreaks of EVD in Africa and reported case fatality rates of up to 90%. Exemplary amino acid sequences of GP from Bundibugyo ebolavirus, Reston ebolavirus, Sudan ebolavirus, Taï Forest ebolavirus, and Zaire ebolavirus are set forth as SEQ ID NOs: 25-29.

The ebolavirus genome includes about 19 kb, which encode seven structural proteins including NP (a nucleoprotein), VP35 (a polymerase cofactor), VP30 (a transcriptional activator), VP24, L (a RNA polymerase), and GP (a glycoprotein).

Ebolavirus glycoprotein (GP): The virion-associated transmembrane glycoprotein of Ebolavirus is initially synthesized as a precursor protein of about 676 amino acids in size, designated $GP_0$. Individual $GP_0$ polypeptides form a homotrimer and undergo glycosylation as well as processing to remove the signal peptide, and cleavage by a cellular protease between approximately positions 501/502 to generate separate $GP_1$ and $GP_2$ polypeptide chains, which remain associated via disulfide bonds as $GP_1/GP_2$ protomers within the homotrimer. The extracellular $GP_1$ trimer (approx. 140 kDa) is derived from the amino-terminal portion of the $GP_0$ precursors, and the GP2 trimer (approx. 26 kDa), which includes extracellular, transmembrane, and cytosolic domains, is derived from the carboxyl-terminal portion of the $GP_0$ precursors. $GP_1$ is responsible for attachment to new host cells while $GP_2$ mediates fusion with those cells.

Comparisons of the predicted amino acid sequences for the GPs of the different ebolaviruses show conservation of amino acids in the amino-terminal and carboxy-terminal regions with a highly variable region in the middle of the protein (Feldmann el al., Virus Res. 24: 1-19, 1992). The GPs of the ebolaviruses are highly glycosylated and contain both N-linked and O-linked carbohydrates that contribute up to 50% of the molecular weight of the protein. Most of the glycosylation sites are found in the central variable region of GP.

The numbering used in the disclosed filovirus GPs and fragments thereof is relative to the Zaire ebolavirus GP protein set forth as SEQ ID NO: 35, unless context indicates otherwise.

Effective amount: An amount of agent, such as an immunogen, that is sufficient to generate a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to generate a protective immune response.

In one example, a desired response is to induce an immune response that inhibits or prevents Ebola virus infection in a subject. For example, administration of an effective amount of a disclosed ebolavirus GP peptide can induce an immune response in a subject that inhibits subsequent infection of the subject by an ebolavirus.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include cosmids, plasmids (e.g., naked or contained in liposomes) and viruses (e.g., lentiviruses, retroviruses, adenoviruses, and adeno-associated viruses) that incorporate the recombinant polynucleotide.

Heterologous: Originating from a different genetic source. A nucleic acid molecule that is heterologous to a cell originated from a genetic source other than the cell in which it is expressed. Methods for introducing a heterologous nucleic acid molecule in a cell or organism include, for example, transformation with a nucleic acid, including electroporation, lipofection, particle gun acceleration, and homologous recombination.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen.

Immunogenic composition: A composition comprising a disclosed immunogen, or a nucleic acid molecule or vector encoding a disclosed immunogen, that elicits a measurable CTL response against the immunogen, or elicits a measurable B cell response (such as production of antibodies) against the immunogen, when administered to a subject. It further refers to isolated nucleic acids encoding an immunogen, such as a nucleic acid that can be used to express the immunogen (and thus be used to elicit an immune response against this immunogen). For in vivo use, the immunogenic composition will typically include the protein or nucleic acid molecule in a pharmaceutically acceptable carrier and may also include other agents, such as an adjuvant.

Inhibiting a disease or condition: Reducing the full development of a disease or condition in a subject, for example, reducing the full development of Ebola virus disease in a subject who has an Ebola virus infection, and/or reducing Ebola virus infection in a subject or population of subjects at risk thereof. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example, by vaccinating a subject at risk of EBOV infection, but not infected by EBOV, with an ebolavirus GP peptide immunogen as disclosed herein) that reduces subsequent development of the disease or condition, and also to amelioration of one or more signs or symptoms of the disease or condition following development. The term "ameliorating," with reference to inhibiting a disease or condition refers to any observable beneficial effect of the intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters well known in the art that are specific to the particular disease or condition.

In some embodiments, an immune response induced by administering an effective amount of an ebolavirus GP peptide immunogen as disclosed herein inhibits infection of a human subject by ebolaviruses, for example, by at least 50% (such as at least 60%, at least 70%, at least 80%, at least 90%, or more) compared to a suitable control.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker". In several embodiments, linked components are associated in a chemical or physical manner so that the components are not freely dispersible from one another, at least until contacting or entering a cell, such as an immune cell.

Linker: One or more molecules or groups of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Peptide: A polymer in which the monomers are amino acid residues that are joined together through amide bonds. The amino acids included in a peptide may be subject to post-translational modification (e.g., glycosylation or phosphorylation). A "residue" refers to an amino acid or amino acid mimetic incorporated in a peptide by an amide bond or amide bond mimetic. A peptide has an amino terminal (N-terminal) end and a carboxy terminal (C-terminal) end. In some embodiments, a peptide can In some embodiments, a peptide is at most 100 amino acids in length, such as at most 75 amino acids in length, such as at most 50 amino acids in length or at most 40 amino acids in length for example.

Peptide Modifications: Synthetic embodiments of the peptides described herein are also provided. For example, peptides can be modified by a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Each peptide of this disclosure is comprised of a sequence of amino acids, which may be either L- and/or D-amino acids, naturally occurring and otherwise.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Prime-boost immunization: An immunotherapy including administration of multiple immunogens over a period of time to elicit the desired immune response.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Homologs and variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. These sequence identity ranges are provided for guidance only; it is entirely possible that strongly significant homologs could be obtained that fall outside of the ranges provided.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen) and does not bind in a significant amount to other proteins or polysaccharides present in the sample or subject. Specific binding can be determined by standard methods. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Subject: Living multicellular vertebrate organisms, a category that includes human and non-human mammals. In an example, a subject is a human. In an additional example, a subject is selected that is in need of inhibiting an ebolavirus infection. For example, the subject is uninfected and at risk of ebolavirus infection.

Under conditions sufficient for: A phrase that is used to describe any environment that permits a desired activity.

Vector: An entity containing a DNA or RNA molecule bearing a promoter(s) that is operationally linked to the coding sequence of an immunogenic protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses.

A non-limiting example of a DNA-based expression vector is pCDNA3.1, which can include includes a mammalian expression enhancer and promoter (such as a CMV promoter). Non-limiting examples of viral vectors include adeno-associated virus (AAV) vectors as well as Poxvirus vector (e.g., Vaccinia, MVA, avian Pox, or Adenovirus).

II. Filovirus GP Peptides

Isolated peptides containing fragments of filovirus GP proteins are disclosed herein that can be used to induce an immune response in a subject that neutralizs filovirus infection (such as Zaire ebolavirus infection. As discussed in the Examples, the isolated peptides contain antigenic sites of the filovirus GP that are targeted by neutralizing antibodies and are shown to induce an immune response in a subject that neutralizing filovirus infection (such as Zaire ebolavirus infection).

In several embodiments, the isolated peptides contain fragments of an ebolavirus GP, such as GP from one of Zaire ebolavirus, Bundibugyo ebolavirus, Sudan ebolavirus, or Tai Forest ebolavirus. Exemplary ebolavirus GP protein sequences are set forth herein as SEQ ID NOs: 34-41. In some embodiments, the isolated peptides contain fragments of a Marburg margburgvirus GP An exemplary Marburg margburgvirus GP protein sequence is set forth herein as SEQ ID NO: 42. In further embodiments, the isolated peptide contains a fragment of a GP from another Filovirus species.

In some embodiments, the isolated peptide comprises, consists essentially of, or consists of 10-100 consecutive amino acids or longer (such as 10-15, 10-20, 10-30, 10-40, 10-50, 20-30, 20-40, 20-50, 30-50, 40-50, 10-75, 20-75, 20-75, 20-75, 30-75, 40-75, 50-75, or 75-100 consecutive amino acids) from a native filovirus GP sequence, such as a GP sequence set forth as any one of SEQ ID NOs: 34-42. In some embodiments the isolated peptide is no more than 100 amino acids in length, such as no more than 75, or no more than 50, or no more than 40 amino acids in length.

The isolated peptide includes the amino acid sequence of an antigenic site of the filovirus GP. For example, the isolated peptide comprises, consists essentially of, or consists of the amino acid sequence of any one of the antigenic sites of Zaire ebolavirus as set forth in FIG. 20, such as Antigenic site 11.1, 11.2, 11.3, 111.1, 111.2, IV.1, IV.2, IV.3, IV.4, IV.5, V.1, V.2, V.3, V.4, V.5, V.6, V.7, V.8, V.9. V.10, V.11, or VI. The sequences of antigenic sites shown in FIG. 20 correspond to the Zaire ebolavirus Mayinga GP sequence set forth as SEQ ID NO: 35. Due to the sequence homology of GP across filoviruses (see the filovirus GP sequence alignment provided in FIGS. 19A-19C), the antigenic sites provided in FIG. 20 can readily be identified in other filovirus GP sequences, for example, a GP from any of Zaire ebolavirus, Bundibugyo ebolavirus, Sudan ebolavirus, or Tai Forest ebolavirus, or Marburg margburgvirus, such as a GP protein sequence is set forth any one of SEQ ID NOs: 34-42, or other Filovirus strains In some embodiments, the isolated peptide comprises, consists essentially of, or consists of the amino acid sequence of the antigenic site VI residues from a filovirus GP, such as an ebolavirus GP or Marburgvirus GP. In some embodiments, the isolated peptide comprises, consists essentially of, or consists of the amino acid sequence set forth as SEQ ID NO: 9: KNITDKIX$_1$QIIHDFX$_2$DX$_3$X$_4$TLPX$_5$QX$_6$X$_7$X$_8$X$_9$NWW, wherein X$_1$ is D or N, X$_2$ is V or I, X$_3$ is K or N, X$_4$ is T, P, or N, X$_5$ is D or N, X$_6$ is G, T, D, or N, X$_7$ is D or N, X$_8$ is N, D, or G, and X$_9$ is D or S, wherein the peptide is no more than 100 (such as no more than 75, 50, 40, or 30) amino acids in length and induces a neutralizing immune response to filovirus (such as ebolavirus) in a subject. SEQ ID NO: 9 is a consensus amino acid sequence encompassing the amino acids of antigenic site VI from GP of Zaire ebolavirus (Mayinga, Kikwit, and Makona), Bundibugyo ebolavirus, Sudan ebolavirus, and Tai Forest ebolavirus. For example, the isolated peptide comprises, consists essentially of, or consists of the amino acid sequence set forth as any one of SEQ ID NOs: 10-13. In further embodiments, the isolated peptide comprises, consists essentially of, or consists of the amino acid sequence of the antigenic site VI from a Margurg Marburgvirus, such as the Antigenic site VI sequence set forth as SEQ ID NO: 53.

In some embodiments, the isolated peptide comprises, consists essentially of, or consists of the amino acid sequence set forth as SEQ ID NO: 7: KNITDKIX$_1$QIIHDFX$_2$DX$_3$X$_4$TLPX$_5$QX$_6$X$_7$X$_8$X$_9$NWWT, wherein: X$_1$ is D or N, X$_2$ is V and I, X$_3$ is K or N, X$_4$ is T, P, or N, X$_5$ is D or N, X$_6$ is G, T, D, or N, X$_7$ is D or N, X$_8$ is N, D, or G; and X$_9$ is D or S, wherein the peptide is no more than 100 (such as no more than 75, 50, 40, or 30) amino acids in length and induces a neutralizing immune response to filovirus (such as ebolavirus) in a subject. SEQ ID NO: 7 is a consensus amino acid sequence encompassing the amino acids of antigenic site VI from GP of Zaire ebolavirus (Mayinga, Kikwit, and Makona), Bundibugyo ebolavirus, Sudan ebolavirus, and Tai Forest ebolavirus. For example, the isolated peptide comprises, consists essentially of, or consists of the amino acid sequence set forth as any one of SEQ ID NOs: 4, or 14-16. In further embodiments, the isolated peptide comprises, consists essentially of, or consists of the amino acid sequence of the antigenic site VI from a Margurg Marburgvirus, such as the Antigenic site VI sequence set forth as SEQ ID NO: 54.

In some embodiments, the isolated peptide comprises, consists essentially of, or consists of the amino acid sequence of the antigenic site VIA residues from a filovirus GP, such as an ebolavirus GP or Marburgvirus GP. In some embodiments, the isolated peptide comprises, consists essentially of, or consists of the amino acid sequence set forth as SEQ ID NO: 6 (FX$_2$DX$_3$X$_4$TLPX$_5$QX$_6$X$_7$X$_8$X$_9$NWWT, wherein: X$_2$ is selected from V and I; X$_3$ from K and N; X$_4$ from T, P, and N; X$_5$ and X$_7$ from D and N; X$_6$ from G, T, D, and N; X$_8$ from N, D, and G; and X$_9$ from D and S, wherein the peptide is no more than 100 (such as no more than 75, 50, 40, or 30) amino acids in length and induces a neutralizing immune response to filovirus (such as ebolavirus) in a subject. SEQ ID NO: 6 is a consensus amino acid sequence encompassing a C-terminal portion of antigenic site VIA from GP of Zaire ebolavirus (Mayinga, Kikwit, and Makona), Bundibugyo ebolavirus, Sudan ebolavirus, and Tai Forest ebolavirus. For example, the isolated peptide comprises, consists essentially of, or consists of the amino acid sequence set forth as any one of SEQ ID NOs: 5, or residues 14-30 of SEQ ID NOs: 14-16 or 54.

In some embodiments, the isolated peptide comprises, consists essentially of, or consists of the amino acid sequence of the antigenic site IV.1 residues from a filovirus GP, such as an ebolavirus GP or Marburgvirus GP. In some embodiments, the isolated peptide comprises, consists essentially of, or consists of the amino acid sequence set forth as any one of SEQ ID NOs: 17-20, wherein the peptide is no more than 100 (such as no more than 75, 50, 40, or 30) amino acids in length and induces a neutralizing immune response to filovirus (such as ebolavirus) in a subject. SEQ ID NOs: 17-20 encompass the amino acids of antigenic site IV.1 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site VI from a Margurg Marburgvirus, such as the Antigenic site IV.1 sequence set forth as SEQ ID NO: 58.

In some embodiments, the isolated peptide comprises, consists essentially of, or consists of the amino acid sequence of the antigenic site V.1 residues from a filovirus GP, such as an ebolavirus GP or Marburgvirus GP. In some embodiments, the isolated peptide comprises, consists essentially of, or consists of the amino acid sequence set forth as any one of SEQ ID NOs: 21-25, wherein the peptide is no more than 100 (such as no more than 75, 50, 40, or 30) amino acids in length and induces a neutralizing immune response to filovirus (such as ebolavirus) in a subject. SEQ ID NOs: 21-25 encompass the amino acids of antigenic site V.1 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site VI from a Margurg Marburgvirus, such as the Antigenic site V.1 sequence set forth as SEQ ID NO: 59.

In some embodiments, the isolated peptide comprises, consists essentially of, or consists of the amino acid sequence of the antigenic site V.6 residues from a filovirus GP, such as an ebolavirus GP or Marburgvirus GP. In some embodiments, the isolated peptide comprises, consists essentially of, or consists of the amino acid sequence set forth as any one of SEQ ID NOs: 2, 26-28, or 43-46 wherein the peptide is no more than 100 (such as no more than 75, 50, 40, or 30) amino acids in length and induces a neutralizing immune response to filovirus (such as ebolavirus) in a subject. SEQ ID NOs: 2, 26-28, and 43-46 encompass the amino acids of antigenic site V.6 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site VI from a Margurg Marburgvirus, such as the Antigenic site V.6 sequence set forth as SEQ ID NO: 56.

In some embodiments, the isolated peptide comprises, consists essentially of, or consists of the amino acid sequence of the antigenic site V.7 residues from a filovirus GP, such as an ebolavirus GP or Marburgvirus GP. In some embodiments, the isolated peptide comprises, consists essentially of, or consists of the amino acid sequence set forth as any one of SEQ ID NOs: 3 or 32-34, wherein the peptide is no more than 100 (such as no more than 75, 50, 40, or 30) amino acids in length and induces a neutralizing immune response to filovirus (such as ebolavirus) in a subject. SEQ ID NOs: 3 and 32-34 encompass the amino acids of antigenic site V.7 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site V.7 from a Margurg Marburgvirus, such as the Antigenic site VI sequence set forth as SEQ ID NO: 55.

In some embodiments, the isolated peptide comprises, consists essentially of, or consists of the amino acid sequence of the antigenic site V.10 residues from a filovirus GP, such as an ebolavirus GP or Marburgvirus GP. In some embodiments, the isolated peptide comprises, consists essentially of, or consists of the amino acid sequence set forth as any one of SEQ ID NOs: 29-31, wherein the peptide is no more than 100 (such as no more than 75, 50, 40, or 30) amino acids in length and induces a neutralizing immune response to filovirus (such as ebolavirus) in a subject. SEQ ID NOs: 29-31 encompass the amino acids of antigenic site V.10 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site V.10 from a Margurg Marburgvirus, such as the Antigenic site VI sequence set forth as SEQ ID NO: 60.

In some embodiments, the isolated peptide comprises, consists essentially of, or consists of the amino acid sequence of a portion of antigenic site V residues from a filovirus GP, such as an ebolavirus GP or Marburgvirus GP. In some embodiments, the isolated peptide comprises, consists essentially of, or consists of the amino acid sequence set forth as SEQ ID NO: 8: TX$_{10}$EDHKIMASENSSAMVQVHSQGRX$_{11}$AAVSH wherein: X$_{10}$ is T or N; and X$_{11}$ is E or K, wherein the peptide is no more than 100 (such as no more than 75, 50, 40, or 30) amino acids in length and induces a neutralizing immune response to filovirus (such as ebolavirus) in a subject. SEQ ID NO: 8 is a consensus amino acid sequence including a portion of antigenic site V from GP of Zaire ebolavirus (Mayinga, Kikwit, and Makona), Bundibugyo ebolavirus, Sudan ebolavirus, and Tai Forest ebolavirus. For example, the isolated peptide comprises, consists essentially of, or consists of the amino acid sequence set forth as SEQ ID NO: 1.

In some embodiments, the isolated peptide comprises, consists essentially of, or consists of the amino acid sequence of antigenic site II.1 residues from a filovirus GP, such as an ebolavirus GP or Marburgvirus GP. In some embodiments, the isolated peptide comprises, consists essentially of, or consists of the amino acid sequence set forth as any one of SEQ ID NOs: 47-50, wherein the peptide is no more than 100 (such as no more than 75, 50, 40, or 30) amino acids in length and induces a neutralizing immune response to filovirus (such as ebolavirus) in a subject. SEQ ID NOs: 47-50 encompass the amino acids of antigenic site II.1 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site VI from a Margurg Marburgvirus, such as the Antigenic site II.1 sequence set forth as SEQ ID NO: 61.

In some embodiments, the isolated peptide comprises, consists essentially of, or consists of the amino acid sequence of the antigenic site IV.2 residues from a filovirus GP, such as an ebolavirus GP or Marburgvirus GP. In some embodiments, the isolated peptide comprises, consists essentially of, or consists of the amino acid sequence set forth as any one of SEQ ID NOs: 51-52, wherein the peptide is no more than 100 (such as no more than 75, 50, 40, or 30) amino acids in length and induces a neutralizing immune response to filovirus (such as ebolavirus) in a subject. SEQ ID NOs: 51-51 encompass the amino acids of antigenic site IV.2 from GP of Zaire ebolavirus (Mayinga, Kikwit, and Makona), Bundibugyo ebolavirus, Sudan ebolavirus, and Tai Forest ebolavirus or other Filoviruses. In further embodiments, the isolated peptide comprises, consists essentially of, or consists of the amino acid sequence of the antigenic site VI from a Margurg Marburgvirus, such as the Antigenic site IV.2 sequence set forth as SEQ ID NO: 62.

Any of the isolated peptides disclosed herein can be conjugated to a carrier molecule, for example, to enhance the immune response in a subject to the peptide. The peptide can be directly conjugated to the carrier or indirectly via a linker.

In some examples, the peptide and the carrier are linked by a linker between a lysine amino acid residue present on the carrier protein and a cysteine amino acid residue fused (by a peptide bond) to the C-terminal residue of the peptide.

Suitable linkers include, but are not limited to, straight or branched-chain carbon linkers, heterocyclic carbon linkers or peptide linkers. For an immunogenic conjugate from two or more constituents, each of the constituents will contain the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. Likewise, a wide variety of linking groups may be employed. In some cases, the linking group can be designed to be either hydrophilic or hydrophobic in order to enhance the desired binding characteristics of the peptide and the carrier. The covalent linkages should be stable relative to the solution conditions under which the conjugate is subjected.

In some embodiments, the linkers may be joined to the constituent amino acids through their side chains (such as through a disulfide linkage to cysteine) or to the alpha carbon, amino, and/or carboxyl groups of the terminal amino acids. In some embodiments, the linker, the peptide, and the carrier can be encoded as a single peptide such that the peptide and the carrier are joined by peptide bonds.

The procedure for attaching a carrier molecule to a peptide varies according to the chemical structure of the molecules. Peptides typically contain a variety of functional groups; for example, carboxylic acid (COOH), free amine (—NH$_2$) or sulfhydryl (—SH) groups, which are available for reaction with a suitable functional group on a peptide. Alternatively, the peptide is derivatized to expose or attach additional reactive functional groups. The derivatization may involve attachment of any of a number of linker molecules such as those available from Pierce Chemical Company, Rockford, Ill.

In some embodiments, a sulfosuccinimidyl (4-iodoacetyl) aminobenzoate (Sulfo-SIAB) linker is used to link the peptide to carrier. In some embodiments an m-maleimido-benzoyl-N-hydroxysuccinimide ester (MBS) linker is used to attach the peptide to carrier.

Any specific combination of peptide and carrier may be selected from the specific peptides and carrier that are listed herein.

It can be advantageous to produce conjugates in which more than one peptide as described herein is conjugated to a single carrier protein. In several embodiments, the conjugation of multiple peptides to a single carrier protein is possible because the carrier protein has multiple lysine or cysteine side-chains that can serve as sites of attachment. The amount of peptide reacted with the amount of carrier may vary depending upon the specific peptide and the carrier. In some embodiments, from 1 to 30, such as about 1, about 5, about 10, about 15, about 20, or about 30 peptides, or more, can be linked to each carrier protein molecule. In some embodiments (such as when KLH is used as a carrier, from 1 to 1000, such as about 10, about 20, about 30, about 40, about 50, about 100, about 200, about 300, about 400, about 500, about 700, or about 1000 peptides can be linked to each carrier protein molecule. "About" in this context refers to plus or minus 5% when measuring an average number of X peptide molecules per carrier molecule in the conjugate.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. Carriers that fulfill these criteria are available (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000). A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601, 826 and 6,696,065); diphtheria toxin/toxoid (for example, as described in U.S. Pat. Nos. 4,709,017 and 6,696,065), such as tetanus toxin heavy chain C fragment; *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817, 317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos.

4,547,367 and 4,547,368) can also be used as carriers, as well as proteins from higher organisms such as keyhole limpet hemocyanin (KLH), horseshoe crab hemocyanin, Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: Keyhole Limpet Hemocyanin (KLH), tetanus toxoid, tetanus toxin heavy chain C fragment, diphtheria toxoid, diphtheria toxin variant CRM197, or H influenza protein D (HiD). CRM197 is a genetically detoxified form of diphtheria toxin; a single mutation at position 52, substituting glutamic acid for glycine, causes the ADP-ribosyltransferase activity of the native diphtheria toxin to be lost. For description of protein carriers for vaccines, see Pichichero, Protein carriers of conjugate vaccines: characteristics, development, and clinical trials, Hum Vaccin Immunother., 9: 2505-2523, 2013, which is incorporated by reference herein in its entirety).

Following conjugation of the peptide to the carrier protein, the conjugate can be purified by appropriate techniques. One goal of the purification step is to separate the unconjugated peptide or carrier from the conjugate. One method for purification, involving ultrafiltration in the presence of ammonium sulfate, is described in U.S. Pat. No. 6,146,902. Alternatively, the conjugates can be purified away from unconjugated peptide or carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry, for example.

In several embodiments, the disclosed immunogenic conjugates can be formulated into an immunogenic composition (such as vaccines), for example by the addition of a pharmaceutically acceptable carrier and/or adjuvant.

III. Polynucleotides and Expression

Polynucleotides encoding the disclosed peptides are also provided. These polynucleotides include DNA, cDNA and RNA sequences which encode the peptide. The genetic code can be used to construct a variety of functionally equivalent nucleic acids, such as nucleic acids that differ in sequence but which encode the same protein sequence.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed peptide can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed peptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signals for introns, maintenance of the correct reading frame of that gene to permit proper translation of mRNA, and stop codons.

DNA sequences encoding the disclosed peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human) Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques. In some embodiments, if the host is prokaryotic, such as, but not limited to, *E. coli*, competent cells which are capable of DNA uptake can be prepared from cells harvested after exponential growth phase and subsequently treated by the $CaCl_2$ method. Alternatively, $MgCl_2$ or RbC1 can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines can be utilized.

Modifications can be made to a nucleic acid encoding a disclosed peptide without diminishing its biological activity. Some modifications can be made to facilitate the cloning, expression, or incorporation of the peptide into a fusion protein. Non-limiting examples of such modifications include termination codons, a methionine added at the amino terminus to provide an initiation site, additional amino acids placed on either terminus to create conveniently located restriction sites, or additional amino acids (such as poly His) to aid in purification steps.

IV. Viral Vectors

A nucleic acid molecule encoding a disclosed peptide can be included in a viral vector, for example, for expression of the immunogen in a host cell, or for immunization of a subject as disclosed herein. In some embodiments, the viral vectors are administered to a subject as part of a prime-boost immunization. In several embodiments, the viral vectors used in a prime-boost immunization protocol to prime an immune response to ebolavirus GP or boost an immune response to ebolavirus GP.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed that can be used to express the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

VI. Immunogenic Compositions

Immunogenic compositions comprising a disclosed peptide (for example, linked to a carrier) or a nucleic acid molecule or vector encoding the peptide and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. Actual methods for preparing administrable compositions are described in more detail in such publications as *Remingtons Pharmaceutical Sciences, 19$^{th}$ Ed.*, Mack Publishing Company, Easton, Pa., 1995.

The peptide (for example, linked to a carrier) or a nucleic acid molecule or vector encoding the peptide can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.) may also be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the immunogenic composition can be provided as a sterile composition. The immunogenic composition typically contains an effective amount of a disclosed peptide (for example, linked to a carrier) or a nucleic acid molecule or vector encoding the peptide, and can be prepared by conventional techniques. Typically, the amount of a disclosed peptide (for example, linked to a carrier) or a nucleic acid molecule or vector encoding the peptide in each dose of the immunogenic composition is selected as an amount which elicits an immune response without significant, adverse side effects. In some embodiments, the immunogenic composition can be provided in unit dosage form for use to elicit an immune response in a subject, for example, to prevent ebolavirus infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VII. Methods of Inducing an Immune Response

An immunogenic composition comprising a disclosed filovirus GP (e.g., Zaire ebolavirus GP) peptide, a nucleic acid molecule (such as an RNA molecule) encoding a disclosed filovirus GP (e.g., Zaire ebolavirus GP) peptide, vector including the nucleic acid molecule, or immunogenic composition, can be administered to a subject to induce an immune response to filovirus GP (e.g., Zaire ebolavirus GP) in the subject. In a particular example, the subject is a human. The immune response can be a protective immune response, for example a response that inhibits subsequent infection with a filovirus (such as a Zaire ebolavirus). Elicitation of the immune response can also be used to treat or inhibit infection and illnesses associated with a filovirus (such as a Zaire ebolavirus).

A subject can be selected for immunization that has, or is at risk for developing infection or illness associated with a filovirus (such as a Zaire ebolavirus), for example because of exposure or the possibility of exposure to a filovirus (such as a Zaire ebolavirus).

Typical subjects intended for administration of the immunogenic composition include humans, as well as non-human primates and other animals. To identify relevant subjects, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize a filovirus (such as a Zaire ebolavirus) infection. These and other routine methods allow the clinician to select patients in need of therapy. In accordance with these methods and principles, the immunogenic composition can be administered according to the teachings herein, or other conventional methods, as an independent prophylaxis or treatment program, or as a follow-up, adjunct or coordinate treatment regimen to other treatments.

The administration of the immunogenic composition can be for prophylactic or therapeutic purpose. When provided prophylactically, the immunogenic composition can be provided in advance of any symptom, for example, in advance of infection. The prophylactic administration serves to prevent or ameliorate any subsequent infection. In some embodiments, the methods can involve selecting a subject at risk for contracting filovirus infection (e.g., Zaire ebolavirus infection), and administering an effective amount of the immunogenic composition to the subject. The immunogenic composition can be provided prior to the anticipated exposure to filovirus infection (e.g., Zaire ebolavirus infection) so as to attenuate the anticipated severity, duration or extent of an infection and/or associated disease symptoms, after exposure or suspected exposure to the virus, or after the actual initiation of an infection.

The immunogenic composition is provided to the subject in an amount effective to induce or to enhance an immune response against filovirus GP (e.g., Zaire ebolavirus GP) in the subject, preferably a human. The actual dosage of the immunogenic composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to filovirus GP (e.g., Zaire ebolavirus GP). Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of filovirus infection (e.g., Zaire ebolavirus infection) or improvement in disease state (e.g., reduction in viral load). If such monitoring indicates that vaccination is sub-optimal, the subject can be boosted with an additional dose of immunogenic composition, and the vaccination parameters can be modified in a manner expected to potentiate the immune response.

In some embodiments, the prime-boost method can include DNA-prime and protein-boost vaccination protocol to a subject. The method can include two or more administrations of the nucleic acid molecule or the protein.

For peptide therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg.

The amount utilized in an immunogenic composition is selected based on the subject population (e.g., infant or elderly). An optimal amount for a particular composition can be ascertained by standard studies involving observation of antibody titers and other responses in subjects. It is understood that an effective amount of a disclosed immunogenic composition can include an amount that is ineffective at eliciting an immune response by administration of a single dose, but that is effective upon administration of multiple dosages, for example in a prime-boost administration protocol.

Upon administration of the immunogenic composition, the immune system of the subject typically responds to the immunogenic composition by producing antibodies specific for viral protein. Such a response signifies that an immunologically effective dose was delivered to the subject.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, filovirus GP (e.g., Zaire ebolavirus GP).

Filovirus infection (e.g., Zaire ebolavirus infection) does not need to be completely eliminated or reduced or prevented for the methods to be effective. For example, elicitation of the immune response can reduce or inhibit infection with the Filovirus (e.g., Zaire ebolavirus) by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to infection with the Filovirus (e.g., Zaire ebolavirus) in the absence of the immunization.

One approach to administration of nucleic acids is direct immunization with plasmid DNA, such as with a mammalian expression plasmid Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In some embodiments, a plasmid DNA vaccine is used to express a disclosed filovirus GP peptide (e.g., Zaire ebolavirus GP peptide) in a subject. For example, a nucleic acid molecule encoding a disclosed filovirus GP peptide (e.g., Zaire ebolavirus GP peptide) can be administered to a subject to induce an immune response to filovirus GP (e.g., Zaire ebolavirus GP).

In another approach, a disclosed filovirus GP peptide (e.g., Zaire ebolavirus GP peptide) can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991). These peptides can also be used in combination or with vaccines against other pathogens.

In one embodiment, a nucleic acid encoding a disclosed filovirus GP peptide (e.g., Zaire ebolavirus GP peptide) is introduced directly into cells to induce the immune response. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed filovirus GP peptide (e.g., Zaire ebolavirus GP peptide) directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed filovirus GP peptide (e.g., Zaire ebolavirus GP peptide) include conventional non-amplifying mRNA immunization (see, e.g., Petsch et al., "Protective efficacy of in vitro synthesized, specific mRNA vaccines against influenza A virus infection," Nature biotechnology, 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

In some embodiments, administration of an effective amount of one or more of the disclosed immunogens to a subject induces a neutralizing or protective immune response in the subject. To assess neutralization activity, following immunization of a subject, serum can be collected from the subject at appropriate time points, frozen, and stored for neutralization testing. Methods to assay for binding or neutralization activity are known to the person of ordinary skill in the art and are further described herein, and include, but are not limited to, ELISA, plaque reduction neutralization (PRNT) assays, microneutralization assays, flow cytometry based assays, single-cycle infection assays. In some embodiments, the serum neutralization activity can be assayed using a panel of filovirus (e.g., Zaire ebolavirus) pseudoviruses.

VIII. Methods of Detection and Diagnosis

Methods are also provided for the detection of the presence of antibodies to filovirus GP in a biological sample. The method can be used to identify a biological sample from a subject with a filovirus (such as ebolavirus) infection, or from a subject that had a prior infection with a filovirus (such as an ebolavirus). In one example, the presence of filovirus (for example, Zaire ebolavirus) GP is detected in a biological sample from a subject, and can be used to identify a subject with filovirus infection. The sample can be any sample form a subject that contains antibodies induced by the filovirus infection, including, but not limited to body fluids, such as blood, serum, plasma, sputum, spinal fluid or urine. The method of detection can include contacting the sample with an isolated filovirus peptide as disclosed herein and under conditions sufficient to form an immune complex between the peptide and the antibodies in the sample, and detecting the immune complex.

In some embodiments, the peptides disclosed herein are used to test vaccines. For example to test if a test vaccine elicits an immune response that targets a particular antigenic site on the filovirus GP, such as antigenic site VI of Zaire ebolavirus as disclosed herein. Such methods involve immunizing a subject with a vaccine, and then screening a sample from the subject that contains antibodies induced by the immunization for antibody binding to the appropriate peptide.

Thus, the peptides disclosed herein can be used for serodiagnosis as well as development of assays for evaluation of vaccine or therapeutics or countermeasures or effectivity of these approaches.

VIII. Additional Description of Certain Embodiments

The present disclosure provides an immunogenic composition for inducing an immune response. The present disclosure also relates to prophylactic uses of the immunogenic compositions, for use in eliciting antibodies to the immunogen. In certain embodiments, the present disclosure relates to immunogenic compositions that provide a method of treating or suppressing a Filovirus disease in a patient, the method comprising administering to a patient the immunogenic composition of the disclosure.

In certain embodiments, the present disclosure relates to an immunogenic composition comprising one or more peptide fragments of a filovirus protein for use in eliciting an immunogenic response in a mammal. In other embodiments, the immunogenic composition can further comprise carrier proteins conjugated to the peptide fragments. The immunogenic composition can further comprise an adjuvant.

In certain embodiments, the peptide fragment or peptide fragments comprise one or more of the amino acid sequences selected from the following group of amino acid sequences or variants thereof:

SEQ ID NO: 1: TTEDHKIMASENSSAMVQVHSQGREAAVSH

SEQ ID NO: 2: ETAGNNNTHHQDTGEESASSGKLGLITN

SEQ ID NO: 3: TGEESASSGKLGLITNTIAGVAGLITGGRR

SEQ ID NO: 4: KNITDKIDQIIHDFVDKTLPDQGDNDNWWT

SEQ ID NO: 5: FVDKTLPDQGDNDNWWT

SEQ ID NO: 6 (FX$_2$DX$_3$X$_4$TLPX$_5$QX$_6$X$_7$X$_8$X$_9$NWWT) wherein: X$_2$ is selected from V and I; X$_3$ from K and N; X$_4$ from T, P, and N; X$_5$ and X$_7$ from D and N; X$_6$ from G, T, D, and N; X$_8$ from N, D, and G; and X$_9$ from D and S.

SEQ ID NO: 7 (KNITDKIX$_1$QIIHDFX$_2$DX$_3$X$_4$TLPX$_5$QX$_6$X$_7$X$_8$X$_9$NWWT) wherein: X$_2$ is selected from V and I; X$_3$ from K and N; X$_4$ from T, P, and N; X$_1$, X$_5$ and X$_7$ from D and N; X$_6$ from G, T, D, and N; X$_8$ from N, D, and G; and X$_9$ from D and S.

SEQ ID NO: 8 (TX$_{10}$EDHKIMASENSSAMVQVHSQGRX$_{11}$AAVSH) wherein: X$_{10}$ is selected from T and N; and X$_{11}$ from E and K.

In certain embodiments, a non-limiting acceptable carrier molecule includes keyhole limpet hemocyanin (KLH), DNA vectors, lentiviral vectors, nanoparticles, vesicular stomatitis virus (VSV), bovine serum albumin, ovalbumin, fowl immunoglobulin, and cytosine-phosphate-guanine (CpG) oligodeoxynucleotides.

Clause 1. An immunogenic composition comprising a peptide fragment comprising an amino acid sequence of SEQ ID NO: 6 (FX$_2$DX$_3$X$_4$TLPX$_5$QX$_6$X$_7$X$_8$X$_9$NWWT) wherein: X$_2$ is selected from V and I; X$_3$ from K and N; X$_4$ from T, P, and N; X$_5$ and X$_7$ from D and N; X$_6$ from G, T, D, and N; X$_8$ from N, D, and G; and X$_9$ from D and S.

Clause 2. The immunogenic composition of Clause 1 wherein the peptide fragment comprises the amino acid sequence SEQ ID NO:5 (FVDKTLPDQGDNDNWWT).

Clause 3. An immunogenic composition comprising a peptide fragment comprising an amino acid sequence of SEQ ID NO: 7 (KNITDKIX$_1$QIIHDFX$_2$DX$_3$X$_4$TLPX$_5$QX$_6$X$_7$X$_8$X$_9$NWWT) wherein: X$_2$ is selected from V and I; X$_3$ from K and N; X$_4$ from T, P, and N; X$_1$, X$_5$ and X$_7$ from D and N; X$_6$ from G, T, D, and N; X$_8$ from N, D, and G; and X$_9$ from D and S.

Clause 4. The immunogenic composition of Clause 3 wherein the peptide fragment comprises the amino acid sequence SEQ ID NO: 4 (KNITDKIDQIIHDFVDKTLPDQGDNDNWWT).

Clause 5. An immunogenic composition comprising a peptide fragment comprises an amino acid sequence of SEQ ID NO: 8 (TX$_{10}$EDHKIMASENSSAMVQVHSQGRX$_{11}$AAVSH) wherein: X$_{10}$ is selected from T and N; and X$_{11}$ from E and K.

Clause 6. The immunogenic composition of Clause 5 wherein the peptide fragment comprises the amino acid sequence SEQ ID NO: 1 (TTEDHKIMASENSSA-MVQVHSQGREAAVSH).

Clause 7. An immunogenic composition comprising a peptide fragment comprising an amino acid sequence of SEQ ID NO: 2 (ETAGNNNTHHQDTGEE-SASSGKLGLITN).

Clause 8. An immunogenic composition comprising a peptide fragment comprising an amino acid sequence of SEQ ID NO: 3 (TGEESASSGKLGLITNTIAGVAGLITG-GRR).

Clause 9. An immunogenic composition comprising a peptide fragment comprising an amino acid sequence of SEQ ID NO: 5 or SEQ ID NO: 6 and a peptide fragment or peptide fragments selected from the list of peptide fragments encoded by amino acid sequences SEQ ID NO: 1, SEQ ID NO: 2, SEQ ID NO: 3, SEQ ID NO: 4, SEQ ID NO: 7, and SEQ ID NO: 8.

Clause 10. An immunogenic composition comprising a peptide fragment having amino acid sequence SEQ ID NO: 4 or SEQ ID NO: 7 and a peptide fragment or peptide fragments selected from the list of peptide fragments encoded by amino acid sequences SEQ ID NO: 1, SEQ ID NO: 2, SEQ ID NO: 3, SEQ ID NO: 5, SEQ ID NO: 6, and SEQ ID NO: 8.

Clause 11. An immunogenic composition comprising a peptide fragment or peptide fragments selected from the list of peptide fragments encoded by the amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

Clause 12. The immunogenic composition of Clauses 1-11 further comprising an adjuvant.

Clause 13. The immunogenic composition of Clause 12 where in the adjuvant is oil in water, CpG, or a carrier protein.

Clause 14. The immunogenic composition of Clauses 1-11 further comprising a carrier protein whereby the carrier protein is conjugated to each peptide fragment.

Clause 15. The immunogenic for composition of Clause 14 where in the carrier protein is keyhole limpet hemocyanin.

EXAMPLES

The following examples are provided to illustrate particular features of certain embodiments, but the scope of the claims should not be limited to those features exemplified.

Example 1

Human Antibody Repertoire after VSV-Ebola Vaccination Identifies Novel Targets and Virus-Neutralizing IgM Antibodies Development of an effective vaccine against Ebola virus is of high priority. However, knowledge about potential correlates of protection and the durability of immune response after vaccination is limited. Here, we elucidate the human antibody repertoire after administration of vesicular stomatitis virus (VSV)-Ebola vaccine at 3 million, 20 million and 100 million plaque-forming units (PFU) and homologous VSV-Ebola vaccine boost in healthy adult volunteers. Whole genome-fragment phage display libraries, expressing linear and conformational epitopes of Ebola glycoprotein (GP), showed higher diversity of antibody epitopes in individuals vaccinated with 20 million PFU than in those vaccinated with 3 million or 100 million PFU. Surface plasmon resonance kinetics showed higher levels of GP-binding antibodies after a single vaccination with 20 million or 100 million PFU than with 3 million PFU, and these correlated strongly with neutralization titers. A second vaccination did not boost antibody or virus neutralization titers, which declined rapidly, and induced only minimal antibody affinity maturation. Isotype analysis revealed a predominant IgM response even after the second vaccination, which contributed substantially to virus neutralization in vitro. These findings may help identify new vaccine targets and aid development and evaluation of effective countermeasures against Ebola.

The recent 2014 epidemic of highly pathogenic Ebola virus (EBOV) in Western Africa caused tens of thousands of infections and deaths. With occasional small outbreaks of new cases in Western Africa and the possibility of long-term persistence of virus in some survivors, it is feared that future outbreaks could occur and lead to severe epidemics. Therefore, development of an effective vaccine against Ebola is a high priority, both for pre-epidemic preparedness and for rapid vaccination to control future outbreaks. Protection against EBOV disease is attributed, at least partially, to the humoral immune response, as passive transfer of antibodies to naive NHPs can protect recipients against lethal EBOV challenge. Diverse ELISA, EBOV neutralization tests and immune parameters have been used to identify the vaccine correlates of protection (Matassov, D. et al. *J. Infect. Dis.* 212 (Suppl. 2), S443-S451, 2015; Blaney, J. E. et al. *PLoS Pathog.* 9, e1003389, 2013; and Wong, G. et al. *Sci. Transl. Med.* 4, 158ra146, 2012). A recent study also investigated the role of T cells in EBOV-infected patients and found that expression of the inhibitory molecules cytotoxic T lymphocyte-associated protein 4 (CTLA-4) and programmed cell death protein 1 (PD-1) on CD4+ and CD8+ T cells was lower in survivors than in fatal cases (Ruibal, P. et al. *Nature* 533, 100-104, 2016). However, to date, no single assay has been found to be predictive of protection, and the correlation of antibody titers measured by various assays has not been clearly demonstrated. Coupled with the difficulty of conducting adequate randomized controlled trials to demonstrate vaccine effectiveness on the basis of clinical EBOV disease, it is important to identify and understand immune markers that are reasonably likely to predict clinical benefit and can facilitate evaluation of vaccine candidates.

Recently, a recombinant VSV (rVSV)-based vaccine expressing Ebola Zaire surface glycoprotein from the Kikwit 1995 strain (rVSVΔG-ZEBOV-GP) was reported to decrease transmission to close contacts in a ring vaccination study in Guinea (Henao-Restrepo, A. M. et al. *Lancet* 386, 857-866, 2015). Here we performed an in-depth comprehensive analysis of the humoral immune response after primary rVSVΔG-ZEBOV-GP vaccination administered at 3 million, 20 million or 100 million PFU and homologous rVSVΔG-ZEBOV-GP vaccine boost in healthy US adult volunteers in a phase 1 placebo-controlled trial (Regules, J. A. et al. *N. Engl. J. Med.* 376(4):330-341, 2017, available online Apr. 1, 2015). Polyclonal serum was analyzed quantitatively and qualitatively to elucidate antibody epitope repertoires using gene-fragment phage display libraries (GFPDLs) and surface plasmon resonance (SPR) technology to measure realtime antibody binding kinetics, antibody cross-reactivity, immunoglobulin isotypes, affinity maturation and antibody persistence in recipients of the rVSVΔG-ZEBOV-GP vaccine.

Results
Antibody Epitope Repertoire after Vaccination

Figure 10A:
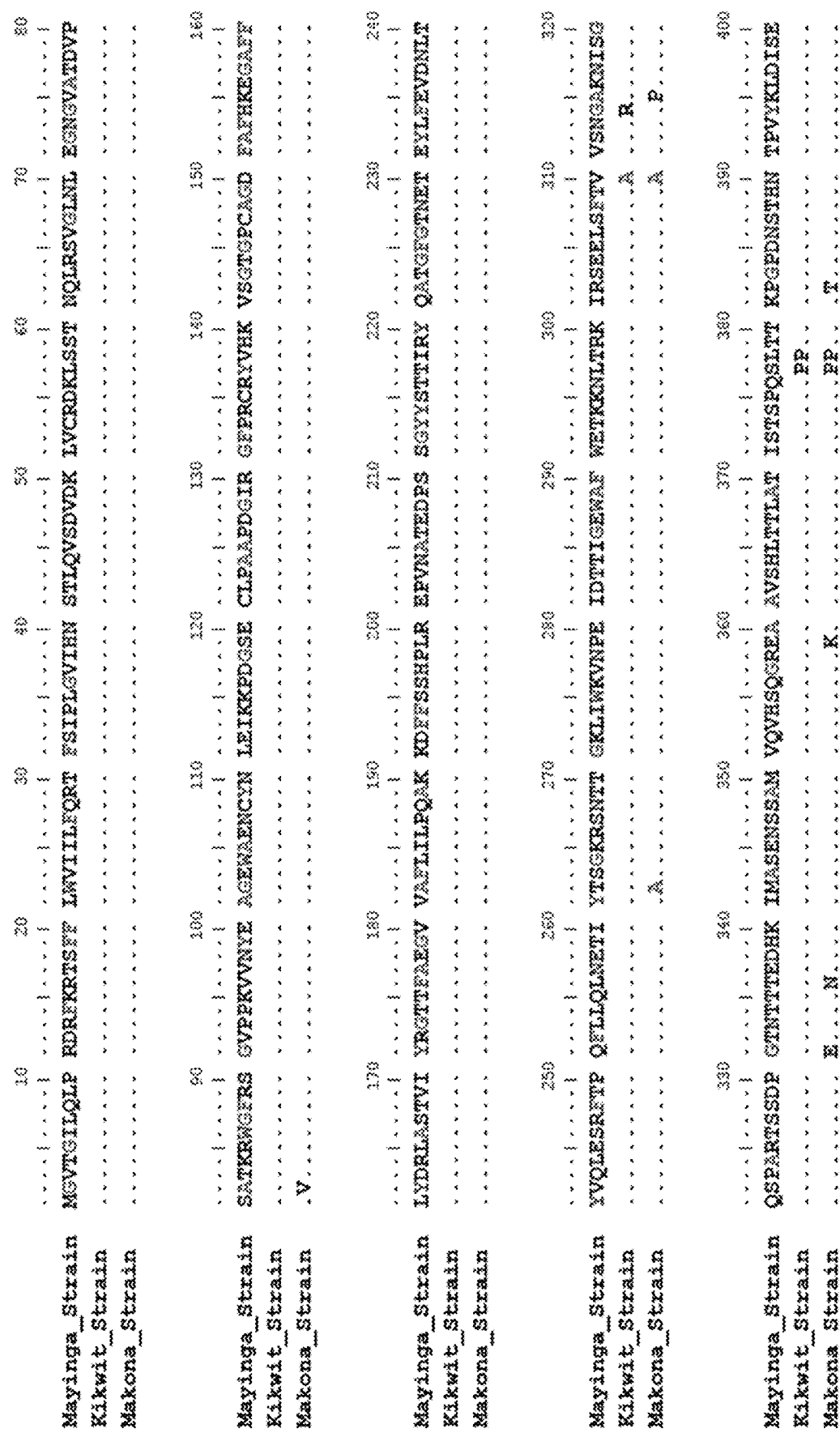

A rVSVΔG-ZEBOV-GP vaccine was administered intramuscularly at 3 million, 20 million or 100 million PFU to 39 healthy adult volunteers at the US National Institute of Allergy and Infectious Diseases (NIAID). In each dosing cohort, ten people received active vaccine, and three received a saline placebo. Serum samples from each individual were collected before vaccination (day 0), after the first vaccination (day 28), after the second vaccination (days 42 and 56) and on days 84 and 180. To analyze the epitope repertoire of serum samples from participants who received the rVSVΔG-ZEBOV-GP vaccine, we generated a GFPDL containing 50- to 1,000-bp fragments of the GP gene from the EBOV Mayinga strain (FIG. 9) or the homologous Kikwit strain (FIGS. 10A and 10B), with >107 unique phage clones. These were expected to display all possible linear and conformational epitopes. The GP sequence of Mayinga of 1976 differs from the Kikwit strain of 1995 used in the vaccine by only nine amino acids, whereas the Makona strain of 2014 differs from Mayinga by 20 amino acids (FIGS. 10A and 10B).

Figure 11:
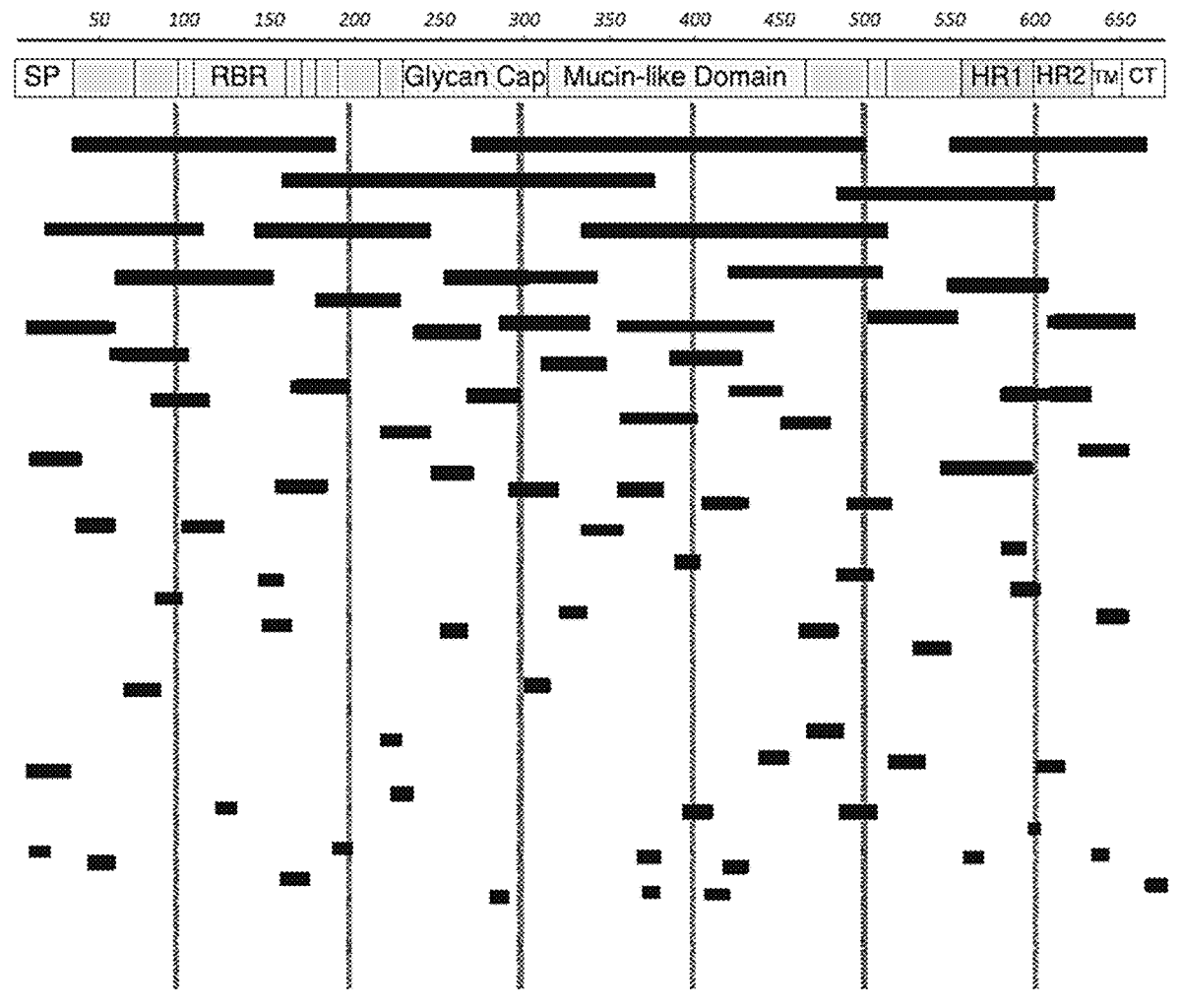
Figure 12:
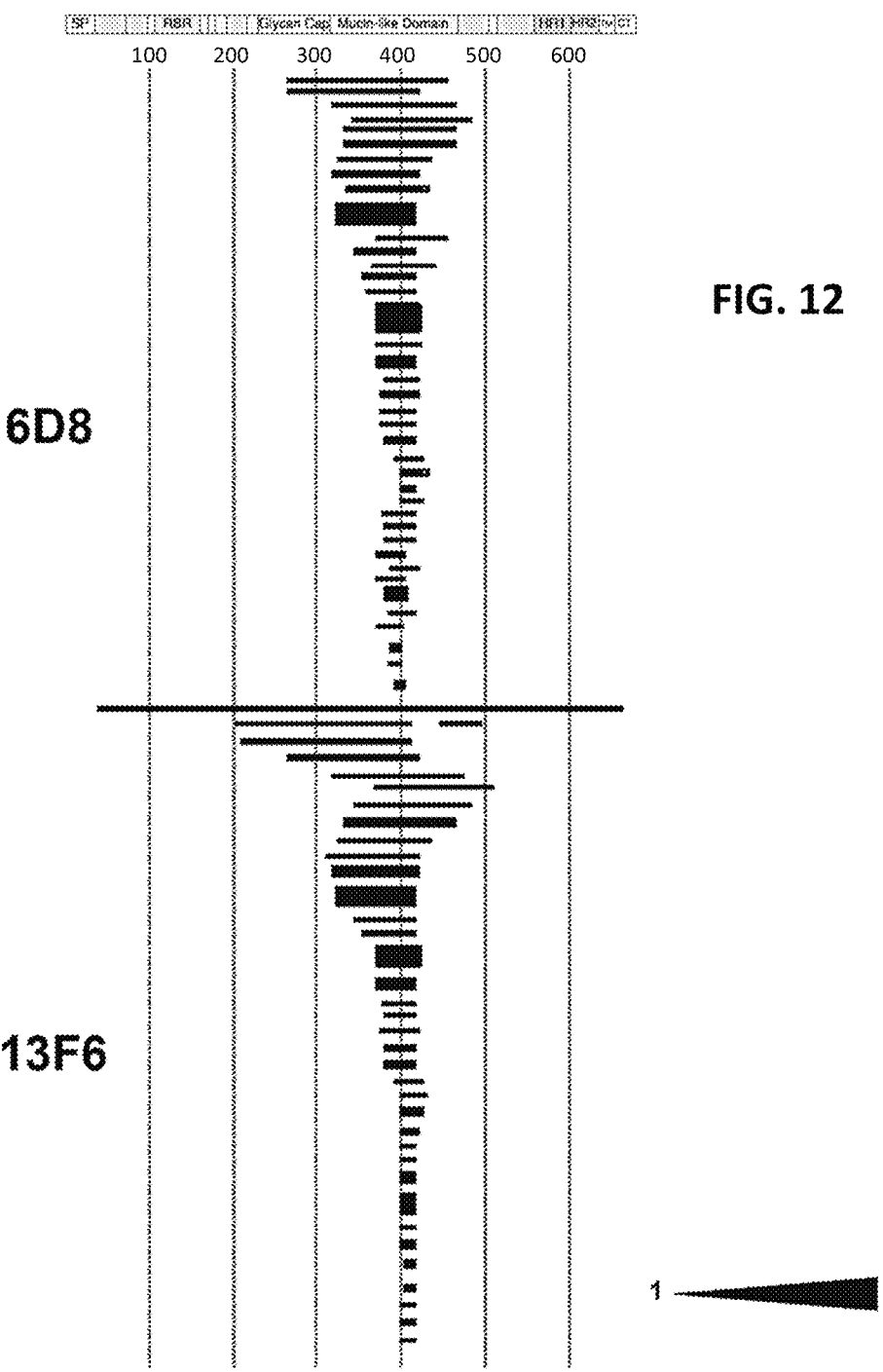
FIG. 12. GFPDL based epitope mapping of protective MAbs 6D8 and 13F6 used in the MB-003 cocktail. Graphical distribution of representative clones with a frequency of >2, obtained after affinity selection, are shown. The common conserved minimal sequence (residues of SEQ ID NO: 35, residue numbering is shown in the figure) for each Mab identified using GFPDL mapping is shown in the table compared to the sequence previously identified 'known site' (Davidson, E. et al. *J. Virol.* 89, 10982-10992, 2015). The reactivity of the GFPDL identified sequence to the respective MAb was confirmed by phage ELISA.
Figure 13A:
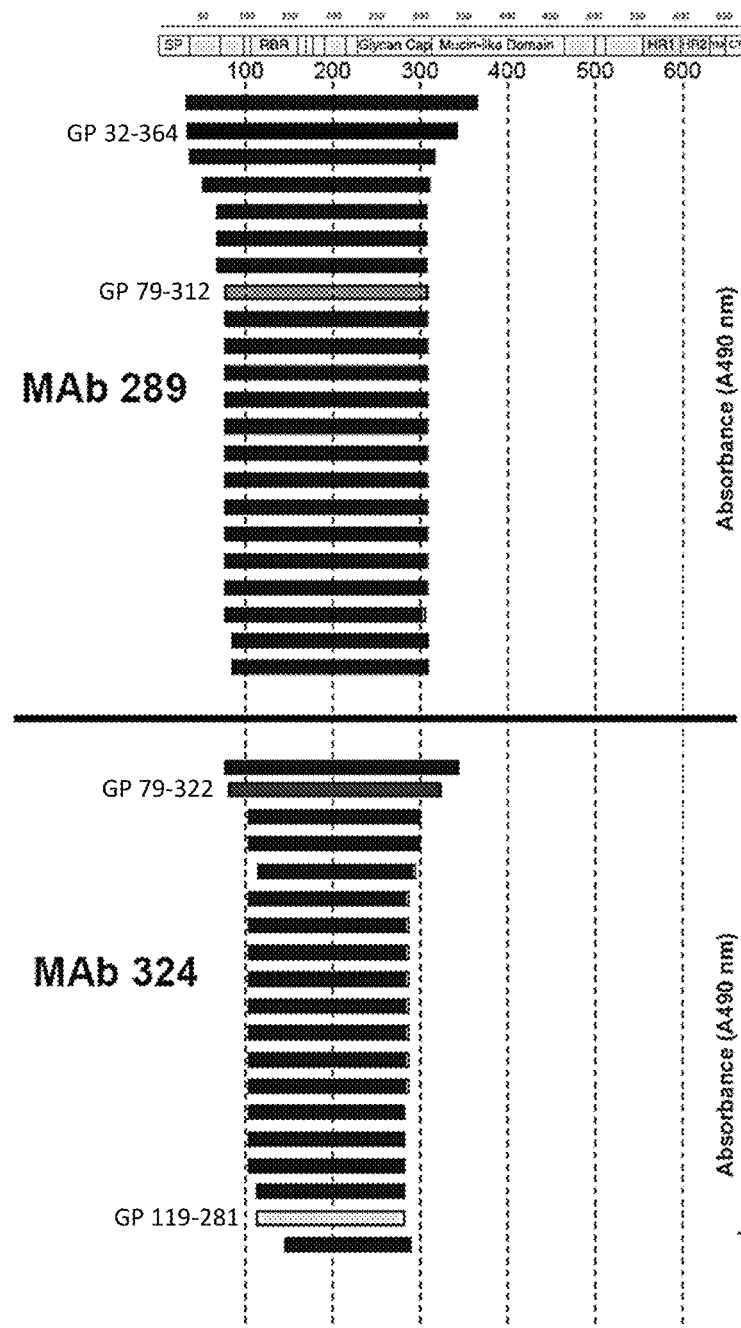
FIGS. 13A-13C. GFPDL based epitope mapping of cross-reactive conformation dependent neutralizing and protective human MAb 289 and MAb 324 from EBOV survivors (Flyak, A. I. et al. *Cell* 164, 392-405, 2016). The reactivity of the GFPDL identified sequence to the respective MAb was confirmed by phage ELISA shown in FIGS. 13B and 13C using the indicated phage clones.
Figure 13B:
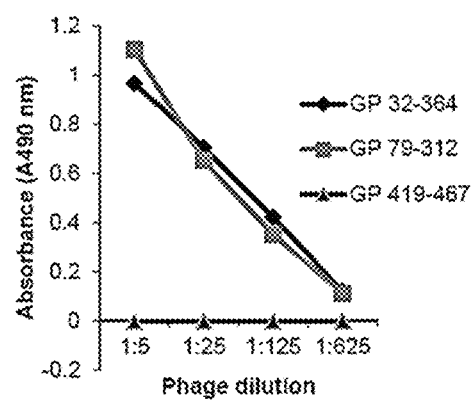
Figure 13C:
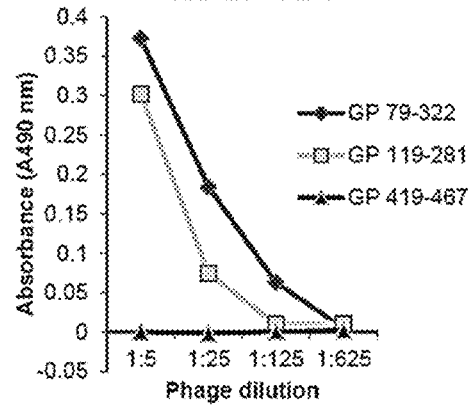

Sequencing of the EBOV GFPDL confirmed a random distribution of size and sequence of inserts that spanned the entire GP (FIG. 11). To ascertain that the antibody repertoire identified using the GFPDL approach represented both linear and conformational epitopes, we performed two independent experiments. First, a panel of EBOV-protective monoclonal antibodies (MAbs) was used to identify and confirm the potential of the EBOV GFPDL to map both linear and conformational antibody epitopes. This panel included 6D8 and 13F6, which are components of the MB-003 cocktail for treatment of EBOV infection (FIG. 12), and conformation-dependent cross-reactive neutralizing and protective human MAbs derived from EBOV survivors (Flyak, A. I. et al. *Cell* 164, 392-405, 2016) (FIGS. 13A13C). The consensus epitope sequences obtained through GFPDL analysis were similar to the footprints previously identified for the MB-003 MAbs (Davidson, E. et al. *J. Virol.* 89, 10982-10992, 2015; Murin, C. D. et al. *PNAS* 111, 17182-17187, 2014) or for MAbs from survivors (Flyak, A. I. et al. *Cell* 164, 392-405, 2016), providing proof of concept that the GFPDL approach can identify linear and conformation-specific antibodies in polyclonal serum after EBOV infection or vaccination.

Figure 14:
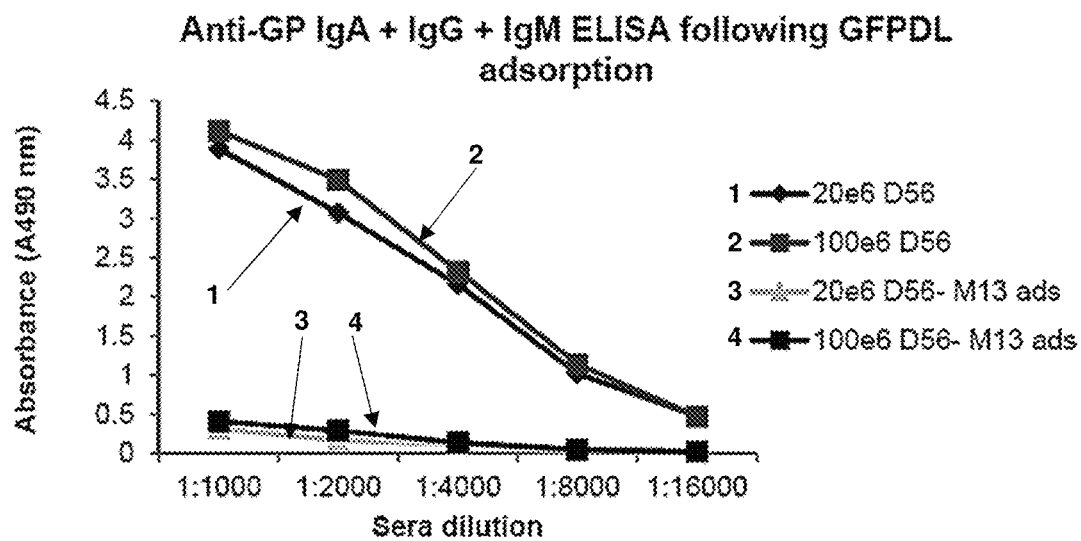
FIG. 14. Anti-GP reactivity of post-second vaccination sera for 20 million and 100 million pfu vaccine dose in ELISA before and after EBOVGFPDL adsorption. Post second vaccination sera from individuals vaccinated with 20 million and 100 million rVSVΔG-ZEBOV-GP vaccine dose was adsorbed on EBOV GFPDL coated petri dishes. Binding to recombinant EBOV-GP is shown before and after GFPDL-adsorption (the after condition is indicated by "M13 ads") in ELISA using HRP conjugated goat anti-human IgA$^+$IgG$^+$IgM specific antibody.

Second, we determined the capacity of the EBOV GFPDL to adsorb EBOV GP-specific antibodies in post-vaccination polyclonal human sera. After two rounds of adsorption with the EBOV GFPDL, 85-92% of GP-specific antibodies in post-vaccination human sera were adsorbed by GP phage display libraries, as determined by binding to EBOV GP in ELISA (FIG. 14). Together, the epitope mapping of MAbs and adsorption studies in post-vaccination polyclonal sera provided support for using the EBOV GP GFPDL to dissect the polyclonal antibody repertoires in human sera.

To study antibody responses after rVSVΔG-ZEBOV-GP vaccination, we collected serum specimens from individuals vaccinated with 3 million, 20 million or 100 million PFU vaccine or placebo control before vaccination (day 0), 28 d (day 28) after the primary vaccination and 28 d after booster vaccination (day 56). The sera of all participants in each dose group were pooled and used for mapping of overall antibody epitope repertoires by EBOV GFPDL (FIG. 1).

Prevaccination sera and the placebo controls were bound by very few phages. In the rVSVΔG-ZEBOV-GP-vaccinated groups, 4 weeks after the first vaccination, the number of bound phages was higher in sera from the 20-million-PFU dose ($2.12 \times 10^6$) group than in sera from the 3-million-PFU and 100-million-PFU groups ($1.12 \times 10^6$ and $1.45 \times 10^6$ phages, respectively) (FIG. 1a). Sequencing of GP fragments expressed by phages bound with sera after the first vaccination showed a high frequency of bound phages displaying both small and large fragments mapping across the N-terminal GP1 head domain and, to a lesser degree, the C-terminal GP2 stalk domain of the EBOV GP protein (FIG. 1b). Sera from the 3-million-PFU and 20-million-PFU cohorts contained antibodies that mapped to the glycan cap and mucin domain and that recognized an epitope in the transmembrane region of the GP2 protein that was not captured by sera from the 100-million-PFU dose cohort. Sera from the 20-million-PFU dosing cohort additionally recognized several small and large immunodominant epitopes in the N-terminal half of EBOV GP mapping to the receptor-binding region (RBR) and between the RBR and the glycan cap domain (FIG. 1b).

Unexpectedly, after the second vaccination, the number of EBOV GFPDL bound phages decreased 2-10 times relatively to the first vaccination (FIG. 1a). The antibody epitope profiles did not substantially change, apart from an apparent reduction in antibodies mapping to the GP2 transmembrane region in the 3-million- and 20-million-PFU dose recipients, an increase in antibodies specific to the glycan cap in the 20-million-PFU cohort, and a small reduction in antibodies recognizing large sequences in the mucin-like domain from the 100-million-PFU group (FIG. 1c).

Antigenic Sites Within EBOV GP

Figure 2B:
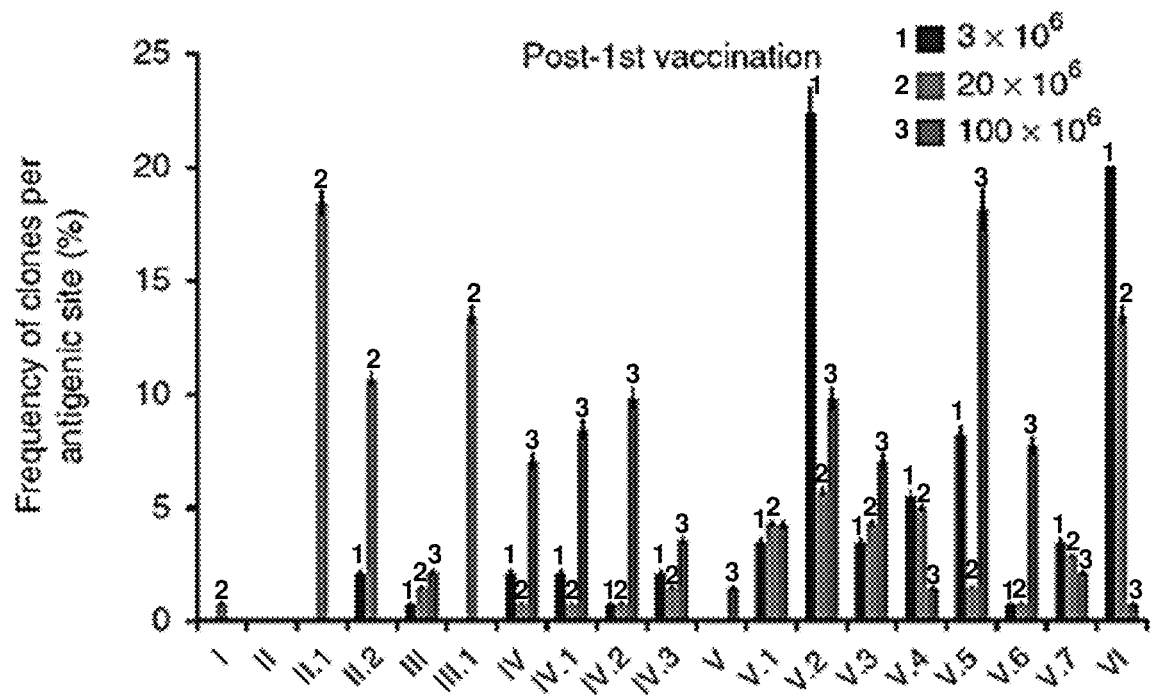
Figure 2C:
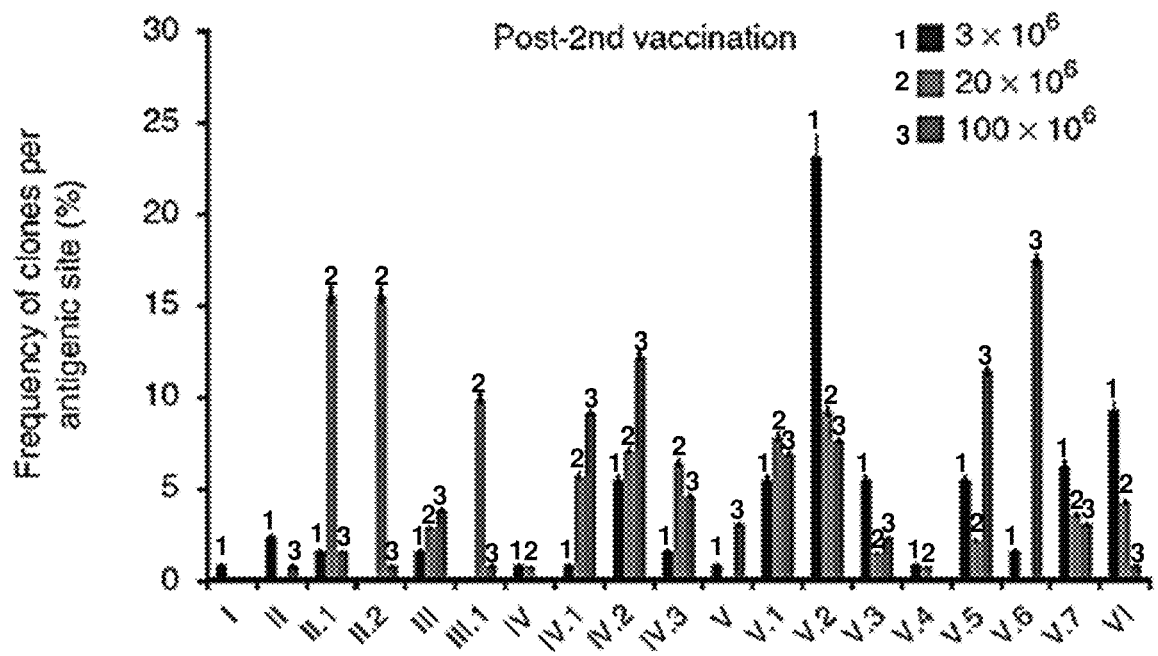
Figure 3A:
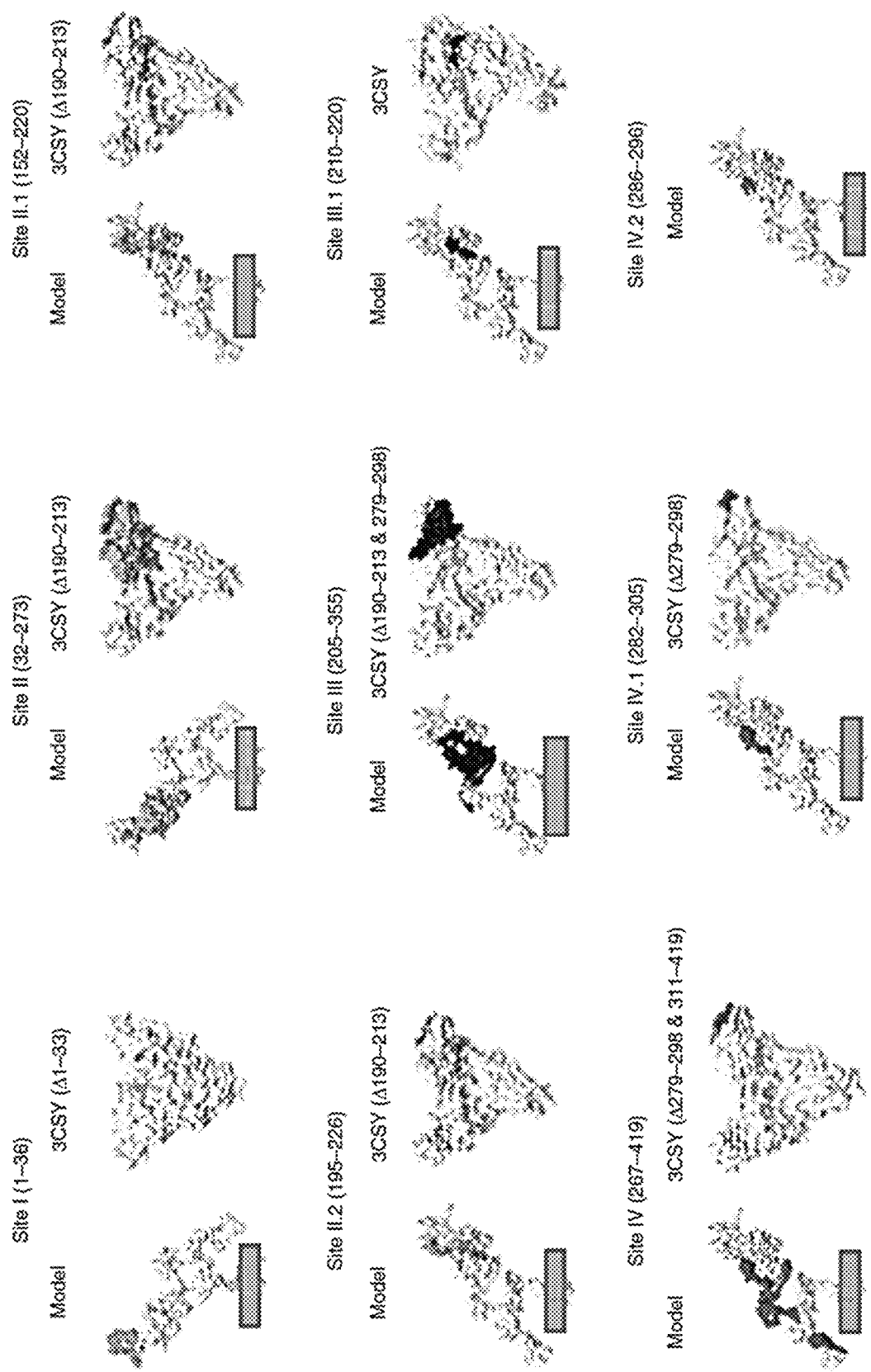
FIG. 3A-3B. Structural representation of antigenic sites in EBOV GP identified with GFPDL. Representations of individual antigenic sites on the surface structures of a complete EBOV GP model (left) and solved EBOV GP structure (PDB 3CSY) (Lee, J. E. et al. *Nature* 454, 177-182, 2008) are shown (right) where available; antigenic sites in a monomer (chain A) are color coded as in FIG. 2. The EBOV GP structure used for crystallography encompasses amino acid residues 33-189, 214-278, 299-310 and 502-599 of the mature 676-aa GP sequence. The transmembrane (TM) domain is shown in orange, and the viral membrane is shown (gray bar) on the model images. Sites I, II and VI on the model are shown in front view. Sites II.1, II.2, III, III.1, IV, IV.1, IV.2, IV.3, V and V.1-V.7 are shown in rear view. All sites (except site I) are depicted in front view on the solved structure.
Figure 3B:
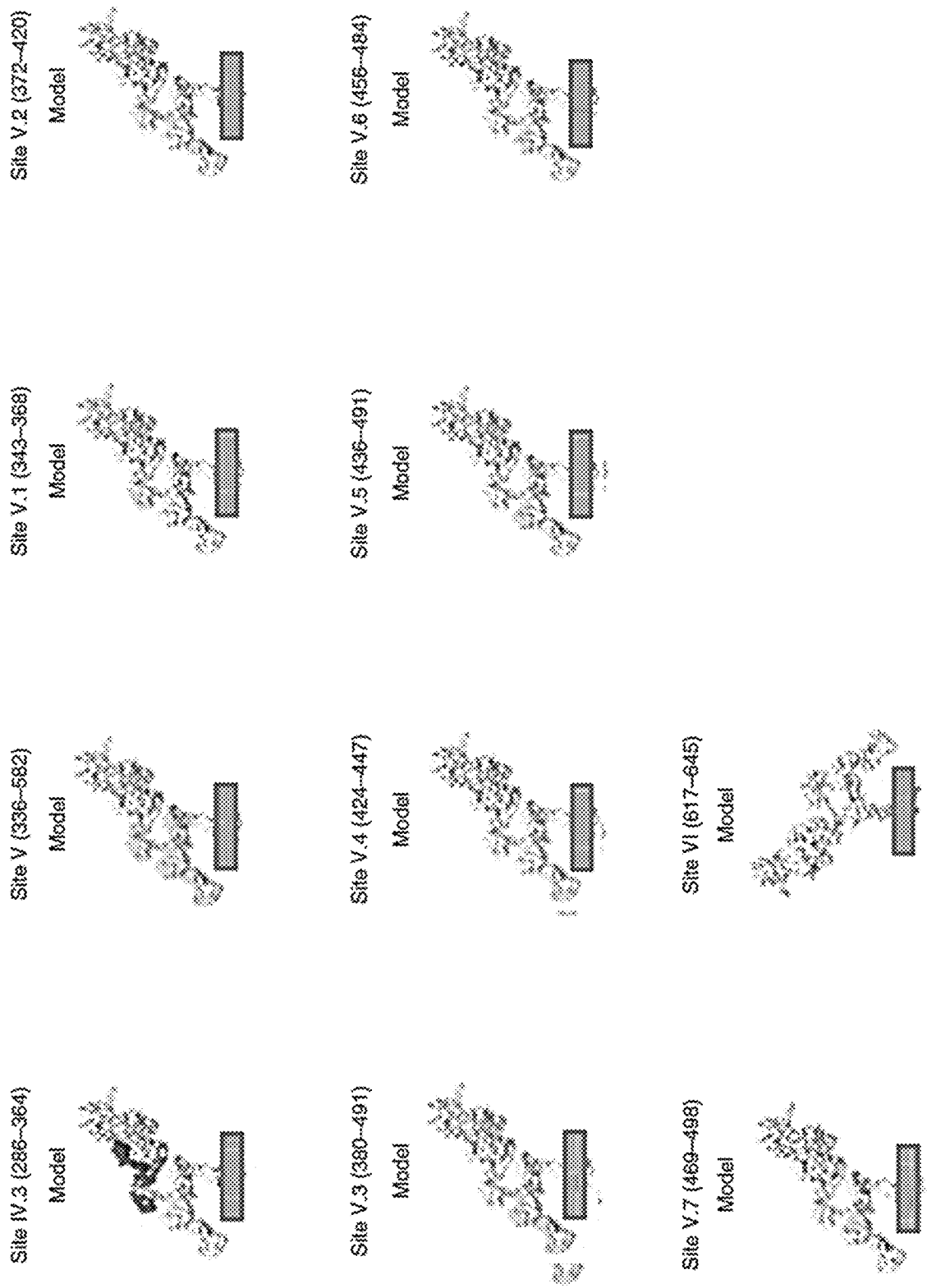
Figure 15:
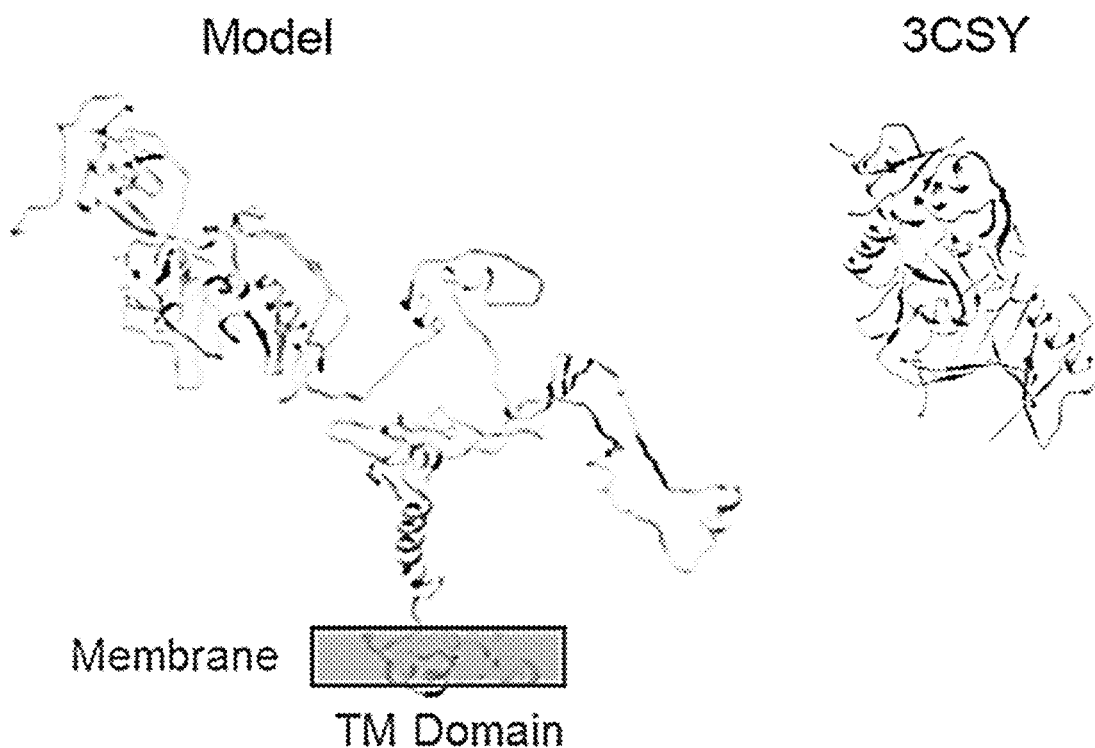
FIG. 15. Model of the complete Zaire Ebola GP monomer generated using I-TASSER (left) showing transmembrane (TM) domain and membrane, and solved crystal GP structure (PDB Id #3CSY; includes GP residues 33-189, 214-278, 299-310 and 502-599) in monomeric form on right.

EBOV-neutralizing and/or protective MAbs, such as KZ52 and the MAb cocktails ZMAb, ZMapp and MB-003, have been shown to recognize epitopes within or flanking the mucin-like domain, glycan cap or base of GP (Davidson, E. et al. *J. Virol.* 89, 10982-10992, 2015; Murin, C. D. et al. *PNAS* 111, 17182-17187, 2014) (FIG. 2a). Vaccination with rVSVΔG-ZEBOV-GP generated an immune response to 19 unique antigenic sites defined by six large antigenic regions (herein referred to as GP-I through GP-VI) and 13 smaller antigenic sites (GP-II.1 through GP-V.7) contained within EBOV GP (FIG. 2a and FIGS. 6A and 6B). These antigenic regions and sites include several novel linear and conformational epitopes, including GP-II, GP-II.1, GP-II.2, GP-IV.1, GP-IV.3, GP-V.1, GP-V.4, GP-V.5, GP-V.6, GP-V.7 and an immunodominant sequence (GP-VI) in the transmembrane or cytoplasmic tail. The frequency of phages expressing these GP antigenic sites selected by sera after the first (FIG. 2b) and second (FIG. 2c) vaccinations for the three rVSVΔG-ZEBOV-GP dose groups are shown in FIGS. 6A and 6B. Antibodies in post-vaccination sera from the 20-million-PFU dose group showed the highest epitope diversity, as assessed by selecting phage clones from most of the antigenic sites within GP, whereas the sera from the lower (3 million PFU) and higher (100 million PFU) dose groups contained antibodies that predominantly mapped to the C-terminal half of the EBOV GP. The surface exposure of each of these antigenic sites on the EBOV GP crystal structure (Lee, J. E. et al. *Nature* 454, 177-182, 2008) (PDB 3CSY; includes GP residues 33-189, 214-278, 299-310 and 502-599) and the model of complete EBOV GP monomer (Yang, J. et al. *Nat. Methods* 12, 7-8, 2015) (FIG. 15) are shown in FIG. 3. The surface representation showed that most of the key antibody targets of rVSVΔG-ZEBOV-GP, including several of the GP epitopes (GP-II, GP-II.1, GP-II.2, GP-IV.1, GP-IV.3, GP-V.1, GP-V.4, GP-V.5, GP-V.6, GP-V.7) discovered in this study, are exposed on the native ZEBOV GP structures. Analysis of sequence homology of GP showed that some sites, including GP-II, GP-II.1, GP- IV.1, GP-IV.2 and GP-VI, are >70% conserved between diverse EBOV strains, such as Sudan, Bundibugyo, and Kikwit (FIG. 7). These data suggest that antibodies induced after rVSVΔG-ZEBOV-GP vaccination against some conserved antigenic sites may cross-react with diverse EBOV strains, even though cross-protection has not been observed in rVSVΔG-ZEBOVGP-vaccinated NHPs challenged with EBOV Sudan virus29.

Correlation of GP Antibody Binding with EBOV Neutralization

Because the GFPDL analyses were carried out on the pooled serum samples from each group, we performed quantitative and qualitative analyses of individual pre- and post-vaccination sera with recombinant glycosylated GP produced in a mammalian system using an SPR-based real-time kinetics assay.

Figure 4C:
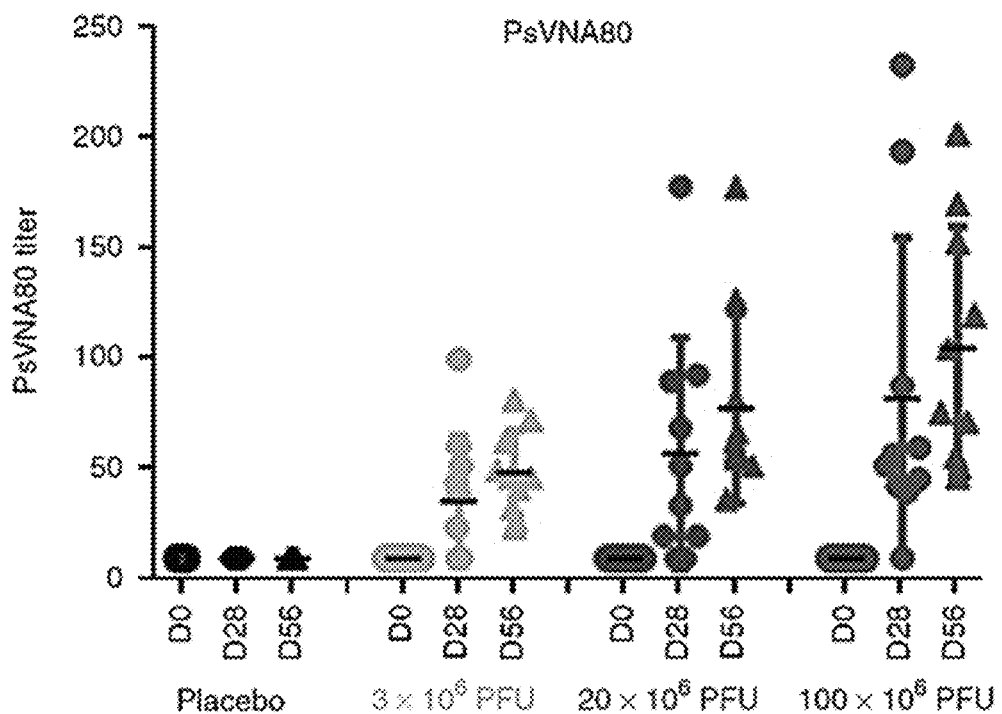
Figure 4D:
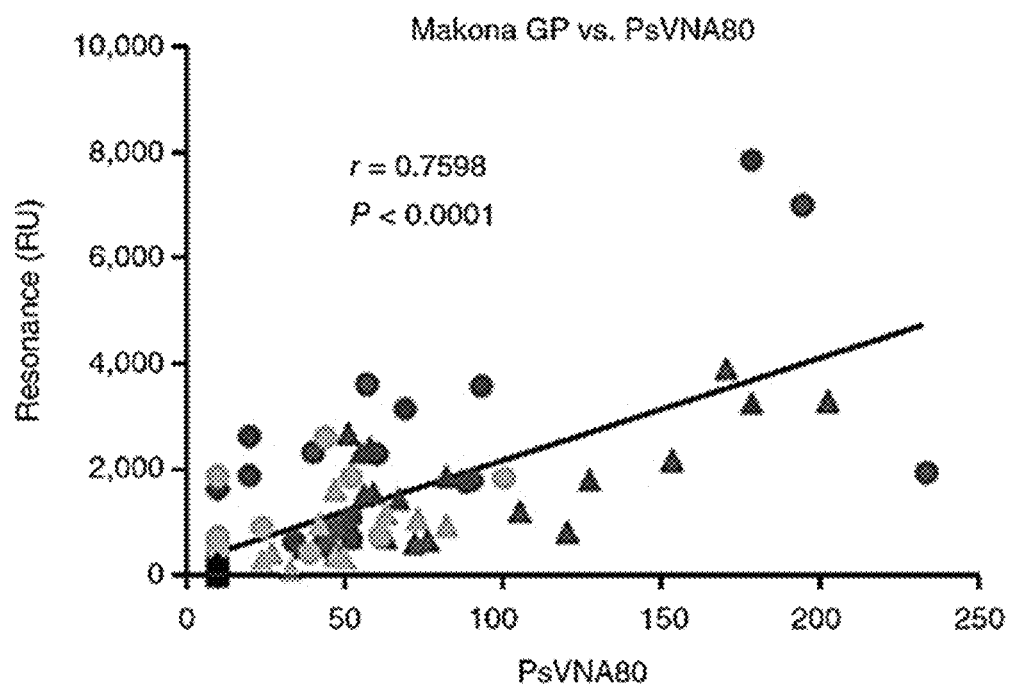
Figure 4E:
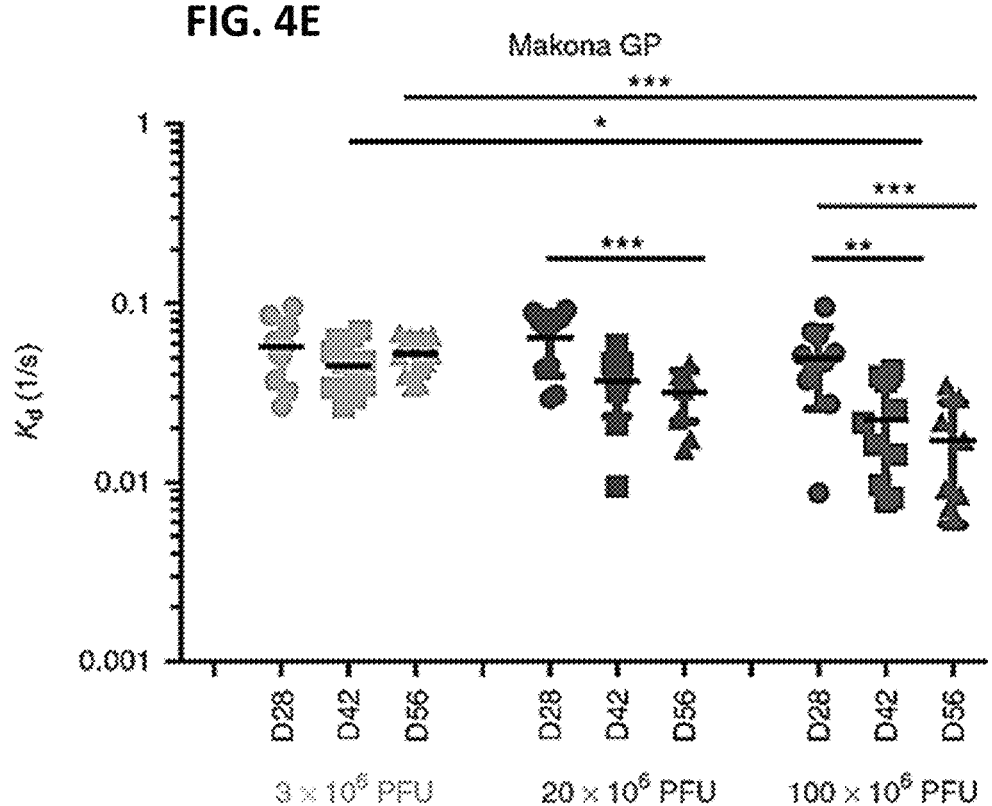

Binding kinetics of individual serum samples from the three vaccine-dose cohorts at early post-vaccination time points (28 d after first vaccination and 14 and 28 d after second vaccination) and at later time points (day 84 and day 180) was performed using the GP from Mayinga and Makona strains (FIG. 4a,b). Antibody binding titers of individual serum samples (N=10 for each vaccine group at each time point) against GP were measured as resonance units (RU) in SPR (FIG. 4). Control sera from placebo did not show significant antibody binding to GP before or after mock vaccination. After the first rVSVΔG-ZEBOV-GP vaccination (day 28), all samples reacted strongly with GP from Mayinga (FIG. 4a) and Makona strains (FIG. 4b), with sera from the 20-million- and 100-million-PFU groups showing higher binding (mean RU=2,152 and 2,056, respectively) than those of the 3-million-PFU group (mean RU=1,197), but the difference among groups did not reach statistical significance. However, the mean serum antibody reactivity decreased marginally (mean RU=800 for 3 million PFU; 1,608 for 20 million PFU; 1,715 for 100 million PFU) for all the vaccine dose groups by day 42 (14 d after the second vaccination) and even further by day 56 (28 d after administration of the homologous boost; mean RU=679 for 3 million PFU; 1,409 for 20 million PFU; 1,536 for 100 million PFU). By days 84 and 180, serum anti-GP titers had diminished substantially, such that by day 180, 80% of individuals had very weak GP-binding antibody levels for all vaccine groups, though binding-antibody titers were marginally higher for the group that received the highest vaccine dose (mean GP binding RU=133 for 3 million PFU; 260 for 20 million PFU; 490 for 100 million PFU). We observed a strong correlation between in vitro EBOV neutralization titers (FIG. 4c) and the titers of serum GP-binding antibody, as measured by SPR, after rVSVΔG-ZEBOV-GP vaccination (r=0.75; P<0.0001) (FIG. 4d). This analysis revealed that the replicating rVSVΔG-ZEBOV-GP vaccination generated strong GP-binding antibodies that peaked after the first vaccination but were not boosted after the second vaccination and were not long lasting.

Antibody Affinity Maturation after Vaccination

Figure 4F:
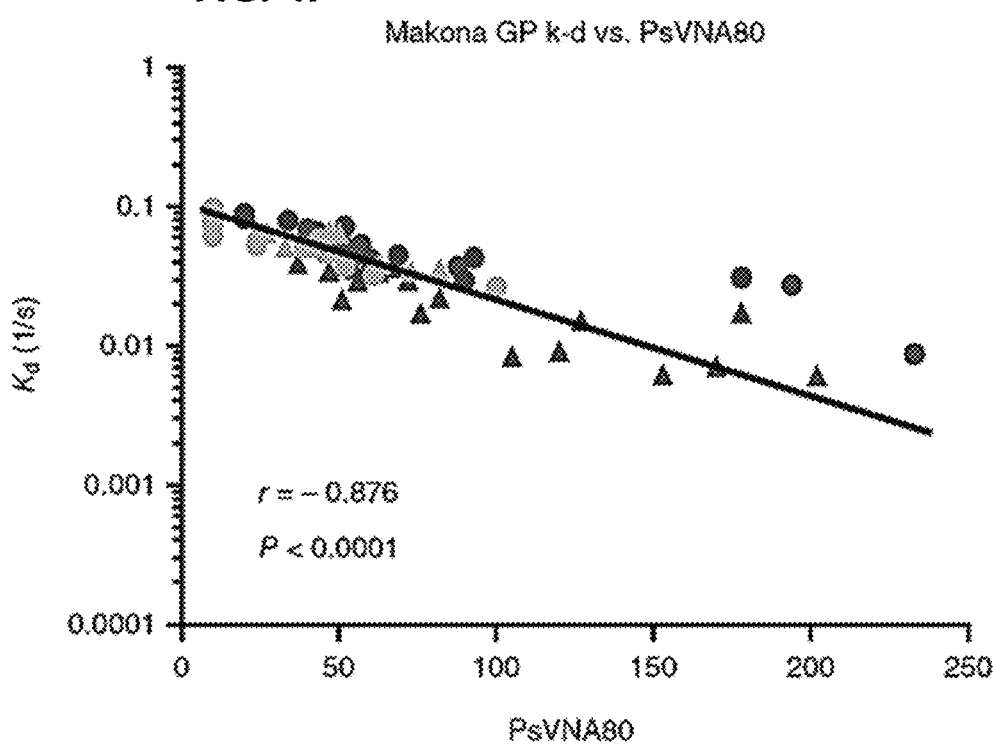

To further investigate whether different rVSVΔG-ZEBOV-GP vaccine doses promote anti-GP affinity maturation, we determined the dissociation rates (Kd) of post-vaccination serum antibody-antigen complexes using SPR. Dissociation rate is independent of antibody concentration and provides a measurement of overall affinity of polyclonal antibody binding, as previously described (Khurana, S. et al. Sci. Transl. Med. 3, 85ra48, 2011). The off-rates for polyclonal serum antibodies bound to GP were lower (indicating stronger affinity) at 14 d and 28 d after the second vaccination than at 28 d after the first vaccination, but this difference reached statistical significance only for the 20-million-PFU and 100-million-PFU groups (FIG. 4c). However, polyclonal antibody off-rates (Kd=$10^{-2}$-$10^{-3}$/s) were low, even after two vaccinations, compared to some other human viral vaccines (Khurana, S. et al. Sci. Transl. Med. 3, 85ra48, 2011). GP-specific antibody off-rates after the first (day 28) and second vaccination (day 56) correlated strongly with virus neutralization titers (r=−0.876, P=<0.0001), emphasizing the potential importance of antibody affinity maturation for antiviral activity (FIG. 4f). These observations suggest that the higher rVSVΔG-ZEBOV-GP vaccine doses (20 million PFU and 100 million PFU) promote better antibody affinity maturation to GP than the lower vaccine dose.

Anti-GP Isotype and EBOV-Neutralizing Capacity

Figure 17:
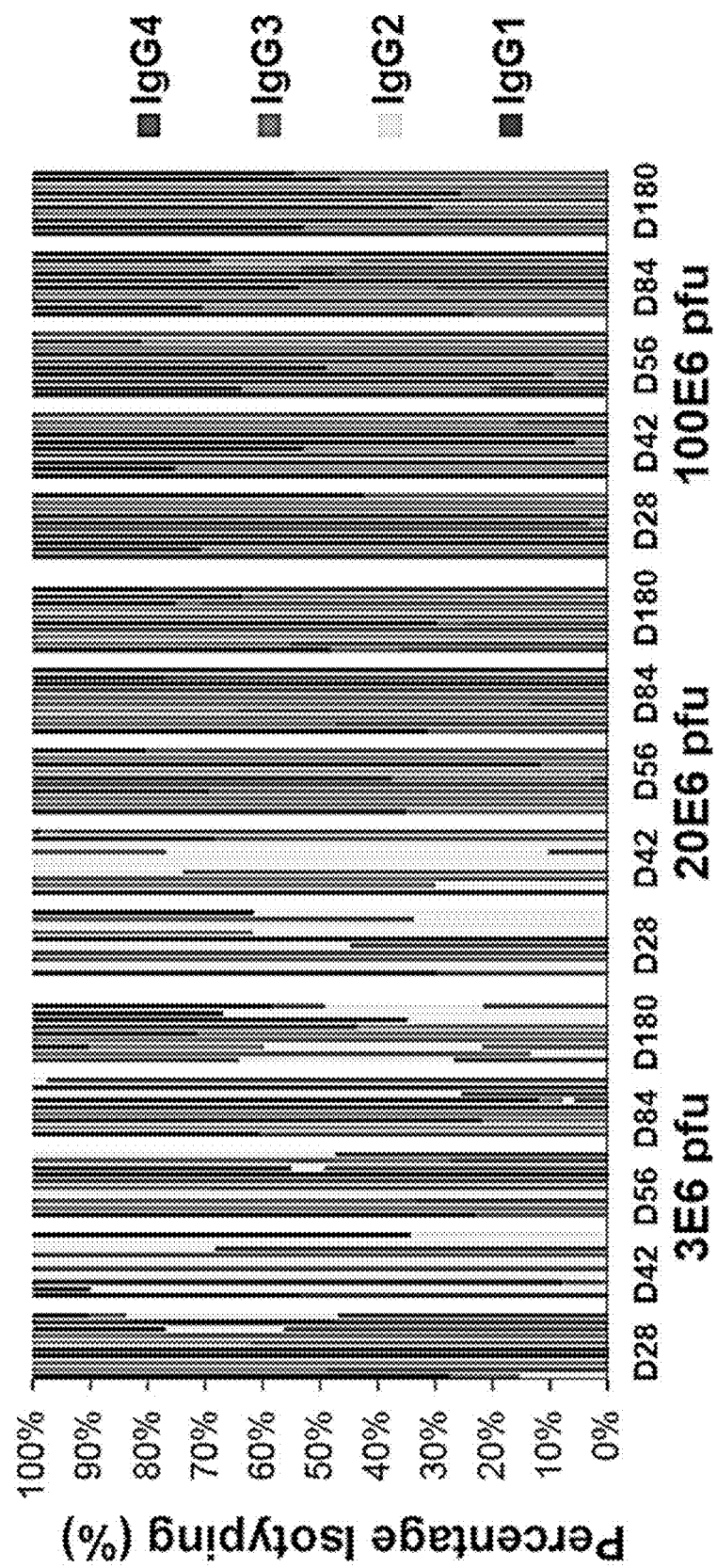
FIG. 17. IgG subclass of human serum binding to EBOV-GP following rVSVΔG-ZEBOV-GP vaccination. The subclass of total IgG of serum antibodies bound to EBOV-GP are shown for serum samples collected at different time points from adults vaccinated with three different rVSVΔG-ZEBOV-GP vaccine dose administered groups as measured in SPR experiment. The resonance unit for each anti-GP antibody IgG subclass was divided by the total resonance units for total bound IgG antibodies combined for each sera and represented as a percentage.

Isotype analysis of the GP-binding antibodies demonstrated representation of all isotypes (IgA, IgG and IgM) and IgG subclasses in postvaccination sera (FIG. 5a). We were surprised to find that most of the GP-binding antibodies both after primary and after booster vaccinations, were of IgM isotype in all vaccine-dose groups (FIG. 5a). The second most abundant GP-binding antibodies were of IgA isotype, and their frequency in serum increased with dosage (mean IgA=4% for 3 million PFU; 10% for 20 million PFU; 20% for 100 million PFU) at day 56. The anti-GP isotype reactivity was also analyzed by ELISA (FIGS. 16A-16C). Antibody isotyping of GP-binding antibodies in post-vaccination sera by ELISA showed concordance with the isotypes determined by SPR, but ELISA underestimated the proportion of GP-binding IgM antibodies compared to SPR. In contrast, at later time points (day 84 and day 180) after vaccination, the GP-binding antibodies remaining in the sera (FIG. 4a) were of IgA or IgG subclasses (FIG. 5a), suggesting that most of the anti-GP antibody response generated early after vaccination is of the IgM isotype, which does not provide a long-lasting systemic anti-GP antibody response. After vaccination, of the total GP-bound IgG antibodies, IgG1, IgG2 and IgG3 contributed most to GP binding in the 3-million-PFU and 20-million-PFU vaccine cohort, whereas for the 100-million-PFU dose a significant amount of anti-GP antibodies were of IgG3 and IgG4 subclasses (FIG. 17).

Figures 5D, 5E, 5F:
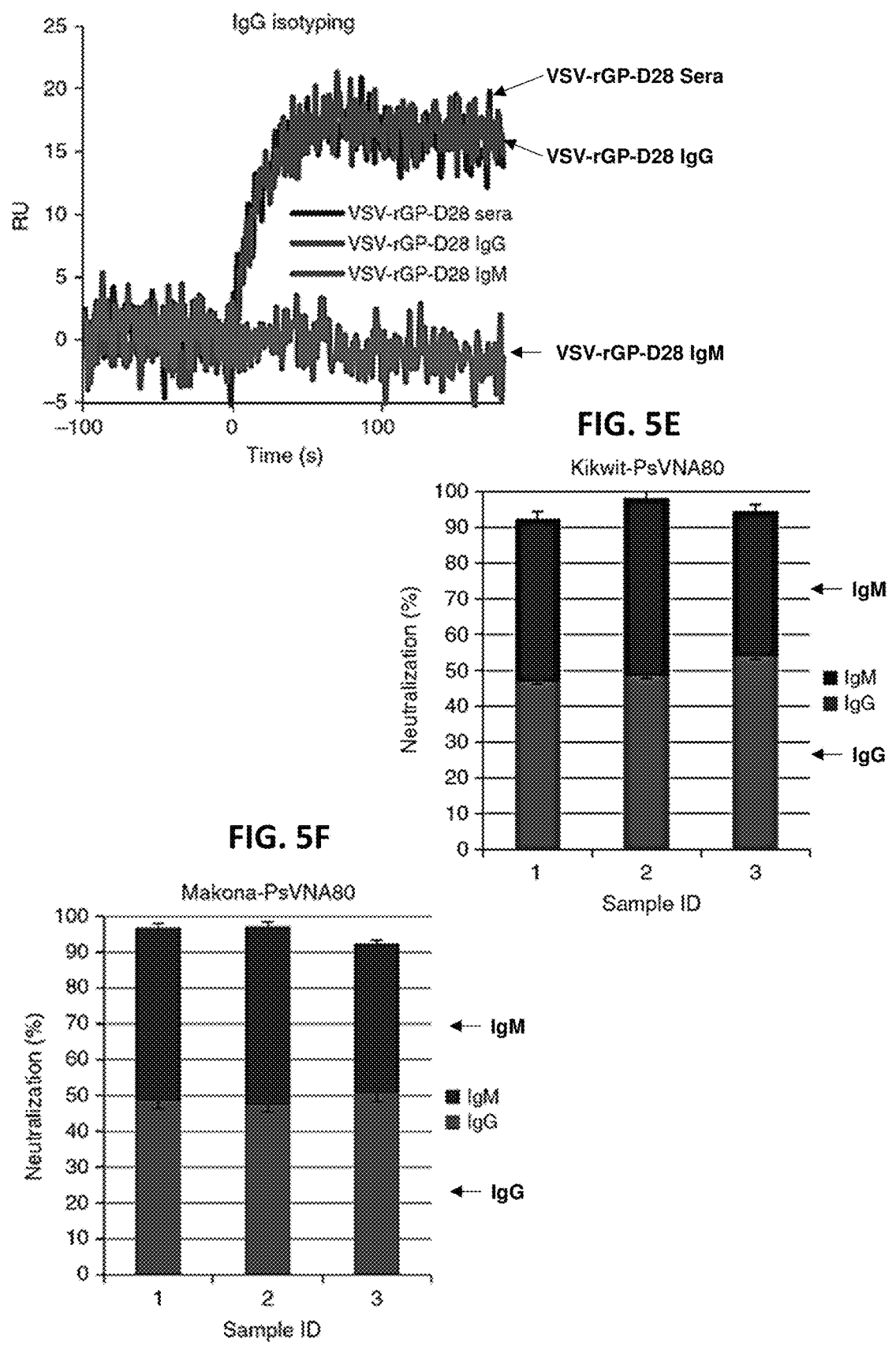

To understand the functional role of IgM antibodies in the postvaccination response, we evaluated their contribution to virus neutralization and compared them to IgG antibodies in post-vaccination sera. We used anti-human IgG and anti-human IgM affinity chromatography columns to purify IgG and IgM antibodies from three sera samples, taken after the second vaccination, that showed similar amounts of GP-binding IgG and IgM antibodies and evaluated binding to the GP in SPR (FIG. 5b), isotype specificity (FIG. 5c,d) and virus neutralization of Kikwit and Makona EBOV strains (FIG. 5e,f). The IgG/IgM ratio determined from affinity chromatography in post-vaccination sera was in good agreement with that determined by SPR. The purified IgG and IgM antibodies from all sera reacted with GP, and, as expected, the IgG antibodies showed higher affinity (slower dissociation) to GP than IgM in SPR (FIG. 5b). The purity of antibody isotypes was confirmed by human IgG- and human IgM-specific secondary antibodies using SPR (FIG. 5c,d). The purified post-vaccination IgM antibodies at serum concentration levels contributed 40-50% to virus neutralization, and these results were similar to those with IgG antibodies purified from post-vaccination sera from the same individuals (FIGS. 5E and 5F). These results suggest that anti-GP IgM antibodies could have an important role in protection against EBOV disease in vivo.

The results of our study demonstrate independent evolution of antibody binding patterns to EBOV GP—in terms of epitope repertoire diversity, affinity maturation and isotype switching—in the three vaccine-dose groups after the first and second vaccinations and show an important contribution of anti-GP IgM antibodies to EBOV neutralization.

Discussion

In-depth understanding of the humoral immune response to Ebola vaccines under advanced development is required to identify meaningful correlates of protection in humans and animal models to facilitate evaluation of effective vaccine candidates. The epitope-binding patterns in the GP antigenic sites were most diverse in the 20-million-PFU dose samples. This effect, in which a more diverse antibody repertoire is generated from a lower vaccine dose, has been observed in multiple human influenza vaccination studies and was linked with optimal CD4+ T cell help, which may affect the B cell and T cell response differently after vaccination (Chung, K. Y. et al. *Vaccine* 33, 3953-3962, 2015; Nicholson, K. G. et al. *Lancet* 357, 1937-1943, 2001; Jackson, L. A. et al. *J. Am. Med. Assoc.* 314, 237-246, 2015; and Mulligan, M. J. et al. *J. Am. Med. Assoc.* 312, 1409-1419, 2014). The lower numbers of captured GFPDL phages after the second vaccination, as compared to the first vaccination, suggest that pre-existing antibodies against rVSVΔG-ZEBOV-GP after the first vaccination may have impeded replication of the rVSV vector and possibly masked some GP epitopes. Notably, the 20-million-PFU dose, selected for the phase ⅔ clinical trials in Western Africa on the basis of safety and in vitro neutralization data, generated the broadest antibody repertoire after vaccination.

After finding that a substantial proportion of anti-GP antibodies were of IgM and IgA isotypes, we performed GFPDL analysis to determine specific epitopes recognized by IgA, IgG and IgM antibodies in post-vaccination sera. In the sera pooled from each group after the first vaccination, the number of bound phages was approximately twofold higher in IgM-bound antibodies than in protein A/G-bound (primarily IgG) antibodies, and in IgA-bound antibodies was about tenfold lower for all vaccine groups (FIG. 8). We performed an additional analysis of sera from individuals in the 20-million-PFU and 100-million-PFU groups using IgA-, IgG- and IgM-specific capture beads to further define the fine epitope specificity of these antibodies after the first vaccination using homologous Kikwit GP EBOV strain GFPDL (FIGS. 18A-18C). The epitope repertoires of IgG-specific antibodies in individual post-vaccination sera were similar to those identified in IgG antibodies from pooled post-vaccination sera from the 20-million-PFU and 100-million-PFU dose groups (FIG. 1). However, the IgM antibody epitope repertoire in the 100-million-PFU dose group was more diverse than that of the 20-million-PFU group, which predominantly recognized the mucin-like domain. The individual IgM GFPDL responses quantitatively tracked the SPR data for total GP-binding antibodies, which measures binding of all anti-GP antibody isotypes. In both dose groups (20 million and 100 million PFU), IgA-specific polyclonal repertoire was more focused on the glycan cap and mucinlike domain, but sera from the 20-million-PFU group recognized the antigenic site V.7 at the C terminus of GP1 with higher frequency (FIGS. 18A-18C). One possible limitation of GFPDL-based assessment is that it is unlikely to detect paratopic interactions that require post-translational modification or rare quaternary epitopes that cross GP protomers. However, 85-92% of anti-GP antibodies from post-vaccination sera were removed by adsorption with the EBOV GP GFPDL, supporting the use of the EBOV GP GFPDL for analyses of human sera, as has been observed with other viral antigens, including different influenza strains, respiratory syncytial virus (RSV) protein F (RSV-F) and heavily glycosylated RSV-G. Moreover, binding to properly folded glycosylated Ebola GP in SPR can overcome these limitations and provide additional insight into the post-vaccination anti-GP polyclonal antibody response. Real-time antibody kinetics of individual post-vaccination sera by SPR revealed several unexpected findings, including lack of impact of the second vaccination on anti-GP responses, a fast decay of anti-GP titers within 2 months after the second vaccination, limited antibody class switching and modest antibody affinity maturation.

The observation of low antibody class switching after rVSVΔGZEBOV-GP vaccination is notable. Our findings suggest that IgM antibodies are the predominant isotype and decayed rapidly after the first and second vaccination. Although IgM antibodies are of low affinity, their multivalency compensates for overall binding avidity and helps in virus neutralization. Therefore, IgM antibodies may contribute to protection against infection, which would explain the relatively rapid protection that has been described in NHP studies and the rVSVΔGZEBOV-GP ring vaccination study in Africa. The amount of IgA in most post-vaccination sera samples was too low to purify and perform a reproducible EBOV neutralization assay. IgA purified from sera from two vaccine recipients showed that GP-specific IgA antibodies can neutralize virus in vitro but to a lesser extent than IgM antibodies.

Most ELISAs used for evaluation of Ebola vaccines measure predominantly anti-GP IgG antibody titers, because they rely on anti-human IgG secondary antibodies. Such ELISA titers alone may underestimate the full spectrum of the vaccine-induced immune response. Although incorporating an anti-human IgM secondary antibody in the ELISA may help mitigate this deficiency, the washing steps involved in the ELISA process, which are important to reduce nonspecific binding, may elute most of the low-affinity IgM antibodies. In addition, anti-GP IgA antibodies may contribute to protection against EBOV infection and disease in vivo, especially at mucosal surfaces. In contrast, the SPR approach captures all antibody classes, including IgM, IgA and IgG, and is also more appropriate for maintaining the native structure of EBOV GP and preserving conformational epitopes.

Class switching and antibody affinity maturation require continuous signals from T cells in the form of cytokines and comigration of antigen specific follicular helper T cells and B cells into germinal centers in lymph nodes. The influence of pre-existing rVSVΔG-ZEBOV-GP-specific antibodies or anti-VSV vector responses at the time of the booster vaccination, with their attenuating effects on rVSV replication and masking of GP epitopes, could adversely affect the formation of germinal centers and prevent antibody class switching, affinity maturation and durable response, as observed in previous vaccine studies. A second vaccination or prime-boost with alternative vaccine platforms (including different VSV serotype vectors) could provide a meaningful increase in affinity maturation and a better immune response, as was observed in prime-boost H5N1 and H7 influenza vaccine studies in humans. In these studies, it was observed that a 3-month minimum interval between the first and second vaccine doses was required for optimal neutralizing-antibody response and antibody affinity maturation.

In summary, we have demonstrated independent evolution of antibody immune responses—in terms of antibody epitope repertoire diversity, affinity maturation, durability and isotype switching—after vaccination with a live rVSV vector-based vaccine in three vaccine-dose groups and revealed the importance of a predominantly anti-GP IgM response for EBOV neutralization. These findings could have significant implications for further development and evaluation of Ebola vaccines. Future Ebola vaccine studies should follow the rate of decay of anti-VSV antibodies to identify the time interval needed for a booster vaccination to generate optimal antibody affinity maturation and durable antibody responses. Our observations suggest that it is important to develop appropriate assays that can provide in-depth understanding of post-vaccination and postinfection antibody responses to help guide development and evaluation of effective Ebola countermeasures such as therapeutics and vaccines.

Methods

Sera samples and monoclonal antibodies. Monoclonal antibodies (MAbs) and recombinant EBOV GP used in this study were purchased from IBT Biosciences Inc. Cross-reactive conformation-dependent neutralizing and protective human MAb 289 and MAb 324 from EBOV survivors were obtained from J. Crowe24. Phase 1, double-blind, placebo-controlled, dose-escalation trials with staggered enrollment were designed across three dose levels as outlined in Regules et al. (*N. Engl. J. Med.* 376(4):330-341, 2017, available online Apr. 1, 2015). Briefly, the rVSVΔG-ZEBOV-GP vaccine consisting of the rVSV strain Indiana and the glycoprotein of the EBOV Kikwit 1995 strain replacing the gene encoding the VSV envelope glycoprotein was administered at 3 million, 20 million or 100 million PFU in the form of a 1-mL injection in the deltoid muscle of healthy adult men and women according to protocols approved by the institutional review board at the US National Institutes of Health NIAID site. Written informed consent was obtained from all the volunteers before enrollment. Within each dosing cohort, 10 received active vaccine and 3 received a saline placebo. Serum samples from each individual were collected before vaccination (day 0), after the first vaccination (day 28), after the second vaccination (days 42 and 56), and on day 84 and day 180 (ClinicalTrials.gov number NCT02280408). Samples were anonymous, and permission to test these deidentified samples in different antibody assays was obtained from the US Food and Drug Administration's Research Involving Human Subjects Committee (FDA-RIHSC) under exemption protocol #15-0B; all assays done fell within the permissible usages in the original consent.

PsVN assay. Pseudovirion neutralization assay (PsVNA) against the homologous Zaire-Kikwit strain glycoprotein was performed as described previously (Regules, J. A. et al. *N. Engl. J. Med.* 376(4):330-341, 2017, available online Apr. 1, 2015).

GFPDL construction. cDNAs complementary to the envelope glycoprotein-encoding gene of EBOV Mayinga or Kikwit strain were chemically synthesized and used for cloning. A gIII display-based phage vector, fSK-9-3, where the desired polypeptide can be displayed on the surface of the phage as a gIII-fusion protein, was used. Purified DNA containing Ebola GP was digested with DNase I to obtain gene fragments of 50-1,000 bp and used for GFPDL construction as described previously (Khurana, S. et al. *PLoS Med.* 6, e1000049, 2009; Khurana, S. et al. *Sci. Transl. Med.* 3, 85ra48, 2011). As the phage libraries were constructed from the whole gene, they potentially display all possible known or unknown viral protein segments ranging in size from 15 to 350 amino acids as fusion proteins on the surface of the bacteriophage.

Adsorption of polyclonal human sera on EBOV GFPDL phages and residual reactivity to EBOV GP. Prior to panning of GFPDL, 500 µl tenfold-diluted serum antibodies from post-vaccination pooled human sera (n=10 each from the 20-million-PFU and 100-million-PFU groups; 5 µl serum from each vaccine to obtain a tenfold dilution for the pooled sera) were adsorbed by incubation in EBOV GFPDL phage-coated petri dishes. To ascertain residual antibody specificity, an ELISA was performed in wells coated with 200 ng/100 recombinant EBOV GP. After blocking with 20 mM PBS, pH 7.4, containing 0.05% Tween-20 (PBST) containing 2% milk, serial dilutions of human serum (with or without adsorption) in blocking solution were added to each well and incubated for 1 h at room temperature (RT) before addition of 5,000-fold diluted HRP-conjugated goat anti-human IgA$^+$IgG$^+$IgM antibody and developed by 100 µl o-phenylenediamine dihydrochloride (OPD) substrate solution. Absorbance was measured at 490 nm.

Affinity selection of EBOV GP GFPDL phages with rVSVΔG-ZEBOV-GP post-vaccination polyclonal human sera. Prior to panning of GFPDL with polyclonal serum antibodies, serum components that could nonspecifically interact with phage proteins were removed by incubation in UV-killed M13K07 phage-coated petri dishes. Equal volumes of pooled polyclonal human sera from each cohort were used for each round of GFPDL panning. All samples in each group (N=10) were pooled for GFPDL analysis. Subsequent GFPDL affinity selection was carried out in solution (with protein A/G) as previously described (Khurana, S. et al. *PLoS Med.* 6, e1000049, 2009; Khurana, S. et al. *Sci. Transl. Med.* 3, 85ra48, 2011). GFPDL affinity selection experiments were performed in quadruplicate (two independent experiments by two different investigators, who were blinded to sample identity) and showed similar numbers of phage clones and epitope repertoires. Additional antibody epitope repertoire analysis was performed using individual post-vaccination sera with similar neutralization titers from 20-million- and 100-million-PFU dose groups using IgA-, IgG- and IgM-specific capture beads to further define the fine epitope specificity of these antibodies in the individual sera using EBOV Kikwit GP GFPDL. A model for the complete Zaire strain GP generated using I-TASSER (Yang, J. et al. *Nat. Methods* 12, 7-8, 2015) was used to represent the antigenic sites on the structure. The crystal structure of Ebola GP (PDB 3CSY) was used as a reference (Lee, J. E. et al. *Nature* 454, 177-182, 2008).

Binding of rVSVΔG-ZEBOV-GP-vaccinated human sera to recombinant GP and off-rate measurements by surface plasmon resonance (SPR). Steadystate equilibrium binding of pre- and post-vaccination human polyclonal sera from every individual in the study was monitored at 25° C. using a ProteOn surface plasmon resonance (Bio-Rad). The purified recombinant GP was coupled to a GLC sensor chip via amine coupling with either 100 or 500 resonance units (RU) in the test flow channels. The protein density on the chip was optimized to measure only monovalent interactions independent of the antibody isotype. Samples of 300 µl freshly prepared sera at tenfold and 100-fold dilution BSAPBST buffer (PBS, pH 7.4, with Tween-20 and BSA) were injected at a flow rate of 50 µl/min (240 s contact duration) for association, and disassociation was performed over a 1,200-s interval. Responses from the protein surface were corrected for the response from a mock surface and for responses from a buffer-only injection. SPR was performed with serially diluted sera (tenfold and 100-fold dilutions) of each sample in this study such that the SPR signal of the samples between 5 to 100 RU was used for further quantitative analysis. The maximum resonance units (max RU) data were calculated by multiplying the observed RU signal with the dilution factor for each serum sample to provide the data for an undiluted serum sample. Antibody isotype analysis for the GP-bound antibodies in post-vaccination polyclonal sera was performed using SPR. Total antibody binding and isotype analysis were calculated with Bio-Rad ProteOn manager software (version 3.0.1). All SPR experiments were performed twice, and the researchers performing the assay were blinded to sample identity. In these optimized SPR conditions, the variation for each sample in duplicate SPR runs was <6%. Antibody off-rate constants, which describe the stability of the complex, i.e., the fraction of complexes decaying per second, were determined directly from the post-rVSVΔG-ZEBOV-GP-vaccination human polyclonal sera sample interaction with rGP protein using SPR (as described above) and calculated using the Bio-Rad ProteOn manager software for the heterogeneous sample model.

Purification of IgG and IgM antibodies from the post-vaccination sera. Fivefold-diluted post-second-vaccination sera were added to anti-human IgG or anti-human IgM immune-affinity resin and incubated for 1 h at RT on an end-to-end shaker before washing and purification of bound antibodies. The antibodies were eluted by 4 M magnesium chloride in 10 mM Tris (pH 7), followed by desalting. The purified IgG and IgM antibodies were normalized by volume to original serum concentrations and tested for GP binding then isotyped using anti-human IgG and anti-human IgM secondary antibodies in SPR to confirm the purity of each antibody isotype preparation. The purified IgG and IgM antibodies were subjected to virus microneutralization assay.

Statistical analyses. The statistical significance of group differences was determined by ordinary one-way ANOVA and Bonferroni's multiple-comparisons method. P<0.05 was considered significant with a 95% confidence interval. Correlations were calculated with the Pearson method, and P values for correlation were calculated by two-tailed test.

Data availability. The data sets generated during and/or analyzed during the study are available from the corresponding author upon reasonable request.

Example 2

This example demonstrates that immunization of rabbits and mice with selected peptide fragments conjugated to the carrier protein, keyhole limpet hemocyanin (KLH), generates strong binding antibodies against the matched Zaire ebolavirus and protects against ebolavirus infection.

Figure 19B:
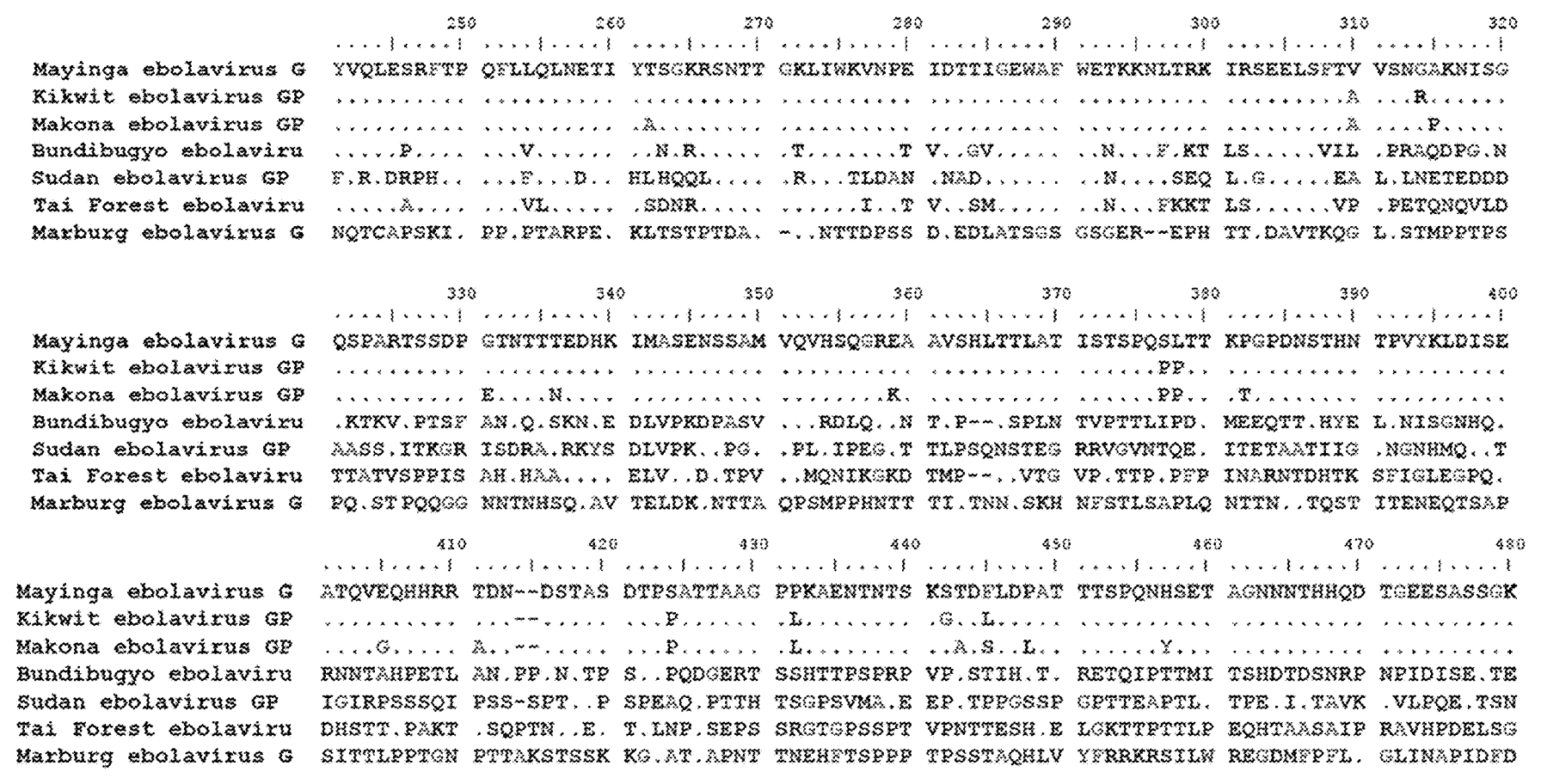

An alignment of the glycoprotein (GP) amino acid sequences of 6 species of ebolavirus (Mayinga (1976), Kikwit (1995), Makona (2014), Bundibugyo (2012), Sudan (2000), Tai Forest) and Marburg margburgvirus is provided in FIGS. 19A-19C. Antigenic sites of ebolavirus GP as described herein are reflected in the table shown in FIG. 20, which shows the sequence of the antigenic site sin the context of the Zaire ebolavirus Mayinga GP sequence set forth as SEQ ID NO: 35.

Peptide fragment conjugation to KLH carrier protein: The conjugation procedure followed for peptide conjugation to Maleimide Activated mcKLH was performed as described in the product manual of Imject® Maleimide Activated mcKLH (Product 77605, Thermo Scientific). Several different fragments of SEQ ID NO: 35 were conjugated to the mcKLH.

Rabbit Immunization Studies:

Female New Zealand white rabbits were immunized three times intra-muscularly at 21-days interval with 25 micrograms of KLH conjugated peptides. Sera was collected before (prevaccination) and after 3rd vaccination and analyzed for binding antibodies using Surface Plasmon Resonance (SPR) and neutralization assay.

Binding of glycoprotein (GP) peptide vaccinated rabbit sera to different EBOV GP's and cross-reactivity measurements by Surface Plasmon Resonance (SPR): Steadystate equilibrium binding of pre- and post-KLH-GP vaccinated rabbit polyclonal sera from every rabbit was monitored at 25 degrees Celsius using a ProteOn surface plasmon resonance (Bio Rad). The purified GP were coupled to a GLC sensor chip via amine coupling with 500 resonance units (RU) in the test flow channels. The protein density on the chip was optimized such as to measure only monovalent interactions. Samples of 300 microliters of freshly prepared sera at 10-fold dilution in BSA-PBST buffer (PBS pH 7.4 buffer with Tween-20 and BSA) were injected at a flow rate of 50 microliters/min (240 sec contact duration) for association, and disassociation was performed over a 1200-second interval. Responses from the protein surface were corrected for the response from a mock surface and for responses from a buffer-only injection. The resonance units (RU) data shown for each sera in FIG. 21 was the observed RU signal for each serum sample.

Pseudovirion neutralization (PsVN) Assay: Pseudovirion neutralization assay (PsVNA) against the homologous Zaire-Kikwit strain glycoprotein was performed as described previously (Regules, J. A. et al. N. Engl. J. Med. 376(4):330-341, 2017, available online Apr. 1, 2015)

Discussion Immunization of rabbits with selected ebolavirus antigenic peptides generated strong binding antibodies against the matched Ebola virus strain. Some of the immunized rabbit sera also showed strong cross reactivity to diverse ebolavirus strains including Bundibugyo and the Makona strain from the recent 2014 epidemic in Western Africa as well as diverse Sudan virus.

Rabbit anti-GP peptide post-vaccination sera were analyzed for virus neutralization in the PsVNA against the Zaire Mayinga strain showed that five antigenic peptides generated neutralizing antibodies (anti-GP 335-364, GP 457-484, GP 469-498, GP 617-645 and GP 630-646) against the Mayinga (1976) strain. Two of these peptides from the carboxy terminus of GP (GP 617-645 and GP 630-646) upon rabbit immunization generated strong neutralizing titers when tested in the conventional BSL4 based wild type Ebola virus with end-point titers of 320 and 640. Results are shown in the following table:

| Neutralization titers of anti-GP peptide Rabbit sera | | | | | |
|---|---|---|---|---|---|
| | GP 457-484 | GP 630-646 | GP 335-364 | GP 469-498 | GP 617-645 |
| Pseudovirus Neut-Mayinga | 62.24 | 194.1 | 85 | 44.86 | 79.14 |
| Wild type PRNT-Mayinga | 40 | 640 | 40.00 | 40 | 320 |
| Pseudovirus Neut-Kikwit | 45 | 179 | 62 | | |
| Pseudovirus Neut-Makona | 38.74 | 84.14 | 41.04 | | |

These anti-peptide rabbit sera also showed cross-neutralization of the distinct Kikwit and 2014-Makona strain as well with C-terminal peptide (GP 630-646) immunized sera showing the highest cross-neutralization titers.

Additional immunization assays were performed as discussed above using the peptides shown in FIG. 22. Again, peptides from the C-terminus of GP (GP 282-305, GP 343-368 and GP 520-547) that elicited a neutralizing immune response.

These rabbit studies confirmed that these antigenic GP peptides are immunogenic when vaccinated into animals that bind diverse multiple ebolaviruses and five of these conserved peptides generated neutralizing antibodies that also cross-neutralized diverse ebolaviruses.

Mouse Immunization and Challenge Studies

In another experiment (depicted in FIG. 23), female BALB/C mice were immunized on days 0 and 29 intramuscularly with 20 micrograms of a KLH conjugated peptide (peptide fragments comprising SEQ ID NO: 17, SEQ ID NO: 21, SEQ ID NO: 3, SEQ ID NO: 29, SEQ ID NO: 10), each KLH-conjugated peptide fragment was screened separately. Furthermore, Female BALB/C mice were also used to study immunization with a combination of peptide fragments, a total of 20 micrograms comprising 4 microgram of each of the five KLH conjugated peptides (peptide fragments comprising SEQ ID NO: 17, SEQ ID NO: 21, SEQ ID NO: 3, SEQ ID NO: 29, SEQ ID NO: 10), with 10 mice per group). As a control, mice were injected with 20 micrograms of KLH only, or a particle based vaccine (VRP) expressing full length Zaire EBOV GP.

At day 63, the mice were challenged with 100 pfu Zaire ebolavirus Immunization with peptides from antigenic sites V.7 (SEQ ID NO: 3) and VI (SEQ IDNO: 10) induced sterilizing immunity to the viral challenge (FIG. 23), and protected against weight loss (FIG. 24).

Following immunization but prior to the viral challenge, sera was collected to assess the specificity of the immune response by surface plasmon resonance. As shown in FIG. 25, the conserved antigenic sites in the C-terminal region of GP1 and GP2 generate strong binding antibodies to both Mayinga and Makona GP.

Characterization of Human Sera from Ebolavirus Survivors

Additional assays were performed to determine if sera from subjects previously infected with Zaire ebolavirus targeted peptides corresponding to the antigenic sites identified herein (FIG. 26-27). Sera from infected human subjects targeted several of the identified sites, some of which strongly correlated with ebolavirus neutralization titers. The spatial structure of several of these sites is shown in FIG. 28

It will be apparent that the precise details of the methods or compositions described may be varied or modified without departing from the spirit of the described embodiments. We claim all such modifications and variations that fall within the scope and spirit of the claims below.

The invention claimed is:

1. A method for generating an immune response to ebolavirus glycoprotein (GP) in a subject, comprising administering to the subject an effective amount of a peptide to generate the immune response, wherein the peptide comprises an amino acid sequence set forth as SEQ ID NO: 3, and wherein the peptide is no more than 40 amino acids in length.

2. The method of claim 1, wherein the ebolavirus is selected from any one of Zaire ebolavirus, Mayinga ebolavirus, Kikwit ebolavirus, or Makona ebolavirus.

3. The method of claim 1, wherein the peptide is linked to a heterologous carrier.

4. The method of claim 3, wherein the peptide is linked to the carrier by a linker.

5. The method of claim 3, wherein the carrier is a heterologous protein and the peptide is linked to the heterologous protein via a peptide linker to form a fusion protein.

6. The method of claim 3, wherein the carrier comprises Keyhole Limpet Hemocyanin (KLH), Concholepas Hemocyanin (CCH), Ovalbumin (OVA), bovine serum albumin, recombinant *B. anthracis* protective antigen, recombinant *P. aeruginosa* exotoxin A, tetanus toxoid, tetanus toxin heavy chain C fragment, diphtheria toxoid, diphtheria toxin variant CRM197, pertussis toxoid, H influenza protein D (HiD), recombinant *Clostridium difficile* toxin B subunit (rBRU), *C. perfringens* toxoid, or analogs or mimetics of and combinations of two or more thereof.

7. The method of claim 6, wherein the carrier is Keyhole Limpet Hemocyanin (KLH).

8. The method of claim 1, wherein the peptide consists of or consists essentially of the amino acid sequence set forth as SEQ ID NO: 3.

9. The method of claim 1, further comprising selecting the subject, wherein the subject has or is at risk of having an ebolavirus infection.

10. The method of claim 1, wherein the immune response inhibits an ebolavirus infection.

11. The method of claim 1, wherein the immune response treats an ebolavirus infection.

12. A method for generating an immune response to ebolavirus glycoprotein (GP) in a subject, comprising administering to the subject an effective amount of a peptide to generate the immune response wherein the peptide consists of or consists essentially of the antigenic site V.7 amino acid sequence set forth as SEQ ID NO: 3.

\* \* \* \* \*